(12) United States Patent
Hu et al.

(10) Patent No.: US 9,617,257 B2
(45) Date of Patent: Apr. 11, 2017

(54) FUSED PYRIDINE DERIVATIVES USEFUL AS C-MET TYROSINE KINASE INHIBITORS

(71) Applicant: BETA PHARMACEUTICALS CO., LTD., Hangzhou, Zheijiang (CN)

(72) Inventors: Shaojing Hu, Beijing (CN); Fei Wang, Beijing (CN); Zhiguo Xu, Beijing (CN); Yanping Wang, Beijing (CN); Yinxiang Wang, Beijing (CN)

(73) Assignee: Betta Pharmaceuticals Co., LTD, Hangzhou (CN)

( * ) Notice: Subject to any disclaimer, the term of this patent is extended or adjusted under 35 U.S.C. 154(b) by 0 days.

(21) Appl. No.: 14/411,515

(22) PCT Filed: Jul. 1, 2013

(86) PCT No.: PCT/CN2013/078592
§ 371 (c)(1),
(2) Date: Dec. 28, 2014

(87) PCT Pub. No.: WO2014/000713
PCT Pub. Date: Jan. 3, 2014

(65) Prior Publication Data
US 2015/0315210 A1  Nov. 5, 2015

(30) Foreign Application Priority Data

Jun. 29, 2012  (WO) ................ PCT/CN2012/077924

(51) Int. Cl.
*C07D 471/04* (2006.01)
*C07D 498/04* (2006.01)
*C07D 513/04* (2006.01)

(52) U.S. Cl.
CPC ......... *C07D 471/04* (2013.01); *C07D 498/04* (2013.01); *C07D 513/04* (2013.01)

(58) Field of Classification Search
CPC ... C07D 471/04; C07D 498/04; C07D 513/04
See application file for complete search history.

(56) References Cited

U.S. PATENT DOCUMENTS

2008/0312270 A1   12/2008   Brown et al.

FOREIGN PATENT DOCUMENTS

| CN | 101248080 A | 8/2008 |
|---|---|---|
| CN | 102086211 A | 6/2011 |
| WO | WO 2006/060318 A2 | 6/2006 |
| WO | WO 2006/116713 A1 | 11/2006 |
| WO | WO 2007/054831 A2 | 5/2007 |

OTHER PUBLICATIONS

Zhang et al. Chemicla Research in Toxicology, 2012, 25, 556-571.*
International Search Report for PCT/CN2013/078592 issued from the State Intellectual Property Office, the P.R. China, dated Oct. 17, 2013 (6 pages).
Christensen, J. G., et al., "c-Met as a Target for Human Cancer and Characterization of Inhibitors for Therapeutic Intervention", Cancer Letters, vol. 225 (2005), pp. 1-26.
Park, W.S., et al., "Somatic Mutations in the Kinase Domain of the Met/Hepatocyte Growth Factor Receptor Gene in Childhood Hepatocellular Carcinomas", Cancer Research, vol. 59 (1999), pp. 59-307.
Zou, H.Y., et al., "An Orally Available Small-Molecule Inhibitor of c-Met, PF-2341066, Exhibits Cytoreductive Antitumor Efficacy through Antiproliferative and Antiangiogenic Mechanisms", Cancer Research, vol. 67, (2007), pp. 4408-4417.
Ma, P.C., et al., "c-MET Mutational Analysis in Small Cell Lung Cancer: Novel Juxtamembrane Domain Mutations Regulating Cytoskeletal Functions", Cancer Research, vol. 63, Oct. 1, 2003, pp. 6272-6281.
Jiang, W., et al., "Hepatocyte Growth Factor/Scatter Factor, its Molecular, Cellular and Clinical Implications in Cancer", Critical Reviews in Oncology/Hematology 29 (1999), pp. 209-248.
Danilkovitch-Miagkova, A., et al., "Dysregulation of Met Receptor Tyrosine Kinase Activity in Invasive Tumors", The Journal of Investigation, vol. 109 (2002), pp. 863-867.
Birchmeier, C., et al., "MET, Metastasis, Motility and More", Nature Review Molecular Biology, vol. 4, (2003), pp. 915-925.
Blume-Jensen, P., et al., "Oncogenic Kinase Signalling", Nature, vol. 411 (2001), pp. 355-365.
Lee, J.-H., et al., "A Novel Germ Line Juxtamembrane Met Mutation in Human Gastric Cancer", Oncogene, vol. 19 (2000), pp. 4947-4953.
Di Renzo, M.F., et al., "Somantic Mutations of the MET Oncogene are Selected During Metastatic Spread of Human HNSC Carcinomas", Oncogene, vol. 19 (2000), pp. 1547-1555.
Schmidt, L., et al., "Germline and Somantic Mutations in the Tyrosine Kinase Domain of the MET Proto-Oncogene in Papillary Renal Carcinomas", Nature Genetics, vol. 16 (1997), pp. 68-73.

* cited by examiner

*Primary Examiner* — Rebecca Anderson
(74) *Attorney, Agent, or Firm* — Finnegan, Henderson, Farabow, Garrett & Dunner LLP

(57) ABSTRACT

This invention relates to novel fused quinazoline derivatives of Formula I as c-Met inhibitors, their synthesis and uses for treating c-Met mediated disorders.

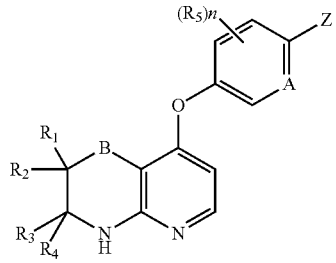

Formula I

38 Claims, No Drawings

FUSED PYRIDINE DERIVATIVES USEFUL AS C-MET TYROSINE KINASE INHIBITORS

TECHNICAL FIELD

Cross Reference to Related Application

This application is a national phase application based on PCT/CN2013/078592, filed Jul. 1, 2013, which claims the priority of PCT/CN2012/077924, filed Jun. 29, 2012.

This invention relates to certain novel fused pyridine derivatives as c-Met inhibitors, their synthesis and their use for treating a c-Met mediated disorder.

BACKGROUND ART

The study of signal transduction pathways in normal and pathological states is of considerable interest because of the potential therapeutic benefit arising from new molecular agents targeting certain of these pathways associated with disease.

Receptor tyrosine kinases (RTKs) are key enzymes in signal transduction pathways that catalyse the autophosphorylation of tyrosine residues within the cytosolic, C-terminal domain of the protein. This generates docking sites for the recruitment of downstream proteins and the subsequent propagation of signals involved in an array of cellular events including growth, proliferation and survival. More generally deregulated kinase signalling is implicated in a diverse range of pathological states including immunological and inflammatory disorders, cardiovascular and neurodegenerative disease. The known receptor tyrosine kinases encompass 20 families and many are oncogenes (Blume-Jensen P et al. 2001. Nature 411 355-365). c-Met is the prototypic member of a subfamily of RTKs which includes the related proteins Ron (macrophage-stimulating protein receptor) and its chicken orthologue, Sea. The endogenous ligand is the growth and motility factor hepatocyte growth factor (HGF, also known as Scatter Factor). c-Met and HGF are expressed in a range of tissue types although their expression is normally restricted to cells of epithelial and mesenchymal origin. In contrast, tumour cells often express constitutively activated c-Met.

There is now a growing body of compelling evidence from both animal studies and cancer patients that HGF-Met signalling plays an important role in the development and progression of malignancy and is associated in particular with invasive phenotypes. c-Met and HGF are highly expressed relative to surrounding tissue in numerous cancers and their expression correlates with poor patient prognosis (Jiang, W et al. 1999 Crit. Rev. Oncol.-hematol., 29, 209-248.) Activating point mutations in the kinase domain of c-Met are implicated in the cause of sporadic and hereditary forms of papillary renal carcinoma (Danilkovitch-Miagkova, A et al 2002. 1 J. Clin. Invest. 109, 863-867). c-Met is a marker for both cancer and malignancy and agents that inhibit c-Met-HGF signalling can be expected to ameliorate disease progression in relevant cancers.

SUMMARY OF INVENTION

The present invention relates to novel fused pyridine compounds useful as c-Met inhibitors and for the treatment of conditions mediated by c-Met. The compounds of the invention have the general structure as Formula I:

A compound of Formula I or a pharmaceutically acceptable salt, solvate, chelate, non-covalent complex, or prodrug thereof:

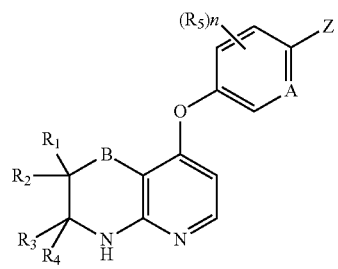

I wherein,

B is absent, O, S, $OCH_2$, or $SCH_2$;

$R_1$, $R_2$, $R_3$ and $R_4$ are each independently hydrogen, halogen, substituted or unsubstituted $C_{1-6}$alkyl, substituted or unsubstituted $C_{2-8}$alkenyl, substituted or unsubstituted $C_{2-8}$alkynyl, substituted or unsubstituted aryl, substituted or unsubstituted heteroaryl, substituted or unsubstituted heterocyclyl, $C_{1-8}$alkanoyl, ($C_{1-8}$alkoxy)carbonyl, $C_{1-8}$alkylsulphinyl, $C_{1-8}$alkylsulphonyl, arylsulphonyl, —CN, —$NO_2$, hydroxy, amino, carboxy, oxo, carbamoyl, $C_{1-8}$alkoxy, $C_{2-8}$alkenyloxy, $C_{2-8}$alknyloxy, $C_{1-8}$alkylthio, N—($C_{1-8}$alkyl)carbamoyl, N,N-di($C_{1-8}$alkyl)carbamoyl, $C_{1-8}$alkanoyloxy, $C_{1-8}$alkanoylamino, $C_{3-8}$alkynoylamino, N—($C_{1-8}$alkyl)sulphamoyl, or N,N-di($C_{1-8}$alkyl)sulphamoyl; or $R_1$ and $R_2$ together, or $R_3$ and $R_4$ together, form =O;

A is N or CH;

n is 0, 1, 2, or 3;

each $R_5$ is independently halogen, substituted or unsubstituted $C_{1-6}$alkyl, —CN, —$NO_2$, —$OR_{50}$, —$N(R_{50})_2$, —$S(O)_{0-2}R_{50}$, or —$C(O)R_{50}$;

each $R_{50}$ is independently hydrogen or substituted or unsubstituted $C_{1-6}$alkyl;

Z is $NHR_6$ or of Formula II:

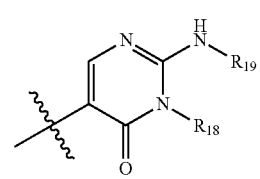

II wherein $R_{18}$ and $R_{19}$ are each independently hydrogen, substituted or unsubstituted $C_{1-8}$alkyl, substituted or unsubstituted $C_{2-8}$alkenyl, substituted or unsubstituted $C_{2-8}$alkynyl, substituted or unsubstituted aryl, substituted or unsubstituted heteroaryl, substituted or unsubstituted heterocyclyl, $C_{1-8}$ alkanoyl, ($C_{1-8}$alkoxy)carbonyl, $C_{1-8}$alkylsulphinyl, $C_{1-8}$alkylsulphonyl, or arylsulphonyl;

$R_6$ is of Formula III, IV, V, VI, or VII:

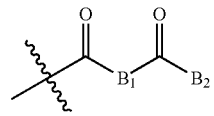

III

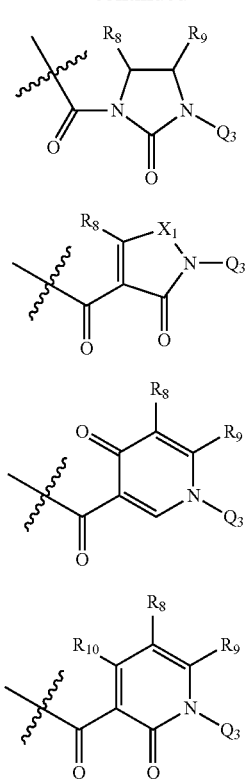

wherein:

$B_1$ is

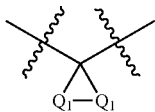

wherein each $Q_1$ is independently $C(R_7)_2$;

$B_2$ is $NHQ_2$ and $Q_2$ is substituted or unsubstituted aryl, substituted or unsubstituted heteroaryl, substituted or unsubstituted heterocyclyl, substituted or unsubstituted ($C_{1-8}$alkyl)aryl, substituted or unsubstituted ($C_{1-8}$alkyl)heteroaryl, or substituted or unsubstituted ($C_{1-8}$alkyl)heterocyclyl; or $B_1$ and $B_2$, together with the carbonyl group therebetween, form a 5- to 10-membered substituted or unsubstituted heteroaryl, or substituted or unsubstituted heterocyclyl;

$Q_3$ is hydrogen, substituted or unsubstituted aryl, substituted or unsubstituted alkyl, substituted or unsubstituted heteroaryl, substituted or unsubstituted heterocyclyl, substituted or unsubstituted ($C_{1-8}$alkyl)aryl, substituted or unsubstituted ($C_{1-8}$alkyl)heteroaryl, or substituted or unsubstituted ($C_{1-8}$alkyl)heterocyclyl;

$X_1$ is $NR_8$ or $CR_8R_9$;

$R_7$, $R_8$, $R_9$ and $R_{10}$ are each independently hydrogen, halogen, substituted or unsubstituted $C_{1-8}$alkyl, substituted or unsubstituted $C_{2-8}$alkenyl, substituted or unsubstituted $C_{2-8}$alkynyl, substituted or unsubstituted aryl, substituted or unsubstituted heteroaryl, substituted or unsubstituted heterocyclyl, $C_{1-8}$alkanoyl, ($C_{1-8}$alkoxy)carbonyl, $C_{1-8}$alkylsulphinyl, $C_{1-8}$alkylsulphonyl, arylsulphonyl, —CN, —NO$_2$, hydroxy, amino, carboxy, oxo, carbamoyl, $C_{1-8}$alkoxy, $C_{2-8}$alkenyloxy, $C_{2-8}$alknyloxy, $C_{1-8}$alkylthio, N—($C_{1-8}$alkyl)carbamoyl, N,N-di($C_{1-8}$alkyl)carbamoyl, $C_{1-8}$alkanoyloxy, $C_{1-8}$alkanoylamino, $C_{3-8}$alkynoylamino, N—($C_{1-8}$alkyl)sulphamoyl, N,N-di($C_{1-8}$alkyl)sulphamoyl, substituted or unsubstituted $C_{1-8}$alkylaryl, substituted or unsubstituted $C_{1-8}$alkylheteroaryl, or substituted or unsubstituted $C_{1-8}$alkylheterocyclyl.

The present invention further provides some preferred technical solutions with regard to compound of Formula (I).

In some embodiments of Formula (I), $R_1$, $R_2$, $R_3$ and $R_4$ are each independently hydrogen, halogen, substituted or unsubstituted $C_{1-4}$alkyl, substituted or unsubstituted $C_{6-8}$aryl, cyano, nitro, hydroxy, amino, carboxy, oxo, carbamoyl, or $C_{1-8}$alkoxy; or $R_1$ and $R_2$ together, or $R_3$ and $R_4$ together form =O.

In some embodiments of Formula (I), $R_1$, $R_2$, $R_3$ and $R_4$ are independently selected from hydrogen, halogen, substituted or unsubstituted $C_{1-4}$alkyl, substituted or unsubstituted $C_{6-8}$aryl; or $R_1$ and $R_2$ together, or $R_3$ and $R_4$ together, form =O.

In some embodiments of Formula (I), $R_1$, $R_2$, $R_3$ and $R_4$ are each independently hydrogen, halogen, or substituted or unsubstituted $C_{1-4}$alkyl; or $R_1$ and $R_2$ together, or $R_3$ and $R_4$ together, form =O.

In some embodiments of Formula (I), $R_1$, $R_2$, $R_3$ and $R_4$ are each independently hydrogen, halogen, methyl, ethyl, propyl, or phenyl; or $R_1$ and $R_2$ together, or $R_3$ and $R_4$ together, form =O.

In some embodiments of Formula (I), $R_1$, $R_2$, $R_3$ and $R_4$ are each independently hydrogen, F, or methyl; or $R_1$ and $R_2$ together, or $R_3$ and $R_4$ together form =O.

In some embodiments of Formula (I), $R_1$, $R_2$, $R_3$ and $R_4$ are each independently hydrogen or halogen.

In some embodiments of Formula (I), $R_1$, $R_2$, $R_3$ and $R_4$ are each independently F, Cl or Br.

In some embodiments of Formula (I), $R_1$, $R_2$, $R_3$ and $R_4$ are each independently methyl, ethyl, or propyl.

In some embodiments of Formula (I), $R_1$, $R_2$, $R_3$ and $R_4$ are all hydrogen.

In some embodiments of Formula (I), $R_1$ and $R_2$ together, or $R_3$ and $R_4$ together, form =O.

In some embodiments of Formula (I), $R_3$ and $R_4$ together form =O.

In some embodiments of Formula (I), n is 0 or 1.

In some embodiments of Formula (I), n is 1.

In some embodiments of Formula (I), $R_5$ is hydrogen, halogen, —N($R_{50}$)$_2$, —C(O) $R_{50}$, or substituted and unsubstituted $C_{1-4}$alkyl, and each $R_{50}$ is independently hydrogen, methyl, ethyl, or propyl.

In some embodiments of Formula (I), $R_5$ is hydrogen or halogen.

In some embodiments of Formula (I), $R_5$ is hydrogen, F, Cl, or Br.

In some embodiments of Formula (I), $R_5$ is hydrogen, F, methyl, —NH$_2$, or COCH$_3$.

In some embodiments of Formula (I), m is absent or O.

In some embodiments of Formula (I), m is absent.

In some embodiments of Formula (I), Z is of Formula II wherein $R_{18}$ and $R_{19}$ are each independently hydrogen, substituted or unsubstituted methyl, substituted or unsubstituted ethyl, substituted or unsubstituted propyl, substituted or unsubstituted $C_{6-8}$aryl, substituted or unsubstituted heteroaryl.

In some embodiments of Formula (I), Z is of Formula II wherein $R_{18}$ and $R_{19}$ are each independently hydrogen, substituted or unsubstituted methyl, or substituted or unsubstituted phenyl.

In some embodiments of Formula (I), Z is of Formula II wherein, $R_{18}$ and $R_{19}$ are each independently hydrogen, methyl, phenyl, or phenyl substituted with halogen.

In some embodiments of Formula (I), Z is of Formula II wherein, $R_{18}$ and $R_{19}$ are each independently hydrogen, methyl, phenyl, or phenyl substituted with F or Cl.

In some embodiments of Formula (I), Z is of Formula II wherein $R_{18}$ and $R_{19}$ are each independently hydrogen, methyl, or phenyl substituted with F.

In some embodiments of Formula (I), Z is of Formula II wherein $R_{18}$ is hydrogen or methyl; and $R_{19}$ is phenyl substituted with F.

In some embodiments of Formula (I), Z is of Formula II wherein $R_{18}$ is hydrogen or methyl; and $R_{19}$ is phenyl substituted with F at the para-position.

In some embodiments of Formula (I), Z is $NHR_6$ and $R_6$ is of Formula VI; $Q_3$ is hydrogen, substituted or unsubstituted $C_{1-3}$alkyl, or substituted or unsubstituted $C_{6-8}$aryl; $R_8$ and $R_9$ are each independently hydrogen, halogen, substituted or unsubstituted $C_{1-3}$alkyl, substituted or unsubstituted $C_{6-8}$aryl, substituted or unsubstituted heteroaryl, substituted or unsubstituted heterocyclyl.

In some embodiments of Formula (I), Z is $NHR_6$ and $R_6$ is of Formula VI; $Q_3$ is hydrogen, substituted or unsubstituted methyl, ethyl, propyl, or substituted or unsubstituted phenyl; $R_8$ and $R_9$ are each independently hydrogen, halogen, or substituted or unsubstituted aryl.

In some embodiments of Formula (I), Z is $NHR_6$ and $R_6$ is of Formula VI; $Q_3$ is hydrogen, methyl, ethyl, propyl, or halosubstituted or unsubstituted phenyl; $R_8$ and $R_9$ are each independently hydrogen or substituted or unsubstituted phenyl.

In some embodiments of Formula (I), Z is $NHR_6$ and $R_6$ is of Formula VI; $Q_3$ is hydrogen, methyl, phenyl, or phenyl substituted with halogen; $R_8$ and $R_9$ are each independently hydrogen, phenyl, or phenyl substituted with halogen.

In some embodiments of Formula (I), Z is $NHR_6$ and $R_6$ is of Formula VI; $Q_3$ is hydrogen, methyl, phenyl, or phenyl substituted with halogen at the para-position; $R_8$ and $R_9$ are each independently hydrogen, phenyl, or phenyl substituted with halogen at the para-position.

In some embodiments of Formula (I), Z is selected from $NHR_6$ and $R_6$ is of Formula VI; $Q_3$ is hydrogen, methyl, phenyl, or phenyl substituted with fluorine at the para-position; $R_8$ and $R_9$ are each independently hydrogen or phenyl substituted with fluorine at the para-position.

In some embodiments of Formula (I), Z is $NHR_6$ and $R_6$ is of Formula VI; $Q_3$ is hydrogen, methyl, phenyl, or phenyl substituted with fluorine at the para-position; $R_8$ is hydrogen; and $R_9$ is hydrogen, phenyl, or phenyl substituted with fluorine at the para-position.

In some embodiments of Formula (I), Z is $NHR_6$ and $R_6$ is of Formula VI; $Q_3$ is hydrogen, $R_8$ is substituted or unsubstituted phenyl; and $R_9$ is hydrogen.

In some embodiments of Formula (I), Z is $NHR_6$ and $R_6$ is of Formula VI; $Q_3$ is hydrogen; $R_9$ is phenyl or phenyl substituted with halogen; and $R_9$ is hydrogen.

In some embodiments of Formula (I), Z is $NHR_6$ and $R_6$ is of Formula VI; $Q_3$ is hydrogen; $R_9$ is hydrogen; and $R_8$ is phenyl substituted with halogen at the para-position.

In some embodiments of Formula (I), Z is $NHR_6$ and $R_6$ is of Formula VI; $Q_3$ is hydrogen; $R_9$ is hydrogen; and $R_8$ is phenyl substituted with fluorine at the para-position.

In some embodiments of Formula (I), Z is $NHR_6$ and $R_6$ is of Formula VII; $Q_3$ is selected from hydrogen or substituted or unsubstituted aryl, $R_8$, $R_9$ and $R_{10}$ are each independently hydrogen, substituted or unsubstituted $C_{1-3}$alkyl, substituted or unsubstituted aryl.

In some embodiments of Formula (I), Z is $NHR_6$ and $R_6$ is of Formula VII; $Q_3$ is hydrogen or substituted or unsubstituted phenyl; $R_8$, $R_9$ and $R_{10}$ are each independently hydrogen or substituted or unsubstituted phenyl.

In some embodiments of Formula (I), Z is $NHR_6$ and $R_6$ is of Formula VII; $Q_3$ is phenyl substituted with halogen; and $R_8$, $R_9$ and $R_{10}$ are each hydrogen.

In some embodiments of Formula (I), Z is $NHR_6$ and $R_6$ is of Formula VII; $Q_3$ is phenyl substituted with halogen at the para-position; and $R_8$, $R_9$ and $R_{10}$ are each hydrogen.

In some embodiments of Formula (I), Z is $NHR_6$ and $R_6$ is of Formula VII; $Q_3$ is phenyl substituted with fluorine at the para-position; and $R_8$, $R_9$ and $R_{10}$ are each hydrogen.

In some embodiments of Formula (I), Z is $NHR_6$ and $R_6$ is of Formula V; $Q_3$ is substituted or unsubstituted phenyl; $X_1$ is $NR_8$ and $R_8$ is hydrogen, halogen, or substituted or unsubstituted $C_{1-4}$alkyl.

In some embodiments of Formula (I), Z is $NHR_6$ and $R_6$ is of Formula V; $Q_3$ is phenyl; $X_1$ is $NR_8$ and $R_8$ is hydrogen or $C_{1-4}$alkyl.

In some embodiments of Formula (I), Z is $NHR_6$ and $R_6$ is of Formula V; $Q_3$ is phenyl; $X_1$ is $NR_8$ and $R_8$ is methyl.

In some embodiments of Formula (I), Z is $NHR_6$ and $R_6$ is Formula III; $R_7$ is hydrogen, halogen, or substituted or unsubstituted $C_{1-4}$alkyl; $Q_2$ is substituted or unsubstituted $C_{6-8}$aryl, substituted or unsubstituted $C_{6-8}$heteroaryl.

In some embodiments of Formula (I), Z is $NHR_6$ and $R_6$ is of Formula III; $R_7$ is hydrogen or $C_{1-4}$alkyl; $Q_2$ is substituted or unsubstituted phenyl.

In some embodiments of Formula (I), Z is $NHR_6$ and $R_6$ is of Formula III; $R_7$ is hydrogen, $Q_2$ is phenyl or phenyl substituted with halogen.

In some embodiments of Formula (I), Z is $NHR_6$ and $R_6$ is of Formula III; $R_7$ is hydrogen; $Q_2$ is phenyl substituted with halogen.

In some embodiments of Formula (I), Z is $NHR_6$ and $R_6$ is of Formula III; $R_7$ is hydrogen; $Q_2$ is phenyl substituted with halogen at the para-position.

In some embodiments of Formula (I), Z is $NHR_6$ and $R_6$ is of Formula III; $R_7$ is hydrogen; $Q_2$ is phenyl substituted with fluorine at the para-position.

In some embodiments of Formula (I), Z is $NHR_6$ and $R_6$ is of Formula IV; $R_7$ and $R_8$ are each independently hydrogen, halogen, substituted or unsubstituted $C_{1-5}$alkyl.

In some embodiments of Formula (I), Z is $NHR_6$ and $R_6$ is of Formula IV; $R_7$ and $R_8$ are each independently hydrogen or halogen.

In some embodiments of Formula (I), Z is $NHR_6$ and $R_6$ is of Formula IV; $R_7$ and $R_8$ are each independently F, Cl or Br.

In some embodiments of Formula (I), Z is $NHR_6$ and $R_6$ is of Formula IV; $R_7$ and $R_8$ are each independently methyl, ethyl, or propyl.

In some embodiments of Formula (I), Z is $NHR_6$ and $R_6$ is of Formula IV; $Q_3$ is hydrogen, substituted or unsubstituted $C_{6-8}$aryl, or substituted or unsubstituted $C_{1-5}$alkyl.

In some embodiments of Formula (I), Z is $NHR_6$ and $R_6$ is of Formula IV; $Q_3$ is hydrogen, substituted or unsubstituted methyl, substituted or unsubstituted ethyl, or substituted or unsubstituted propyl.

In some embodiments of Formula (I), Z is $NHR_6$ and $R_6$ is of Formula IV; $Q_3$ is hydrogen, methyl, ethyl, or propyl.

In some embodiments of Formula (I), Z is selected from $NHR_6$ and $R_6$ is of Formula IV; and $Q_3$ is phenyl.

The present invention further provides some more preferred technical solutions with regard to compounds of Formula (I).

In some embodiments, the compound of Formula (I) is of Formula VIII:

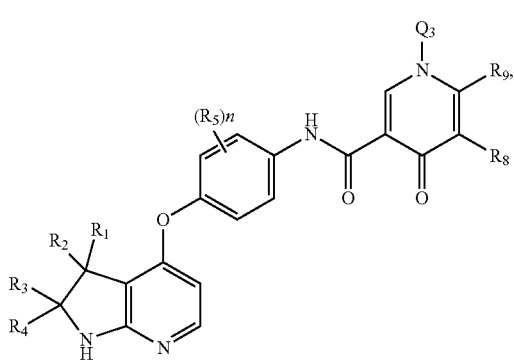

VIII wherein, $R_1$, $R_2$, $R_3$ and $R_4$ are each independently hydrogen or halogen; or $R_1$ and $R_2$ together, or $R_3$ and $R_4$ together, form =O;

each $R_5$ is independently halogen;

n is 0 or 1;

Q is hydrogen, substituted or unsubstituted $C_{6-8}$aryl; and $R_8$ and $R_9$ are each independently hydrogen, methyl, or phenyl substituted with halogen.

The present invention further provides some preferred technical solutions of Formula VIII:

In some embodiments of compound of Formula VIII, $R_1$, $R_2$, $R_3$ and $R_4$ are each hydrogen.

In some embodiments of compound of Formula VIII, $Q_3$ is hydrogen.

In some embodiments of compound of Formula VIII, $R_8$ is hydrogen; $R_9$ is hydrogen, phenyl, or phenyl substituted with halogen.

In some embodiments of compound of Formula VIII, $R_8$ is hydrogen, $R_9$ is phenyl substituted with halogen at the para-position.

In some embodiments of compound of Formula VIII, $R_8$ is hydrogen, $R_9$ is phenyl substituted with fluorine at the para-position.

The present invention further provides some especially preferred technical solutions with regard to compound of Formula I. The compound is:

N-(4-(2,3-dihydro-1H-pyrrolo[2,3-b]pyridin-4-yloxy)-3-fluorophenyl)-5-(4-fluorophenyl)-4-oxo-1,4-dihydropyridine-3-carboxamide;

N-(3-fluoro-4-(3-oxo-3,4-dihydro-2H-pyrido[3,2-b][1,4]oxazin-8-yloxy)phenyl)-5-(4-fluorophenyl)-4-oxo-1,4-dihydropyridine-3-carboxamide;

N-(4-(3,4-dihydro-2H-pyrido[3,2-b][1,4]oxazin-8-yloxy)-3-fluorophenyl)-5-4-fluorophenyl)-4-oxo-1,4-dihydropyridine-3-carboxamide;

N-(4-(3,4-dihydro-2H-pyrido[3,2-b][1,4]oxazin-8-yloxy)phenyl)-5-(4-fluorophenyl)-4-oxo-1,4-dihydropyridine-3-carboxamide;

N-(3-fluoro-4-(2-oxo-2,3-dihydro-1H-pyrrolo[2,3-b]pyridin-4-yloxy)phenyl)-5-(4-fluorophenyl)-4-oxo-1,4-dihydropyridine-3-carboxamide;

N-(3-fluoro-4-(3-oxo-3,4-dihydro-2H-pyrido[3,2-b][1,4]oxazin-8-yloxy)phenyl)-1-(4-fluorophenyl)-2-oxo-1,2-dihydropyridine-3-carboxamide;

N-(4-(2,3-dihydro-1H-pyrrolo[2,3-b]pyridin-4-yloxy)-3-fluorophenyl)-1-(4-fluorophenyl)-2-oxo-1,2-dihydropyridine-3-carboxamide;

N-(4-(3,4-dihydro-2H-pyrido[3,2-b][1,4]oxazin-8-yloxy)-3-fluorophenyl)-1-(4-fluorophenyl)-2-oxo-1,2-dihydropyridine-3-carboxamide;

N-(4-(3,4-dihydro-2H-pyrido[3,2-b][1,4]oxazin-8-yloxy)phenyl)-1-(4-fluorophenyl)-2-oxo-1,2-dihydropyridine-3-carboxamide;

N-(3-fluoro-4-(2-oxo-2,3-dihydro-1H-pyrrolo[2,3-b]pyridin-4-yloxy)phenyl)-1-(4-fluorophenyl)-2-oxo-1,2-dihydropyridine-3-carboxamide;

N-(3-fluoro-4-(3-oxo-3,4-dihydro-2H-pyrido[3,2-b][1,4]oxazin-8-yloxy)phenyl)-N-(4-fluorophenyl)cyclopropane-1,1-dicarboxamide;

N-(4-(2,3-dihydro-1H-pyrrolo[2,3-b]pyridin-4-yloxy)-3-fluorophenyl)-N-(4-fluorophenyl)cyclopropane-1,1-dicarboxamide;

N-(4-(3,4-dihydro-2H-pyrido[3,2-b][1,4]oxazin-8-yloxy)-3-fluorophenyl)-N-(4-fluorophenyl)cyclopropane-1,1-dicarboxamide;

N-(4-(3,4-dihydro-2H-pyrido[3,2-b][1,4]oxazin-8-yloxy)phenyl)-N-(4-fluorophenyl)cyclopropane-1,1-dicarboxamide;

N-(3-fluoro-4-(2-oxo-2,3-dihydro-1H-pyrrolo[2,3-b]pyridin-4-yloxy)phenyl)-N-(4-fluorophenyl)cyclopropane-1,1-dicarboxamide;

8-(6-(2-(4-fluorophenylamino)-1-methyl-6-oxo-1,6-dihydropyrimidin-5-yl)pyridin-3-yloxy)-2H-pyrido[3,2-b][1,4]oxazin-3(4H)-one;

5-(5-(2,3-dihydro-1H-pyrrolo[2,3-b]pyridin-4-yloxy)pyridin-2-yl)-2-(4-fluorophenylamino)-3-methylpyrimidin-4(3H)-one;

N-(3-fluoro-4-(3-oxo-3,4-dihydro-2H-pyrido[3,2-b][1,4]oxazin-8-yloxy)phenyl)-1,5-dimethyl-3-oxo-2-phenyl-2,3-dihydro-1H-pyrazole-4-carboxamide;

N-(4-(2,3-dihydro-1H-pyrrolo[2,3-b]pyridin-4-yloxy)-3-fluorophenyl)-1,5-dimethyl-3-oxo-2-phenyl-2,3-dihydro-1H-pyrazole-4-carboxamide;

N-(4-(3,4-dihydro-2H-pyrido[3,2-b][1,4]oxazin-8-yloxy)-3-fluorophenyl)-1,5-dimethyl-3-oxo-2-phenyl-2,3-dihydro-1H-pyrazole-4-carboxamide;

N-(4-(3,4-dihydro-2H-pyrido[3,2-b][1,4]oxazin-8-yloxy)phenyl)-5-(4-fluorophenyl)-4-oxo-1,4-dihydropyridine-3-carboxamide;

5-(4-Fluoro-phenyl)-4-oxo-1,4-dihydro-pyridine-3-carboxylic acid [4-(3,4-dihydro-2H-pyrido[3,2-b][1,4]thiazin-8-yloxy)-3-fluoro-phenyl]-amide;

5-(4-Fluoro-phenyl)-4-oxo-1,4-dihydro-pyridine-3-carboxylic acid [4-(3,4-dihydro-2H-pyrido[3,2-b][1,4]thiazin-8-yloxy)-phenyl]-amide;

1-(4-Fluoro-phenyl)-2-oxo-1,2-dihydro-pyridine-3-carboxylic acid [4-(3,4-dihydro-2H-pyrido[3,2-b][1,4]thiazin-8-yloxy)-3-fluoro-phenyl]-amide;

1-(4-Fluoro-phenyl)-2-oxo-1,2-dihydro-pyridine-3-carboxylic acid [4-(3,4-dihydro-2H-pyrido[3,2-b][1,4]thiazin-8-yloxy)-phenyl]-amide;

Cyclopropane-1,1-dicarboxylic acid [4-(3,4-dihydro-2H-pyrido[3,2-b][1,4]thiazin-8-yloxy)-phenyl]-amide (4-fluoro-phenyl)-amide;

Cyclopropane-1,1-dicarboxylic acid [4-(3,4-dihydro-2H-pyrido[3,2-b][1,4]thiazin-8-yloxy)-3-fluoro-phenyl]-amide (4-fluoro-phenyl)-amide;

5-[5-(3,4-Dihydro-2H-pyrido[3,2-b][1,4]thiazin-8-yloxy)-pyridin-2-yl]-2-(4-fluoro-phenylamino)-3-methyl-3H-pyrimidin-4-one;

5-[5-(3,3-Dimethyl-3,4-dihydro-2H-pyrido[3,2-b][1,4]thiazin-8-yloxy)-pyridin-2-yl]-2-(4-fluoro-phenylamino)-3-methyl-3H-pyrimidin-4-one;

5-(4-Fluoro-phenyl)-4-oxo-1,4-dihydro-pyridine-3-carboxylic acid [4-(3,3-dimethyl-3,4-dihydro-2H-pyrido[3,2-b][1,4]thiazin-8-yloxy)-3-fluoro-phenyl]-amide;

5-(4-Fluoro-phenyl)-4-oxo-1,4-dihydro-pyridine-3-carboxylic acid [4-(3,3-dimethyl-3,4-dihydro-2H-pyrido[3,2-b][1,4]thiazin-8-yloxy)-phenyl]-amide 1-(4-Fluoro-phenyl)-2-oxo-1,2-dihydro-pyridine-3-carboxylic acid [4-(3,3-dimethyl-3,4-dihydro-2H-pyrido[3,2-b][1,4]thiazin-8-yloxy)-3-fluoro-phenyl]-amide;

1-(4-Fluoro-phenyl)-2-oxo-1,2-dihydro-pyridine-3-carboxylic acid [4-(3,3-dimethyl-3,4-dihydro-2H-pyrido[3,2-b][1,4]thiazin-8-yloxy)-phenyl]-amide Cyclopropane-1,1-dicarboxylic acid [4-(3,3-dimethyl-3,4-dihydro-2H-pyrido[3,2-b][1,4]thiazin-8-yloxy)-phenyl]-amide (4-fluoro-phenyl)-amide;

Cyclopropane-1,1-dicarboxylic acid [4-(3,3-dimethyl-3,4-dihydro-2H-pyrido[3,2-b][1,4]thiazin-8-yloxy)-3-fluoro-phenyl]-amide(4-fluoro-phenyl)-amide;

5-[5-(3,3-Dimethyl-3,4-dihydro-2H-pyrido[3,2-b][1,4]oxazin-8-yloxy)-pyridin-2-yl]-2-(4-fluoro-phenylamino)-3-methyl-3H-pyrimidin-4-one;

5-(4-Fluoro-phenyl)-4-oxo-1,4-dihydro-pyridine-3-carboxylic acid [4-(3,3-dimethyl-3,4-dihydro-2H-pyrido[3,2-b][1,4]oxazin-8-yloxy)-3-fluoro-phenyl]-amide;

5-(4-Fluoro-phenyl)-4-oxo-1,4-dihydro-pyridine-3-carboxylic acid [4-(3,3-dimethyl-3,4-dihydro-2H-pyrido[3,2-b][1,4]oxazin-8-yloxy)-phenyl]-amide;

1-(4-Fluoro-phenyl)-2-oxo-1,2-dihydro-pyridine-3-carboxylic acid [4-(3,3-dimethyl-3,4-dihydro-2H-pyrido[3,2-b][1,4]oxazin-8-yloxy)-3-fluoro-phenyl]-amide;

1-(4-Fluoro-phenyl)-2-oxo-1,2-dihydro-pyridine-3-carboxylic acid [4-(3,3-dimethyl-3,4-dihydro-2H-pyrido[3,2-b][1,4]oxazin-8-yloxy)-phenyl]-amide;

Cyclopropane-1,1-dicarboxylic acid [4-(3,3-dimethyl-3,4-dihydro-2H-pyrido[3,2-b][1,4]oxazin-8-yloxy)-phenyl]-amide (4-fluoro-phenyl)-amide;

Cyclopropane-1,1-dicarboxylic acid [4-(3,3-dimethyl-3,4-dihydro-2H-pyrido[3,2-b][1,4]oxazin-8-yloxy)-3-fluoro-phenyl]-amide(4-fluoro-phenyl)-amide;

5-(4-Fluoro-phenyl)-4-oxo-1,4-dihydro-pyridine-3-carboxylic acid [4-(6,7,8,9-tetrahydro-5-thia-1,9-diaza-benzocyclohepten-4-yloxy)-phenyl]-amide;

1-(4-Fluoro-phenyl)-2-oxo-1,2-dihydro-pyridine-3-carboxylic acid [3-fluoro-4-(6,7,8,9-tetrahydro-5-thia-1,9-diaza-benzocyclohepten-4-yloxy)-phenyl]-amide;

Cyclopropane-1,1-dicarboxylic acid (4-fluoro-phenyl)-amide[4-(6,7,8,9-tetrahydro-5-thia-1,9-diaza-benzocyclohepten-4-yloxy)-phenyl]-amide;

Cyclopropane-1,1-dicarboxylic acid (4-fluoro-phenyl)-amide[3-fluoro-4-(6,7,8,9-tetrahydro-5-thia-1,9-diaza-benzocyclohepten-4-yloxy)-phenyl]-amide;

2-(4-Fluoro-phenylamino)-3-methyl-5-[5-(6,7,8,9-tetrahydro-5-thia-1,9-diaza-benzocyclohepten-4-yloxy)-pyridin-2-yl]-3H-pyrimidin-4-one;

5-(4-Fluoro-phenyl)-4-oxo-1,4-dihydro-pyridine-3-carboxylic acid [3-fluoro-4-(6,7,8,9-tetrahydro-5-thia-1,9-diaza-benzocyclohepten-4-yloxy)-phenyl]-amide;

1-(4-Fluoro-phenyl)-2-oxo-1,2-dihydro-pyridine-3-carboxylic acid [4-(6,7,8,9-tetrahydro-5-thia-1,9-diaza-benzocyclohepten-4-yloxy)-phenyl]-amide;

5-(4-Fluoro-phenyl)-4-oxo-1,4-dihydro-pyridine-3-carboxylic acid [3-fluoro-4-(6,7,8,9-tetrahydro-5-oxa-1,9-diaza-benzocyclohepten-4-yloxy)-phenyl]-amide;

1-(4-Fluoro-phenyl)-2-oxo-1,2-dihydro-pyridine-3-carboxylic acid [4-(6,7,8,9-tetrahydro-5-oxa-1,9-diaza-benzocyclohepten-4-yloxy)-phenyl]-amide;

2-(4-Fluoro-phenylamino)-3-methyl-5-[5-(6,7,8,9-tetrahydro-5-oxa-1,9-diaza-benzocyclohepten-4-yloxy)-pyridin-2-yl]-3H-pyrimidin-4-one;

Cyclopropane-1,1-dicarboxylic acid (4-fluoro-phenyl)-amide[3-fluoro-4-(6,7,8,9-tetrahydro-5-oxa-1,9-diaza-benzocyclohepten-4-yloxy)-phenyl]-amide;

Cyclopropane-1,1-dicarboxylic acid (4-fluoro-phenyl)-amide[4-(6,7,8,9-tetrahydro-5-oxa-1,9-diaza-benzocyclohepten-4-yloxy)-phenyl]-amide;

1-(4-Fluoro-phenyl)-2-oxo-1,2-dihydro-pyridine-3-carboxylic acid [3-fluoro-4-(6,7,8,9-tetrahydro-5-oxa-1,9-diaza-benzocyclohepten-4-yloxy)-phenyl]-amide;

5-(4-Fluoro-phenyl)-4-oxo-1,4-dihydro-pyridine-3-carboxylic acid [4-(6,7,8,9-tetrahydro-5-oxa-1,9-diaza-benzocyclohepten-4-yloxy)-phenyl]-amide;

N-(4-(3,4-dimethyl-2,3,4,5-tetrahydropyrido[3,2-b][1,4]oxazepin-9-yloxy)phenyl)-5-(4-fluorophenyl)-4-oxo-1,4-dihydropyridine-3-carboxamide;

1-(4-Fluoro-phenyl)-2-oxo-1,2-dihydro-pyridine-3-carboxylic acid [4-(7,7-dimethyl-6,7,8,9-tetrahydro-5-thia-1,9-diaza-benzocyclohepten-4-yloxy)-phenyl]-amide;

5-(4-Fluoro-phenyl)-4-oxo-1,4-dihydro-pyridine-3-carboxylic acid [4-(3,3-difluoro-2,3-dihydro-1H-pyrrolo[2,3-b]pyridin-4-yloxy)-3-fluoro-phenyl]-amide;

N-(4-(2,2-difluoro-2,3-dihydro-1H-pyrrolo[2,3-b]pyridin-4-yloxy)-3-fluorophenyl)-5-(4-fluorophenyl)-4-oxo-1,4-dihydropyridine-3-carboxamide;

N-(3-fluoro-4-(3-oxo-2,3-dihydro-1H-pyrrolo[2,3-b]pyridin-4-yloxy)phenyl)-1-(4-fluorophenyl)-2-oxo-1,2-dihydropyridine-3-carboxamide;

N-(3-fluoro-5-methyl-4-(2-oxo-2,3-dihydro-1H-pyrrolo[2,3-b]pyridin-4-yloxy)phenyl)-N-(4-fluorophenyl)cyclopropane-1,1-dicarboxamide;

Cyclopropane-1,1-dicarboxylic acid [2,3-difluoro-4-(2-oxo-2,3-dihydro-1H-pyrrolo[2,3-b]pyridin-4-yloxy)-phenyl]-amide(4-fluoro-phenyl)-amide;

3-(4-Fluoro-phenyl)-2-oxo-imidazolidine-1-carboxylic acid [4-(2,3-di-hydro-1H-pyrrolo[2,3-b]pyridin-4-yloxy)-3-fluoro-phenyl]-amide;

3-(4-Fluoro-phenyl)-2-oxo-imidazolidine-1-carboxylic acid [4-(3,4-di-hydro-2H-pyrido[3,2-b][1,4]oxazin-8-yloxy)-3-fluoro-phenyl]-amide;

3-(4-Fluoro-phenyl)-2-oxo-imidazolidine-1-carboxylic acid [4-(3,4-di-hydro-2H-pyrido[3,2-b][1,4]thiazin-8-yloxy)-3-fluoro-phenyl]-amide;

3-(4-Fluoro-phenyl)-2-oxo-imidazolidine-1-carboxylic acid [3-fluoro-4-(6,7,8,9-tetrahydro-5-oxa-1,9-diaza-benzocyclohepten-4-yloxy)-phenyl]-amide;

N-(4-(3',4'-dihydrospiro[cyclopropane-1,2'-pyrido[3,2-b][1,4]oxazine]-8'-yloxy)-3-fluorophenyl)-5-(4-fluorophenyl)-4-oxo-1,4-dihydropyridine-3-carboxamide;

N-(3-fluoro-4-(2-(hydroxymethyl)-3,4-dihydro-2H-pyrido[3,2-b][1,4]oxazin-8-yloxy)phenyl)-5-(4-fluorophenyl)-4-oxo-1,4-dihydropyridine-3-carboxamide;

8-(2-fluoro-4-(5-(4-fluorophenyl)-4-oxo-1,4-dihydro-pyridine-3-carboxamido)phenoxy)-3,4-dihydro-2H-pyrido[3,2-b][1,4]oxazine-2-carboxamide;

N-(4-(2-(aziridin-1-ylmethyl)-3,4-dihydro-2H-pyrido[3,2-b][1,4]oxazin-8-yloxy)-3-fluorophenyl)-5-(4-fluorophenyl)-4-oxo-1,4-dihydropyridine-3-carboxamide;

N-(3-fluoro-4-(3-(2-hydroxyethyl)-2,3-dihydro-1H-pyrrolo[2,3-b]pyridin-4-yloxy)phenyl)-5-(4-fluorophenyl)-4-oxo-1,4-dihydropyridine-3-carboxamide; or
N-(3-fluoro-4-(2'-oxo-1',2'-dihydrospiro[cyclopropane-1, 3'-pyrrolo[2,3-b]pyridine]-4'-yloxy)phenyl)-5-(4-fluorophenyl)-4-oxo-1,4-dihydropyridine-3-carboxamide.

The present invention also provides a pharmaceutical composition comprising at least one compound described herein and at least one pharmaceutically acceptable excipient, such as hydroxypropyl methyl cellulose. In the composition, the weight ratio of the compound to the excipient can be within the range of, e.g., from about 0.0001 to about 10.

The present invention additionally provided a use of the pharmaceutical composition described herein for the preparation of a medicament.

In some embodiments, a medicament thus prepared can be used for the treatment or prevention of cancer, cancer metastasis, cardiovascular disease, an immunological disorder or an ocular disorder.

In some embodiments, a medicament thus prepared can be used for delaying or preventing disease progression in cancer, cancer metastasis, cardiovascular disease, an immunological disorder or an ocular disorder.

In some embodiments, a medicament thus prepared can be used for treating or delaying the progression or onset of cancer, cancer metastasis, cardiovascular disease, an immunological disorder or an ocular disorder.

In some embodiments, a medicament thus prepared can be used for the treatment or prevention of cancer, cancer metastasis, cardiovascular disease, an immunological disorder or an ocular disorder.

In some embodiments, a medicament thus prepared can be used for delaying or preventing disease progression in cancer, cancer metastasis, cardiovascular disease, an immunological disorder or an ocular disorder.

In some embodiments, a medicament thus prepared can be used for treating or delaying the progression or onset of cancer, cancer metastasis, cardiovascular disease, an immunological disorder or an ocular disorder.

In some embodiments, a medicament thus prepared can be used as an inhibitor of c-Met.

In addition, the present invention provides at least one compound for use in the treatment of cancer, the prevention of cancer metastasis or the treatment of cardiovascular disease, an immunological disorder or an ocular disorder.

The present invention also provides a method of treating a patient having a condition which is mediated by protein kinase activity, said method comprising administering to the patient a therapeutically effective amount of at least one compound as described herein, or a pharmaceutically acceptable salt thereof. Examples of the protein kinase include KDR, Tie-2, Flt3, FGFR3, AbI, Aurora A, c-Src, IGF-IR, ALK, c-MET, RON, PAK1, PAK2, and TAK1.

In some embodiments, the condition mediated by protein kinase activity is cancer.

Examples of cancer include a solid tumor, a sarcoma, fibrosarcoma, osteoma, melanoma, retinoblastoma, a rhabdomyosarcoma, glioblastoma, neuroblastoma, teratocarcinoma, hematopoietic malignancy, and malignant ascites.

Also provided is at least one compound as described herein or a pharmaceutically acceptable salt thereof for use as a medicament.

Further provided is at least one compound as described herein or a pharmaceutically acceptable salt thereof for use in the treatment of cancer.

Additionally provided is a method of treating cancer selected from the group consisting of lung cancer, breast cancer, colorectal cancer, renal cancer, pancreatic cancer, head cancer, neck cancer, hereditary papillary renal cell carcinoma, childhood hepatocellular carcinoma, and gastric cancer in a mammal comprising administering to a mammal in need of such treatment an effective amount of at least one compound described herein or a pharmaceutically acceptable salt thereof.

In another aspect, the present invention is directed to a method of treating a patient suffering from c-Met tyrosine kinase-mediated disorders, comprising the step of administering to said patient a therapeutically effective amount of the compound of the above compound.

The term "halogen", as used herein, unless otherwise indicated, means fluoro, chloro, bromo or iodo. The preferred halogen groups include F, Cl and Br.

As used herein, unless otherwise indicated, alkyl includes saturated monovalent hydrocarbon radicals having straight, branched or cyclic moieties. For example, alkyl radicals include methyl, ethyl, propyl, isopropyl, cyclopropyl, n-butyl, isobutyl, sec-butyl, t-butyl, cyclobutyl, n-pentyl, 3-(2-methyl) butyl, 2-pentyl, 2-methylbutyl, neopentyl, cyclcopentyl, n-hexyl, 2-hexyl, 2-methylpentyl and cyclohexyl. Similarly, $C_{1-8}$, as in $C_{1-8}$alkyl is defined to identify the group as having 1, 2, 3, 4, 5, 6, 7 or 8 carbon atoms in a linear or branched arrangement.

Alkenyl and alkynyl groups include straight, branched chain or cyclic alkenes and alkynes. Likewise, "$C_{2-8}$ alkenyl" and "$C_{2-8}$ alkynyl" means an alkenyl or alkynyl radicals having 2, 3, 4, 5, 6, 7 or 8 carbon atoms in a linear or branched arrangement.

Alkoxy radicals are oxygen ethers formed from the previously described straight, branched chain or cyclic alkyl groups.

The term "aryl", as used herein, unless otherwise indicated, refers to an unsubstituted or substituted mono- or polycyclic ring system containing carbon ring atoms. The preferred aryls are mono cyclic or bicyclic 6-10 membered aromatic ring systems. Phenyl and naphthyl are preferred aryls. The most preferred aryl is phenyl.

The term "heterocyclyl", as used herein, unless otherwise indicated, represents an unsubstituted or substituted stable three to eight membered monocyclic saturated ring system which consists of carbon atoms and from one to three heteroatoms selected from N, O or S, and wherein the nitrogen or sulfur heteroatoms may optionally be oxidized, and the nitrogen heteroatom may optionally be quaternized. The heterocyclyl group may be attached at any heteroatom or carbon atom which results in the creation of a stable structure. Examples of such heterocyclyl groups include, but are not limited to azetidinyl, pyrrolidinyl, piperidinyl, piperazinyl, oxopiperazinyl, oxopiperidinyl, oxoazepinyl, azepinyl, tetrahydrofuranyl, dioxolanyl, tetrahydroimidazolyl, tetrahydrothiazolyl, tetrahydrooxazolyl, tetrahydropyranyl, morpholinyl, thiomorpholinyl, thiamorpholinyl sulfoxide, thiamorpholinyl sulfone and oxadiazolyl.

The term "heteroaryl", as used herein, unless otherwise indicated, represents an unsubstituted or substituted stable five or six membered monocyclic aromatic ring system or an unsubstituted or substituted nine or ten membered benzofused heteroaromatic ring system or bicyclic heteroaromatic ring system which consists of carbon atoms and from one to four heteroatoms selected from N, O or S, and wherein the nitrogen or sulfur heteroatoms may optionally be oxidized, and the nitrogen heteroatom may optionally be quaternized. The heteroaryl group may be attached at any heteroatom or carbon atom which results in the creation of a stable structure. Examples of heteroaryl groups include, but are not limited to thienyl, furanyl, imidazolyl, isoxazolyl, oxazolyl, pyrazolyl, pyrrolyl, thiazolyl, thiadiazolyl, triazolyl, pyridyl, pyridazinyl, indolyl, azaindolyl, indazolyl, benzimidazolyl, benzofuranyl, benzothienyl, benzisoxazolyl, benzoxazolyl, benzopyrazolyl, benzothiazolyl, benzothiadiazolyl, benzotriazolyl adeninyl, quinolinyl or isoquinolinyl.

The term "carbonyl" refers to the group C(O).

The term "alkoxycarbonyl" refers to straight or branched chain esters of a carboxylic acid derivative of the present invention of the number of carbon atoms specified (e.g., $C_{1-6}$ alkoxycarbonyl), or any number within this range (e.g., methyloxycarbonyl(MeOCO—), ethyloxycarbonyl, or butyloxycarbonyl).

Whenever the term "alkyl" or "aryl" or either of their prefix roots appear in a name of a substituent (e.g., aralky or dialkylamino) it shall be interpreted as including those limitations given above for "alkyl" and "aryl." Designated numbers of carbon atoms (e.g., $C_{1-6}$) shall refer independently to the number of carbon atoms in an alkyl moiety or to the alkyl portion of a larger substituent in which alkyl appears as its prefix root.

The term "alkylsulphinyl" refers to straight or branched chain alkylsulfoxides of the number of carbon atoms specified (e.g., $C_{1-6}$ alkylsulfinyl), or any number within this range (e.g., methylsulphinyl (MeSO—), ethylsulphinyl, isopropylsulphinyl).

The term "alkylsulphonyl" refers to straight or branched chain alkylsulfones of the number of carbon atoms specified (e. g., $C_{1-6}$ alkylsulphonyl), or any number within this range [e. g, methylsulphonyl (MeSO$_2$—), ethylsulphonyl, isopropylsulphonyl, etc].

The term "alkylthio" refers to straight or branched chain alkylsulfides of the number of carbon atoms specified (e. g., $C_{1-6}$ alkylthio), or any number within this range [e.g., methylthio (MeS—), ethylthio, isopropylthio, etc].

The term "alkenyloxy" refers to the group —O-alkenyl, where alkenyl is defined as above.

The term "alknyloxy" refers to the group —O-alknyl, where alknyl is defined as above.

The term "composition", as used herein, is intended to encompass a product comprising the specified ingredients in the specified amounts, as well as any product which results, directly or indirectly, from combinations of the specified ingredients in the specified amounts. Accordingly, pharmaceutical compositions containing the compounds of the present invention as the active ingredient as well as methods of preparing the instant compounds are also part of the present invention. Furthermore, some of the crystalline forms for the compounds may exist as polymorphs and as such are intended to be included in the present invention. In addition, some of the compounds may form solvates with water (i.e., hydrates) or common organic solvents and such solvates are also intended to be encompassed within the scope of this invention.

The compounds of the present invention may also be present in the form of pharmaceutically acceptable salts. For use in medicine, the salts of the compounds of this invention refer to non-toxic "pharmaceutically acceptable salts". The pharmaceutically acceptable salt forms include pharmaceutically acceptable acidic/anionic or basic/cationic salts. The pharmaceutically acceptable acidic/anionic salt generally takes a form in which the basic nitrogen is protonated with an inorganic or organic acid. Representative organic or inorganic acids include hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic. Pharmaceutically acceptable basic/cationic salts include, and are not limited to aluminum, calcium, chloroprocaine, choline, diethanolamine, ethylenediamine, lithium, magnesium, potassium, sodium and zinc.

The present invention includes within its scope the prodrugs of the compounds of this invention. In general, such prodrugs will be functional derivatives of the compounds that are readily converted in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "Design of Prodrugs", ed. H. Bundgaard, Elsevier, 1985.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques know in the art as well as those methods set forth herein.

The present invention includes compounds described can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof.

The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

When a tautomer of the compound of Formula (I) exists, the present invention includes any possible tautomers and pharmaceutically acceptable salts thereof, and mixtures thereof, except where specifically stated otherwise.

When the compound of Formula (I) and pharmaceutically acceptable salts thereof exist in the form of solvates or polymorphic forms, the present invention includes any possible solvates and polymorphic forms. A type of a solvent that forms the solvate is not particularly limited so long as the solvent is pharmacologically acceptable. For example, water, ethanol, propanol, acetone or the like can be used.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, formic, hydrochloric, maleic, phosphoric, sulfuric and tartaric acids. Particularly preferred are formic and hydrochloric acid. Since the compounds of Formula (I) are intended for pharmaceutical use they are preferably provided in substantially pure form, for example at least 60% pure, more suitably at least 75% pure, especially at least 98% pure (% are on a weight for weight basis).

The pharmaceutical compositions of the present invention comprise a compound represented by Formula I (or a pharmaceutically acceptable salt thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I, or a prodrug, or a metabolite, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound represented by Formula I, or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound, or a pharmaceutically acceptable salt, of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen. In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient. For example, a formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or a pharmaceutically acceptable salt thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including antioxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

Generally, dosage levels on the order of from about 0.01 mg/kg to about 150 mg/kg of body weight per day are useful in the treatment of the above-indicated conditions, or alternatively about 0.5 mg to about 7 g per patient per day. For example, inflammation, cancer, psoriasis, allergy/asthma, disease and conditions of the immune system, disease and conditions of the central nervous system (CNS), may be effectively treated by the administration of from about 0.01 to 50 mg of the compound per kilogram of body weight per day, or alternatively about 0.5 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

These and other aspects will become apparent from the following written description of the invention.

MODES FOR CARRYING OUT THE INVENTION

The present invention is directed to novel compounds having c-Met inhibitory activity. The compounds of the invention include those of Formula I and pharmaceutically acceptable salts, solvates, chelates, non-covalent complexes, or prodrugs thereof.

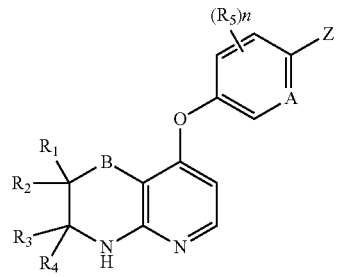

In Formula I,

B is absent, O, S, $OCH_2$, or $SCH_2$;

$R_1$, $R_2$, $R_3$ and $R_4$ are each independently hydrogen, halogen, substituted or unsubstituted $C_{1-6}$alkyl, substituted or unsubstituted $C_{2-8}$alkenyl, substituted or unsubstituted $C_{2-8}$alkynyl, substituted or unsubstituted aryl, substituted or unsubstituted heteroaryl, substituted or unsubstituted heterocyclyl, $C_{1-8}$alkanoyl, ($C_{1-8}$alkoxy)carbonyl, $C_{1-8}$alkylsulphinyl, $C_{1-8}$alkylsulphonyl, arylsulphonyl, —CN, —$NO_2$, hydroxy, amino, carboxy, oxo, carbamoyl, $C_{1-8}$alkoxy, $C_{2-8}$alkenyloxy, $C_{2-8}$alkynyloxy, $C_{1-8}$alkylthio, N—($C_{1-8}$alkyl)carbamoyl, N,N-di($C_{1-8}$alkyl)carbamoyl, $C_{1-8}$alkanoyloxy, $C_{1-8}$alkanoylamino, $C_{3-8}$alkynoylamino, N—($C_{1-8}$alkyl)sulphamoyl, or N,N-di($C_{1-8}$alkyl)sulphamoyl; or $R_1$ and $R_2$ together, or $R_3$ and $R_4$ together, form =O;

A is N or CH;

n is 0, 1, 2, or 3;

each $R_5$ is independently halogen, substituted or unsubstituted $C_{1-6}$alkyl, —CN, —$NO_2$, —$OR_{50}$, —$N(R_{50})_2$, —$S(O)_{0-2}R_{50}$, or —$C(O)R_{50}$;

each $R_{50}$ is independently hydrogen or substituted or unsubstituted $C_{1-6}$alkyl;

Z is $NHR_6$ or of Formula II:

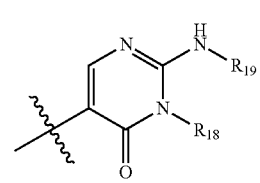

wherein $R_{18}$ and $R_{19}$ are each independently hydrogen, substituted or unsubstituted $C_{1-8}$alkyl, substituted or unsubstituted $C_{2-8}$alkenyl, substituted or unsubstituted $C_{2-8}$alkynyl, substituted or unsubstituted aryl, substituted or unsubstituted heteroaryl, substituted or unsubstituted heterocyclyl, $C_{1-8}$alkanoyl, ($C_{1-8}$alkoxy)carbonyl, $C_{1-8}$alkylsulphinyl, $C_{1-8}$alkylsulphonyl, or arylsulphonyl;

$R_6$ is of Formula III, IV, V, VI, or VII:

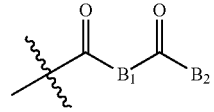

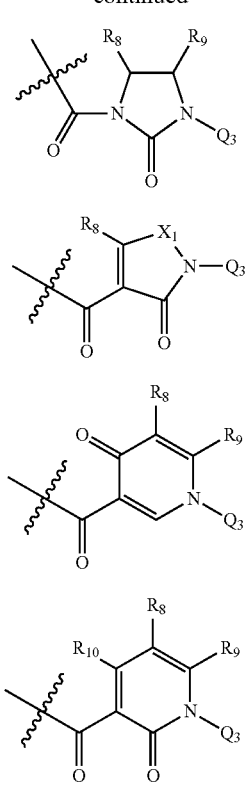

wherein:
B$_1$ is

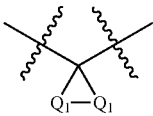

wherein each Q$_1$ is independently C(R$_7$)$_2$;

B$_2$ is NHQ$_2$ and Q$_2$ is substituted or unsubstituted aryl, substituted or unsubstituted heteroaryl, substituted or unsubstituted heterocyclyl, substituted or unsubstituted (C$_{1-8}$alkyl)aryl, substituted or unsubstituted (C$_{1-8}$alkyl)heteroaryl, or substituted or unsubstituted (C$_{1-8}$alkyl)heterocyclyl; or B$_1$ and B$_2$, together with the carbonyl group therebetween, form a 5- to 10-membered substituted or unsubstituted heteroaryl, or substituted or unsubstituted heterocyclyl;

Q$_3$ is hydrogen, substituted or unsubstituted aryl, substituted or unsubstituted alkyl, substituted or unsubstituted heteroaryl, substituted or unsubstituted heterocyclyl, substituted or unsubstituted (C$_{1-8}$alkyl)aryl, substituted or unsubstituted (C$_{1-8}$alkyl)heteroaryl, or substituted or unsubstituted (C$_{1-8}$alkyl)heterocyclyl;

X$_1$ is NR$_8$ or CR$_8$R$_9$;

R$_7$, R$_8$, R$_9$ and R$_{10}$ are each independently hydrogen, halogen, substituted or unsubstituted C$_{1-8}$alkyl, substituted or unsubstituted C$_{2-8}$alkenyl, substituted or unsubstituted C$_{2-8}$alkynyl, substituted or unsubstituted aryl, substituted or unsubstituted heteroaryl, substituted or unsubstituted heterocyclyl, C$_{1-8}$alkanoyl, (C$_{1-8}$alkoxy)carbonyl, C$_{1-8}$alkylsulphinyl, C$_{1-8}$alkylsulphonyl, arylsulphonyl, —CN, —NO$_2$, hydroxy, amino, carboxy, oxo, carbamoyl, C$_{1-8}$alkoxy, C$_{2-8}$alkenyloxy, C$_{2-8}$alknyloxy, C$_{1-8}$alkylthio, N—(C$_{1-8}$alkyl)carbamoyl, N,N-di(C$_{1-8}$alkyl)carbamoyl, C$_{1-8}$alkanoyloxy, C$_{1-8}$alkanoylamino, C$_{3-8}$alkynoylamino, N—(C$_{1-8}$alkyl)sulphamoyl, N,N-di(C$_{1-8}$alkyl)sulphamoyl, substituted or unsubstituted C$_{1-8}$alkylaryl, substituted or unsubstituted C$_{1-8}$alkylheteroaryl, or substituted or unsubstituted C$_{1-8}$alkylheterocyclyl.

The flowing compounds of the invention are provided to give the reader an understanding of the compounds encompassed by the invention:

N-(4-(2,3-dihydro-1H-pyrrolo[2,3-b]pyridin-4-yloxy)-3-fluorophenyl)-5-(4-fluorophenyl)-4-oxo-1,4-dihydropyridine-3-carboxamide;

N-(3-fluoro-4-(3-oxo-3,4-dihydro-2H-pyrido[3,2-b][1,4]oxazin-8-yloxy)phenyl)-5-(4-fluorophenyl)-4-oxo-1,4-dihydropyridine-3-carboxamide;

N-(4-(3,4-dihydro-2H-pyrido[3,2-b][1,4]oxazin-8-yloxy)-3-fluorophenyl)-5-4-(fluorophenyl)-4-oxo-1,4-dihydropyridine-3-carboxamide;

N-(4-(3,4-dihydro-2H-pyrido[3,2-b][1,4]oxazin-8-yloxy)phenyl)-5-(4-fluorophenyl)-4-oxo-1,4-dihydropyridine-3-carboxamide;

N-(3-fluoro-4-(2-oxo-2,3-dihydro-1H-pyrrolo[2,3-b]pyridin-4-yloxy)phenyl)-5-(4-fluorophenyl)-4-oxo-1,4-dihydropyridine-3-carboxamide;

N-(3-fluoro-4-(3-oxo-3,4-dihydro-2H-pyrido[3,2-b][1,4]oxazin-8-yloxy)phenyl)-1-(4-fluorophenyl)-2-oxo-1,2-dihydropyridine-3-carboxamide;

N-(4-(2,3-dihydro-1H-pyrrolo[2,3-b]pyridin-4-yloxy)-3-fluorophenyl)-1-(4-fluorophenyl)-2-oxo-1,2-dihydropyridine-3-carboxamide;

N-(4-(3,4-dihydro-2H-pyrido[3,2-b][1,4]oxazin-8-yloxy)-3-fluorophenyl)-1-(4-fluorophenyl)-2-oxo-1,2-dihydropyridine-3-carboxamide;

N-(4-(3,4-dihydro-2H-pyrido[3,2-b][1,4]oxazin-8-yloxy)phenyl)-1-(4-fluorophenyl)-2-oxo-1,2-dihydropyridine-3-carboxamide;

N-(3-fluoro-4-(2-oxo-2,3-dihydro-1H-pyrrolo[2,3-b]pyridin-4-yloxy)phenyl)-1-(4-fluorophenyl)-2-oxo-1,2-dihydropyridine-3-carboxamide;

N-(3-fluoro-4-(3-oxo-3,4-dihydro-2H-pyrido[3,2-b][1,4]oxazin-8-yloxy)phenyl)-N-(4-fluorophenyl)cyclopropane-1,1-dicarboxamide;

N-(4-(2,3-dihydro-1H-pyrrolo[2,3-b]pyridin-4-yloxy)-3-fluorophenyl)-N-(4-fluorophenyl)cyclopropane-1,1-dicarboxamide;

N-(4-(3,4-dihydro-2H-pyrido[3,2-b][1,4]oxazin-8-yloxy)-3-fluorophenyl)-N-(4-fluorophenyl)cyclopropane-1,1-dicarboxamide;

N-(4-(3,4-dihydro-2H-pyrido[3,2-b][1,4]oxazin-8-yloxy)phenyl)-N-(4-fluorophenyl)cyclopropane-1,1-dicarboxamide;

N-(3-fluoro-4-(2-oxo-2,3-dihydro-1H-pyrrolo[2,3-b]pyridin-4-yloxy)phenyl)-N-(4-fluorophenyl)cyclopropane-1,1-dicarboxamide;

8-(6-(2-(4-fluorophenylamino)-1-methyl-6-oxo-1,6-dihydropyrimidin-5-yl)pyridin-3-yloxy)-2H-pyrido[3,2-b][1,4]oxazin-3(4H)-one;

5-(5-(2,3-dihydro-1H-pyrrolo[2,3-b]pyridin-4-yloxy)pyridin-2-yl)-2-(4-fluorophenylamino)-3-methylpyrimidin-4(3H)-one;

N-(3-fluoro-4-(3-oxo-3,4-dihydro-2H-pyrido[3,2-b][1,4]oxazin-8-yloxy)phenyl)-1,5-dimethyl-3-oxo-2-phenyl-2,3-dihydro-1H-pyrazole-4-carboxamide;

N-(4-(2,3-dihydro-1H-pyrrolo[2,3-b]pyridin-4-yloxy)-3-fluorophenyl)-1,5-dimethyl-3-oxo-2-phenyl-2,3-dihydro-1H-pyrazole-4-carboxamide;

N-(4-(3,4-dihydro-2H-pyrido[3,2-b][1,4]oxazin-8-yloxy)-3-fluorophenyl)-1,5-dimethyl-3-oxo-2-phenyl-2,3-dihydro-1H-pyrazole-4-carboxamide;

N-(4-(3,4-dihydro-2H-pyrido[3,2-b][1,4]oxazin-8-yloxy)phenyl)-5-(4-fluorophenyl)-4-oxo-1,4-dihydropyridine-3-carboxamide;

5-(4-Fluoro-phenyl)-4-oxo-1,4-dihydro-pyridine-3-carboxylic acid [4-(3,4-dihydro-2H-pyrido[3,2-b][1,4]thiazin-8-yloxy)-3-fluoro-phenyl]-amide;

5-(4-Fluoro-phenyl)-4-oxo-1,4-dihydro-pyridine-3-carboxylic acid [4-(3,4-dihydro-2H-pyrido[3,2-b][1,4]thiazin-8-yloxy)-phenyl]-amide;

1-(4-Fluoro-phenyl)-2-oxo-1,2-dihydro-pyridine-3-carboxylic acid [4-(3,4-dihydro-2H-pyrido[3,2-b][1,4]thiazin-8-yloxy)-3-fluoro-phenyl]-amide;

1-(4-Fluoro-phenyl)-2-oxo-1,2-dihydro-pyridine-3-carboxylic acid [4-(3,4-dihydro-2H-pyrido[3,2-b][1,4]thiazin-8-yloxy)-phenyl]-amide;

Cyclopropane-1,1-dicarboxylic acid [4-(3,4-dihydro-2H-pyrido[3,2-b][1,4]thiazin-8-yloxy)-phenyl]-amide (4-fluoro-phenyl)-amide;

Cyclopropane-1,1-dicarboxylic acid [4-(3,4-dihydro-2H-pyrido[3,2-b][1,4]thiazin-8-yloxy)-3-fluoro-phenyl]-amide (4-fluoro-phenyl)-amide;

5-[5-(3,4-Dihydro-2H-pyrido[3,2-b][1,4]thiazin-8-yloxy)-pyridin-2-yl]-2-(4-fluoro-phenylamino)-3-methyl-3H-pyrimidin-4-one;

5-[5-(3,3-Dimethyl-3,4-dihydro-2H-pyrido[3,2-b][1,4]thiazin-8-yloxy)-pyridin-2-yl]-2-(4-fluoro-phenylamino)-3-methyl-3H-pyrimidin-4-one;

5-(4-Fluoro-phenyl)-4-oxo-1,4-dihydro-pyridine-3-carboxylic acid [4-(3,3-dimethyl-3,4-dihydro-2H-pyrido[3,2-b][1,4]thiazin-8-yloxy)-3-fluoro-phenyl]-amide;

5-(4-Fluoro-phenyl)-4-oxo-1,4-dihydro-pyridine-3-carboxylic acid [4-(3,3-dimethyl-3,4-dihydro-2H-pyrido[3,2-b][1,4]thiazin-8-yloxy)-phenyl]-amide 1-(4-Fluoro-phenyl)-2-oxo-1,2-dihydro-pyridine-3-carboxylic acid [4-(3,3-dimethyl-3,4-dihydro-2H-pyrido[3,2-b][1,4]thiazin-8-yloxy)-3-fluoro-phenyl]-amide;

1-(4-Fluoro-phenyl)-2-oxo-1,2-dihydro-pyridine-3-carboxylic acid [4-(3,3-dimethyl-3,4-dihydro-2H-pyrido[3,2-b][1,4]thiazin-8-yloxy)-phenyl]-amide Cyclopropane-1,1-dicarboxylic acid [4-(3,3-dimethyl-3,4-dihydro-2H-pyrido[3,2-b][1,4]thiazin-8-yloxy)-phenyl]-amide (4-fluoro-phenyl)-amide;

Cyclopropane-1,1-dicarboxylic acid [4-(3,3-dimethyl-3,4-dihydro-2H-pyrido[3,2-b][1,4]thiazin-8-yloxy)-3-fluoro-phenyl]-amide(4-fluoro-phenyl)-amide;

5-[5-(3,3-Dimethyl-3,4-dihydro-2H-pyrido[3,2-b][1,4]oxazin-8-yloxy)-pyridin-2-yl]-2-(4-fluoro-phenylamino)-3-methyl-3H-pyrimidin-4-one;

5-(4-Fluoro-phenyl)-4-oxo-1,4-dihydro-pyridine-3-carboxylic acid [4-(3,3-dimethyl-3,4-dihydro-2H-pyrido[3,2-b][1,4]oxazin-8-yloxy)-3-fluoro-phenyl]-amide;

5-(4-Fluoro-phenyl)-4-oxo-1,4-dihydro-pyridine-3-carboxylic acid [4-(3,3-dimethyl-3,4-dihydro-2H-pyrido[3,2-b][1,4]oxazin-8-yloxy)-phenyl]-amide;

1-(4-Fluoro-phenyl)-2-oxo-1,2-dihydro-pyridine-3-carboxylic acid [4-(3,3-dimethyl-3,4-dihydro-2H-pyrido[3,2-b][1,4]oxazin-8-yloxy)-3-fluoro-phenyl]-amide;

1-(4-Fluoro-phenyl)-2-oxo-1,2-dihydro-pyridine-3-carboxylic acid [4-(3,3-dimethyl-3,4-dihydro-2H-pyrido[3,2-b][1,4]oxazin-8-yloxy)-phenyl]-amide;

Cyclopropane-1,1-dicarboxylic acid [4-(3,3-dimethyl-3,4-dihydro-2H-pyrido[3,2-b][1,4]oxazin-8-yloxy)-phenyl]-amide (4-fluoro-phenyl)-amide;

Cyclopropane-1,1-dicarboxylic acid [4-(3,3-dimethyl-3,4-dihydro-2H-pyrido[3,2-b][1,4]oxazin-8-yloxy)-3-fluoro-phenyl]-amide(4-fluoro-phenyl)-amide;

5-(4-Fluoro-phenyl)-4-oxo-1,4-dihydro-pyridine-3-carboxylic acid [4-(6,7,8,9-tetrahydro-5-thia-1,9-diaza-benzocyclohepten-4-yloxy)-phenyl]-amide;

1-(4-Fluoro-phenyl)-2-oxo-1,2-dihydro-pyridine-3-carboxylic acid [3-fluoro-4-(6,7,8,9-tetrahydro-5-thia-1,9-diaza-benzocyclohepten-4-yloxy)-phenyl]-amide;

Cyclopropane-1,1-dicarboxylic acid (4-fluoro-phenyl)-amide[4-(6,7,8,9-tetrahydro-5-thia-1,9-diaza-benzocyclohepten-4-yloxy)-phenyl]-amide;

Cyclopropane-1,1-dicarboxylic acid (4-fluoro-phenyl)-amide[3-fluoro-4-(6,7,8,9-tetrahydro-5-thia-1,9-diaza-benzocyclohepten-4-yloxy)-phenyl]-amide;

2-(4-Fluoro-phenylamino)-3-methyl-5-[5-(6,7,8,9-tetrahydro-5-thia-1,9-diaza-benzocyclohepten-4-yloxy)-pyridin-2-yl]-3H-pyrimidin-4-one;

5-(4-Fluoro-phenyl)-4-oxo-1,4-dihydro-pyridine-3-carboxylic acid [3-fluoro-4-(6,7,8,9-tetrahydro-5-thia-1,9-diaza-benzocyclohepten-4-yloxy)-phenyl]-amide;

1-(4-Fluoro-phenyl)-2-oxo-1,2-dihydro-pyridine-3-carboxylic acid [4-(6,7,8,9-tetrahydro-5-thia-1,9-diaza-benzocyclohepten-4-yloxy)-phenyl]-amide;

5-(4-Fluoro-phenyl)-4-oxo-1,4-dihydro-pyridine-3-carboxylic acid [3-fluoro-4-(6,7,8,9-tetrahydro-5-oxa-1,9-diaza-benzocyclohepten-4-yloxy)-phenyl]-amide;

1-(4-Fluoro-phenyl)-2-oxo-1,2-dihydro-pyridine-3-carboxylic acid [4-(6,7,8,9-tetrahydro-5-oxa-1,9-diaza-benzocyclohepten-4-yloxy)-phenyl]-amide;

2-(4-Fluoro-phenylamino)-3-methyl-5-[5-(6,7,8,9-tetrahydro-5-oxa-1,9-diaza-benzocyclohepten-4-yloxy)-pyridin-2-yl]-3H-pyrimidin-4-one;

Cyclopropane-1,1-dicarboxylic acid (4-fluoro-phenyl)-amide[3-fluoro-4-(6,7,8,9-tetrahydro-5-oxa-1,9-diaza-benzocyclohepten-4-yloxy)-phenyl]-amide;

Cyclopropane-1,1-dicarboxylic acid (4-fluoro-phenyl)-amide[4-(6,7,8,9-tetrahydro-5-oxa-1,9-diaza-benzocyclohepten-4-yloxy)-phenyl]-amide;

1-(4-Fluoro-phenyl)-2-oxo-1,2-dihydro-pyridine-3-carboxylic acid [3-fluoro-4-(6,7,8,9-tetrahydro-5-oxa-1,9-diaza-benzocyclohepten-4-yloxy)-phenyl]-amide;

5-(4-Fluoro-phenyl)-4-oxo-1,4-dihydro-pyridine-3-carboxylic acid [4-(6,7,8,9-tetrahydro-5-oxa-1,9-diaza-benzocyclohepten-4-yloxy)-phenyl]-amide;

N-(4-(3,4-dimethyl-2,3,4,5-tetrahydropyrido[3,2-b][1,4]oxazepin-9-yloxy)phenyl)-5-(4-fluorophenyl)-4-oxo-1,4-dihydropyridine-3-carboxamide;

1-(4-Fluoro-phenyl)-2-oxo-1,2-dihydro-pyridine-3-carboxylic acid [4-(7,7-dimethyl-6,7,8,9-tetrahydro-5-thia-1,9-diaza-benzocyclohepten-4-yloxy)-phenyl]-amide;

5-(4-Fluoro-phenyl)-4-oxo-1,4-dihydro-pyridine-3-carboxylic acid [4-(3,3-difluoro-2,3-dihydro-1H-pyrrolo[2,3-b]pyridin-4-yloxy)-3-fluoro-phenyl]-amide;

N-(4-(2,2-difluoro-2,3-dihydro-1H-pyrrolo[2,3-b]pyridin-4-yloxy)-3-fluorophenyl)-5-(4-fluorophenyl)-4-oxo-1,4-dihydropyridine-3-carboxamide;

N-(3-fluoro-4-(3-oxo-2,3-dihydro-1H-pyrrolo[2,3-b]pyridin-4-yloxy)phenyl)-1-(4-fluorophenyl)-2-oxo-1,2-dihydropyridine-3-carboxamide;

N-(3-fluoro-5-methyl-4-(2-oxo-2,3-dihydro-1H-pyrrolo[2,3-b]pyridin-4-yloxy)phenyl)-N-(4-fluorophenyl)cyclopropane-1,1-dicarboxamide;

Cyclopropane-1,1-dicarboxylic acid [2,3-difluoro-4-(2-oxo-2,3-dihydro-1H-pyrrolo[2,3-b]pyridin-4-yloxy)-phenyl]-amide(4-fluoro-phenyl)-amide;

3-(4-Fluoro-phenyl)-2-oxo-imidazolidine-1-carboxylic acid [4-(2,3-di-hydro-1H-pyrrolo[2,3-b]pyridin-4-yloxy)-3-fluoro-phenyl]-amide;
3-(4-Fluoro-phenyl)-2-oxo-imidazolidine-1-carboxylic acid [4-(3,4-di-hydro-2H-pyrido[3,2-b][1,4]oxazin-8-yloxy)-3-fluoro-phenyl]-amide;
3-(4-Fluoro-phenyl)-2-oxo-imidazolidine-1-carboxylic acid [4-(3,4-di-hydro-2H-pyrido[3,2-b][1,4]thiazin-8-yloxy)-3-fluoro-phenyl]-amide;
3-(4-Fluoro-phenyl)-2-oxo-imidazolidine-1-carboxylic acid [3-fluoro-4-(6,7,8,9-tetrahydro-5-oxa-1,9-diaza-benzocyclohepten-4-yloxy)-phenyl]-amide;
N-(4-(3',4'-dihydrospiro[cyclopropane-1,2'-pyrido[3,2-b][1,4]oxazine]-8'-yloxy)-3-fluorophenyl)-5-(4-fluoro-phenyl)-4-oxo-1,4-dihydropyridine-3-carboxamide;
N-(3-fluoro-4-(2-(hydroxymethyl)-3,4-dihydro-2H-pyrido[3,2-b][1,4]oxazin-8-yloxy)phenyl)-5-(4-fluoro-phenyl)-4-oxo-1,4-dihydropyridine-3-carboxamide;
8-(2-fluoro-4-(5-(4-fluorophenyl)-4-oxo-1,4-dihydro-pyridine-3-carboxamido)phenoxy)-3,4-dihydro-2H-pyrido[3,2-b][1,4]oxazine-2-carboxamide;
N-(4-(2-(aziridin-1-ylmethyl)-3,4-dihydro-2H-pyrido[3,2-b][1,4]oxazin-8-yloxy)-3-fluorophenyl)-5-(4-fluoro-phenyl)-4-oxo-1,4-dihydropyridine-3-carboxamide;
N-(3-fluoro-4-(3-(2-hydroxyethyl)-2,3-dihydro-1H-pyrrolo[2,3-b]pyridin-4-yloxy)phenyl)-5-(4-fluorophenyl)-4-oxo-1,4-dihydropyridine-3-carboxamide; and
N-(3-fluoro-4-(2'-oxo-1',2'-dihydrospiro[cyclopropane-1,3'-pyrrolo[2,3-b]pyridine]-4'-yloxy)phenyl)-5-(4-fluorophenyl)-4-oxo-1,4-dihydropyridine-3-carboxamide.

As defined herein, the term "subject" or "patient" refers to an animal, preferably a mammal, most preferably a human, who has been the object of treatment, observation or experiment. The term "therapeutically effective amounts used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

The term "substituted", as defined herein, includes multiple substituents (e.g., Phe, aryl, heteroaryl), preferably from one to five substituents, more preferably from one to three substituents, most preferably from one to two substituents, independently selected from the list of substituents. Typical substituents include, but are not limited to, —X, —CH$_3$, —C$_2$H$_5$, —OH, =O, —SH, =S, —NH$_2$, —CX$_3$, —CF$_3$, —CN, —NO$_2$, —OS(O$_2$)OH, —C(O)OH, where each X is independently a halogen. The term "substituted" specifically envisions and allows for substitutions that are common in the art. However, it is generally understood by those skilled in the art that the substituents should be selected so as to not adversely affect the pharmacological characteristics of the compound or adversely interfere with the use of the medicament.

The compounds of the present invention may have asymmetric carbon atoms. Such diasteromeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomric mixture by reaction with an appropriate optically active compound (e. g., alcohol), separating the diastereomers and converting (e. g., hydrolyzing) the individual diastereomers to the corresponding pure enantiomers. All such isomers, including diastereomer mixtures and pure enantiomers are considered as part of the invention.

In general, the compounds of the present invention can be prepared according to Scheme 1 depicts general synthetic routes for compounds of the invention and are not intended to be limiting. More specifically, Scheme 1 depicts synthesis of fused pyridine compounds. Specific examples are described subsequently to these general synthetic descriptions so as to allow one skilled in the art to make and use either quinazolines or quinolines of the invention.

Scheme 1 outlines the general procedures one could use to provide compounds of the present invention, for example Z is NHR$_6$ in formula I.

Scheme 1

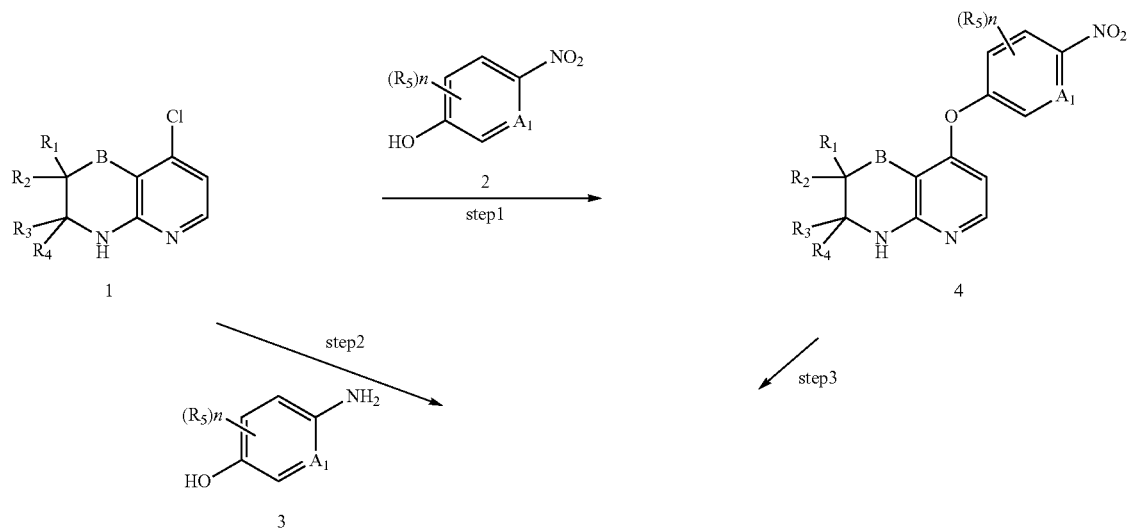

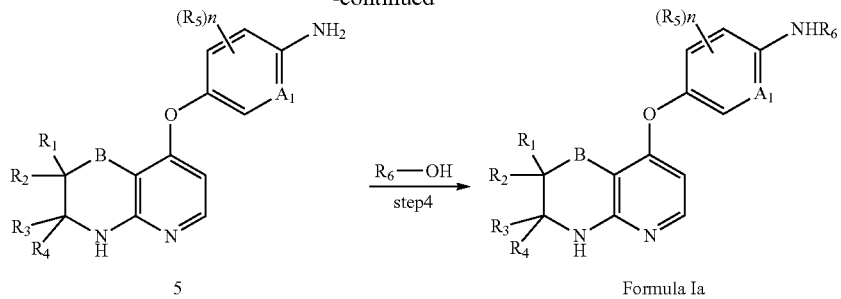

5      Formula Ia

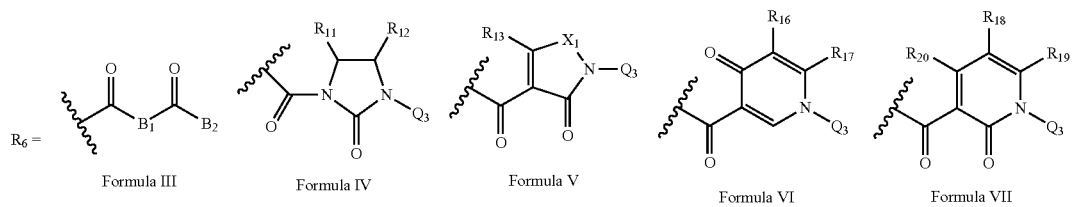

Formula III    Formula IV    Formula V    Formula VI    Formula VII

The compounds of formula I of present invention, Z is $NHR_6$ in formula I can be prepared from intermediates 5 and suitable acid compounds, $R_6$—OH, where $R_6$ is defined above, using standard coupling reaction condition for amide formation. Suitable acid compounds, $R_6$—OH, where $R_6$ is defined above, are commercial available, known in the literature or may be conveniently prepared by a variety methods familiar to those skilled in the art.

One common route for intermediates 5 is illustrated in Scheme 1. Compounds 1 can react with intermediate 2 at elevated temperature, in the present of a suitable base such as sodium bicarbonate in a proper solvent such as DMF, followed by standard nitro group reduction, to provides the intermediates 5. Alternate route for the preparation of intermediates 5 may be the substitution reaction of compounds 1 with aniline intermediate 3 in elevated temperature in the present of a suitable base such as sodium bicarbonate in a proper solvent such as DMF, as shown in Scheme 1.

Scheme 2 outlines the general procedures one could use to provide compounds of the present invention, for example Z is groups in formula II.

Scheme 2

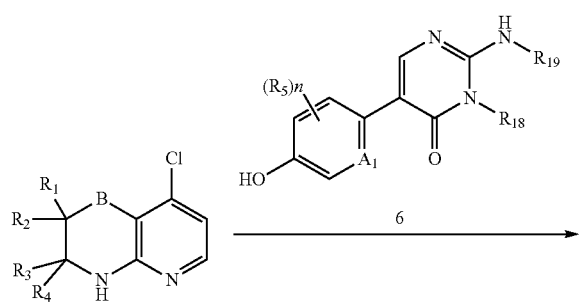

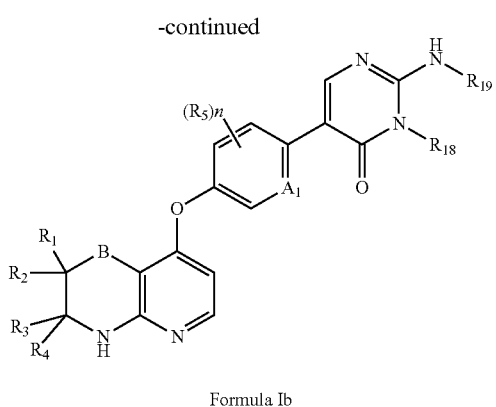

Formula Ib

Suitable intermediates 6, where $R_{18}$ and $R_{19}$ are defined above, are commercial available, known in the literature or may be conveniently prepared by a variety methods familiar to those skilled in the art. Intermediates 6 can react with Compounds 1 at elevated temperature, in the present of a suitable base such as sodium bicarbonate in a proper solvent such as DMF, to provides compounds of the present invention, for example Z is groups in formula II.

To prepare the pharmaceutical compositions of this invention, one or more compounds of Formula (I) or salt thereof as the active ingredient, is intimately admixed with a pharmaceutical carrier according to conventional pharmaceutical compounding techniques, which carrier may take a wide variety of forms depending of the form of preparation desired for administration (e. g. oral or parenteral). Suitable pharmaceutically acceptable carriers are well known in the art. Descriptions of some of these pharmaceutically acceptable carriers may be found in The Handbook of Pharmaceutical Excipients, published by the American Pharmaceutical Association and the Pharmaceutical Society of Great Britain During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known in the art.

Administration of the active compounds can be effected by any method which enables delivery of the compounds to the site of action (e. g., cancer cells). These methods include oral routes, rectal routes, intraduodenal routes, parenteral injection (including intravenous, subcutaneous, intramuscular, intravascular or infusion), topical administration, etc. The amount of active compound administered will, of course, be dependent on the subject being treated, on the severity of the affliction, on the manner of administration and on the judgement of the prescribing physician. However an effective dosage is in the range of approximately 0.001 mg to about 300 mg (preferably, from about 0.01 mg to about 100 mg; and, more preferably, from about 0.1 mg to about 30 mg) and may be given at a dosage of from about 0.001 mg/kg/day to about 300 mg/kg/day (preferably, from about 0.01 mg/kg/day to about 100 mg/kg/day; and, more preferably, from about 0.1 mg/kg/day to about 30 mg/kg/day).

The composition may, for example, be in a form suitable for oral administration such as a tablet, capsule, pill, powder, sustained release formulation, solution, or suspension; for parenteral injection such as a sterile solution, suspension or emulsion; or for topical administration such as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the present invention as an active ingredient. In addition, it may include other medicinal or pharmaceutical agents, carriers, adjuvants, etc.

Exemplary parenteral administration forms include solutions or suspensions of active compounds in sterile aqueous solutions, for example aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes.

Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

The therapeutic compounds may also be administered to a mammal other than a human. The dosage to be administered to a mammal will depend on the animal species and the disease or disorder being treated. The therapeutic compounds may be administered to animals in the form of a capsule, bolus, tablet or liquid drench. The therapeutic compounds may also be administered to animals by injection or as an implant. Such formulations are prepared in a conventional manner in accordance with standard veterinary practice. As an alternative the therapeutic compounds may be administered with the animal feedstuff and for this purpose a concentrated feed additive or premix may be prepared for mixing with the normal animal feed.

An example of use of the invention is a method of treating a epidermal growth factor receptor (EGFR) tyrosine kinase or vascular endothelial growth factor receptor (VEGFR) tyrosine kinase mediated disorder in a subject in need thereof comprising administering to the subject a therapeutically effective amount of any of the compounds or pharmaceutical compositions described above. In a preferred embodiment, the method relates to the treatment of cancer such as brain, lung, squamous cell, bladder, gastric, pancreatic, breast, head, neck, oesophageal, prostate, colorectal, gynecological or thyroid cancer.

EXAMPLES

The following Examples are provided to better illustrate the present invention. All parts and percentages are by weight and all temperatures are degrees Celsius, unless explicitly stated otherwise. The following abbreviations have been used in the examples:
ATP: Adenosine triphosphate;
DIPEA: N,N-Diisopropylethylamine;
DMF: N,N-Dimethylformamide;
DMA: N,N-Dimethyacetamide;
DMAP: 4-N,N-Dimethylamiopryidine;
DMSO: Dimethyl sulfoxide;
DEAD: Diethyl azodicarboxylate;
HATU: O-(7-Azabenzotriazol-1-yl)-N,N,N',N'-tetramethyluronium hexafluorophosphate;
DIPEA: N,N-Diisopropylethylamine;
EDC: 1-ethyl-3-(3-dimethylaminopropyl)carbodiimide;
TBAB: Tetrabutyl ammonium bromide;
TEA: Triethylamine;
EtOAc: Ethyl acetate;
GSR: Glutathione-S-Transferase;
Crk: CT10 (Chicken Tumor Retrovirus 10);
min: Minute;
h or hr: Hour;
rt or RT: room temperature;
SDS, Sodium Dodecyl Sulfate;
SDS-PAGE, Sodium Dodecyl Sulfate PolyAcrylamide Electrophoresis Gel;
TLC, Thin layer chromatography.

EXAMPLES

Example 1

N-(4-(2,3-dihydro-1H-pyrrolo[2,3-b]pyridin-4-yloxy)-3-fluorophenyl)-5-(4-fluorophenyl)-4-oxo-1,4-dihydropyridine-3-carboxamide (Product 1)

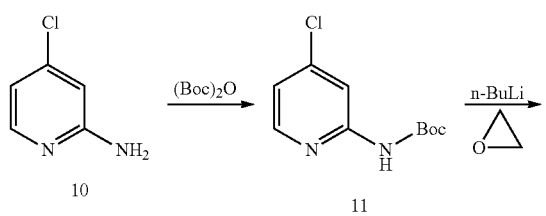

29
-continued

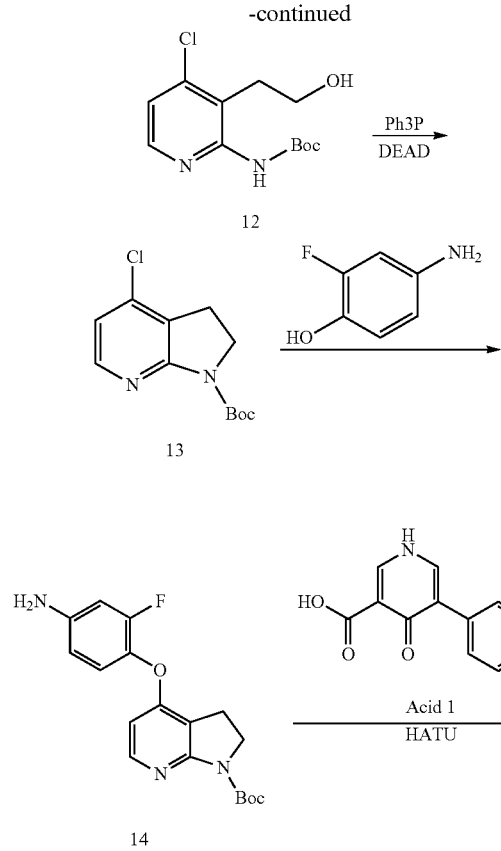

30
Step 0. Preparation of Acid1

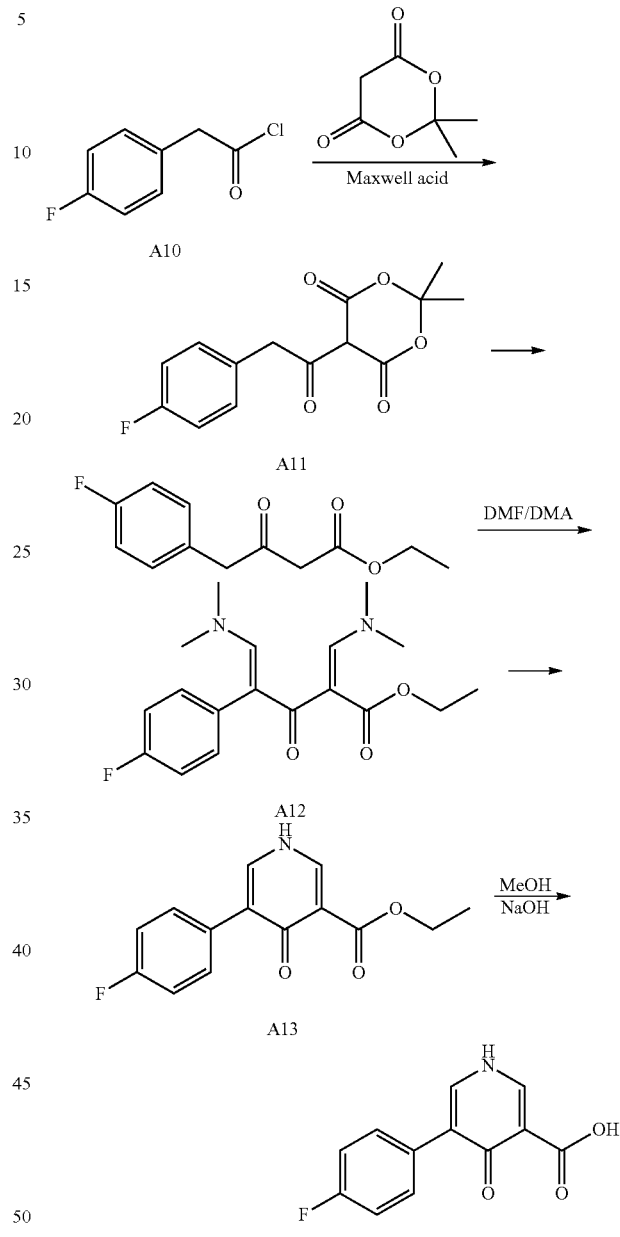

1. Preparation of A11

Pyridine (70.35 g) was added to the mixture of Maxwell acid (50.32 g) in DCM (450 ml) with stirring, followed by the addition of A10 (62.28 g) at 0° C. The reaction was continued at 0 V for 2.5 hrs or till the reaction is completed monitored by TLC. The reaction mixture was diluted with stirring by DCM (300 ml) and 750 ml 1N HCl. The organic phase was separated and dried by vacuum to give solid, A11 (66.70 g).

2. Preparation of A12

A11 (66.70 g) in ethanol (400 ml) was heated to 87° C. and stirred overnight. The reaction mixture was cooled and

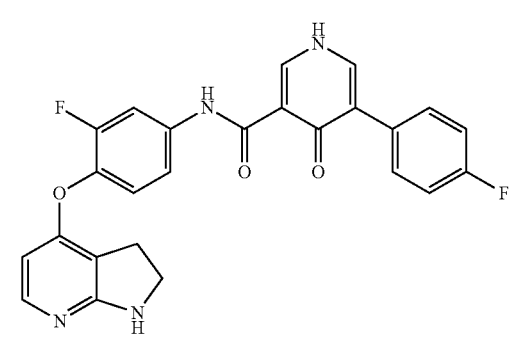

concentrated in vacuum to give an oil (55 g). The oily residue was dissolved in DMF/DMA (200 ml), heated to 110° C. for 3 hrs, and then concentrated in vacuum, followed by dilution with ethyl acetate and stirring. The precipitate was collected by filtration to yield A12 (52 g).

3. Preparation of A13

A12 (27.20 g) was dissolved in ethanol (600 ml) and to which NH$_4$Cl was added. The reaction mixture was heated to reflux for 2 hrs, and then cooled to room temperature. Solid was collected by filtration to yield A13 (16.88 g).

4. Preparation of Acid1

2N NaOH solution (120 ml) was added to A13 (16.88 g) in ethanol (50 ml). The reaction mixture was stirred and heated to 65° C. for 2 hrs, and then cooled to room temperature. The reaction mixture was added in 1.5N HCl (400 ml) to precipitate out solid. Filtration was to collect solid. The solid was wash twice with water, and dried by vacuum to give Acid1 (14.13 g).

Step 1. Preparation of tert-butyl 4-chloropyridin-2-ylcarbamate (Compound 11)

Compound 10 (4-chloropyridin-2-amine, 128 g, 1 mol) was dissolved in DCM (3.0 L), to which was added TEA (121 g, 1.2 mol) and DMAP (9.76 g, 0.08 mol) with stirring. After the mixture was stirred at 15° C.-20° C. for several minutes, to which the reaction mixture was slowly added (Boc)$_2$O (229 g) in DCM (500 ml) at 15 V-20V. The reaction was continued below 25 V until completion. The precipitate was collected by filtration and washed with DCM (500 ml). The final compound 11 was purified by recrystallization with ethyl acetate to yield compound 11 (160 g).

Step 2. Preparation of tert-butyl 4-chloro-3-(2-hydroxyethyl)pyridin-2-ylcarbamate (Compound 12)

Compound 11 (2.01 g, 8.80 mmol) in THF (15 ml) was cooled to −78 V, then to which dropwise added n-BuLi (12 ml, 19.26 mmol). The reaction mixture was warmed to −70° C. and kept another half hour. Ethylene oxide (1.93 g, 43.75 mmol) was added to the reaction mixture at −70° C. and stirred overnight to warm to room temperature. The reaction was quenched with water (1 ml) and extracted by ethyl acetate (100 ml) and brine (100 ml). The organic layer was separated and dried. Concentration of the organic layer gave compound 12 as yellow solid (2.0 g).

Step 3. Preparation of tert-butyl 4-chloro-2,3-dihydro-1H-pyrrolo[2,3-b]pyridine-1-carboxylate (Compound 13)

The compound 12 (1.37 g, 5.04 mmol) was dissolved in THF (20 ml), to which was added Ph$_3$P (1.59 g, 6.05 mmol). DEAD (1.07 g, 6.06 mmol) was dropwise added to the reaction mixture at 0° C., and then slowly warmed to room temperature. After concentration the reaction mixture was purified by silica gel column to yield compound 13 as white solid (1.15 g).

Step 4. Preparation of Compound 14

Compound 13 (1.15 g, 4.53 mmol) and 4-amino-2-fluorophenol (1.15 g, 9.06 mmol) was dissolved in DMF (20 ml), then to which was added Cesium carbonate (4.43 g, 13.59 mmol). The reaction mixture was heated to 125° C. overnight. After cooled down room temperature the reaction mixture was diluted with ethyl acetate. The organic phase was collected and evaporated in vacuum to give compound 14 as solid (0.80 g).

Step 5. Preparation of Compound 15

Compound 14 (4.00 g, 11.6 mmol) and Acid1 (2.97 g, 12.8 mmol) was dissolved in DCM (60 ml) followed by the addition of HATU (5.29 g, 13.9 mmol) and TEA (3.52 g, 34.8 mmol). The reaction was stirred at room temperature overnight, and then diluted with ethyl acetate and water. The organic phase was separated and aqueous layer was extracted by ethyl acetate. All organic layer was combined and dried. After evaporation of solvent the residue was purified by gel column to compound 15 as light yellow solid (4.8 g).

Step 6. Preparation of Product 1

Compound 15 (3.5 g) was added in the mixture of DCM (15 ml) and trifluoroacetic acid (15 ml), the reaction was continued for 3 hrs at room temperature. The reaction mixture was evaporated in vacuum to give product 1 as light red solid (2.46 g). MS: 461 (M+H)$^+$. HNMR (DMSO-d$_6$): 13.14 (s, 1H), 12.68 (s, 1H), 8.62 (s, 1H), 8.09 (s, 1H), 7.96-8.00 (dd, 1H, J=9.60 Hz 1.80 Hz), 7.68-7.72 (m, 2H), 7.61-7.62 (d, 1H, J=4.50 Hz), 7.39-7.42 (dd, 1H, J=6.60 Hz 1.20 Hz), 7.20-7.29 (m, 3H), 6.48 (s, 1H), 5.90-5.91 (d, 1H, J=4.50 Hz), 3.45-3.49 (m, 2H), 2.83-2.89 (m, 2H).

Example 2

N-(3-fluoro-4-(3-oxo-3,4-dihydro-2H-pyrido[3,2-b][1,4]oxazin-8-yloxy)phenyl)-5-(4-fluorophenyl)-4-oxo-1,4-dihydropyridine-3-carboxamide (Product 2)

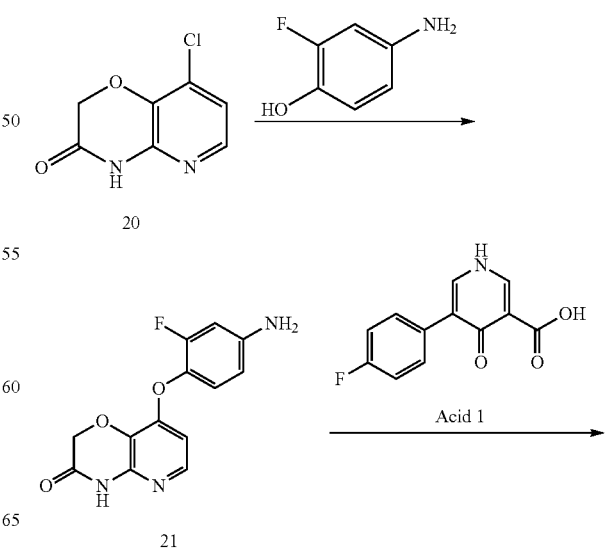

33

-continued

Product 2

Step 1. Preparation of Compound 21

The compound 20 (184 mg, 1.0 mmol), 2-fluoro-4-aminophenol (190 mg, 1.5 mmol) and cesium carbonate (652 mg, 2.0 mmol) were mixed in N-methyl pyrrolidone (3 ml). The reaction mixture was heated 180° C. overnight under $N_2$. Then, the reaction mixture was added in water (50 ml) and extracted by ethyl acetate (100 ml). The organic phase was washed with brine, dried, and concentrated, followed by purification of flash column to give compound 21 (105 mg).

Step 2. Preparation of Product 2

HATU (76 mg, 0.2 mmol), DIPEA (26 mg, 0.2 mmol), and Acid1 (25.6 mg, 0.11 mmol) were mixed in DCM (3 ml) at 0° C. and stirred for 15 min, followed by the addition of compound 21 (27 mg, 0.1 mmol). The reaction mixture was stirred for 4 hrs at room temperature. After concentration the reaction mixture was purified by flash column to give product 2 (16 mg). MS: 491 (M+H)$^+$.

Example 3

N-(4-(3,4-dihydro-2H-pyrido[3,2-b][1,4]oxazin-8-yloxy)-3-fluorophenyl)-5-(4-fluorophenyl)-4-oxo-1,4-dihydropyridine-3-carboxamide (Product 3)

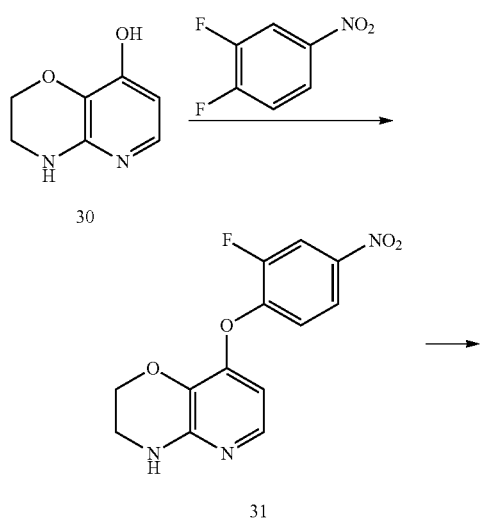

34

-continued

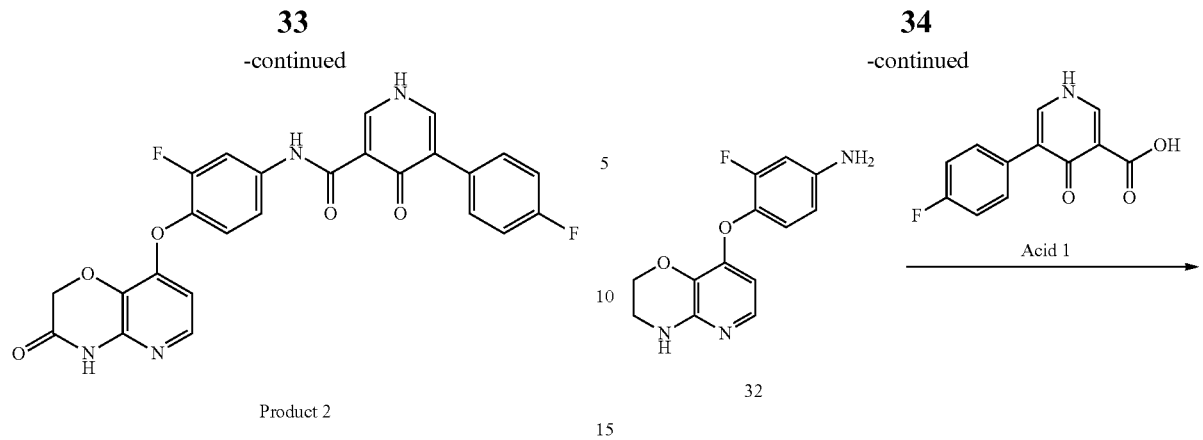

Product 3

Step 1. Preparation of Compound 31

The compound 30 (1.52 g, 10mmol), 3,4-difluoronitrobenzene (1.75 g, 11mmol) and cesium carbonate (3.60 g, 11mmol) were mixed in DMF (15 ml) and stirred at room temperature overnight. After completion monitored by TLC, the reaction mixture was added in water (400 ml) and extracted by ethyl acetate (800 ml). The aqueous layer was extracted by ethyl acetate. All organic layer was combined and washed with brine, dried. After concentration the residue was purified by flash column to compound 31 (2.20 g).

Step 2. Preparation of Compound 32

The compound 31 (2.20 g) was added to the mixture of 5% Pd/C (0.8 g) and methanol (100 ml). The resulting mixture was stirred under $H_2$ until that was no starting material. Then, the reaction mixture was filtrated to remove Pd/C. The filtrate was concentrated to give compound 32 (1.60 g).

Step 3. Preparation of Product 3

The desired product 3 is synthesized by using the similar sequence and conditions as described for Example 2. MS: 477 (M+H)$^+$.

Example 4

N-(4-(3,4-dihydro-2H-pyrido[3,2-b][1,4]oxazin-8-yloxy)phenyl)-5-(4-fluorophenyl)-4-oxo-1,4-dihydropyridine-3-carboxamide (Product 4)

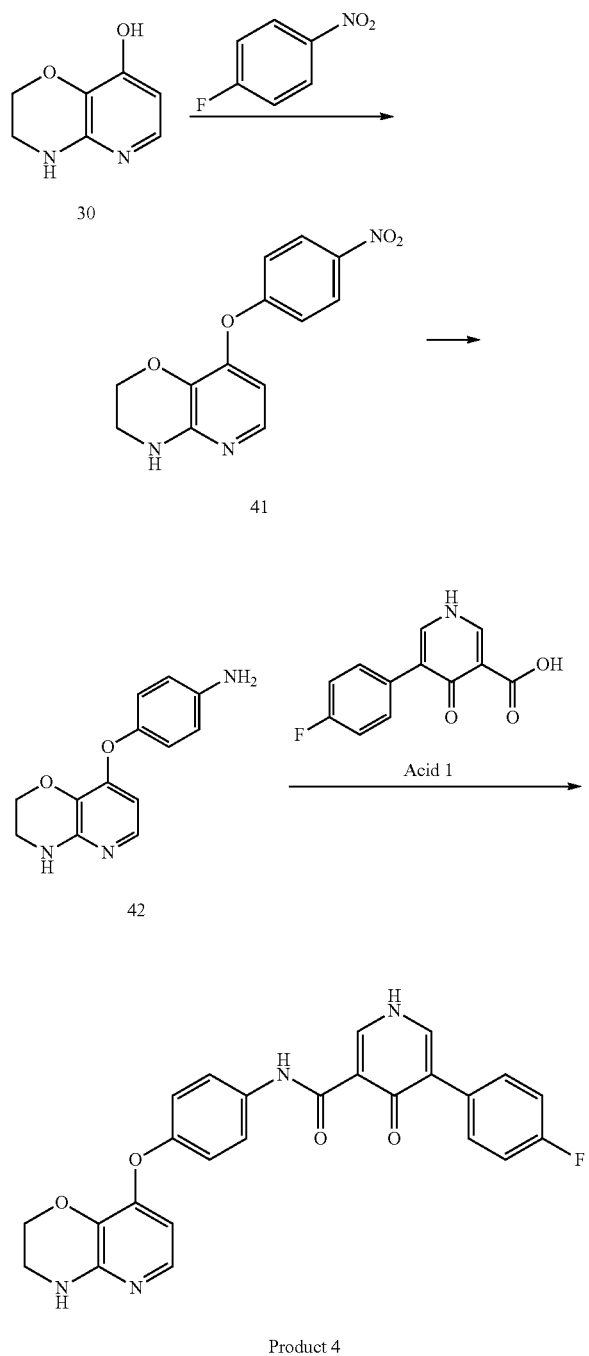

Example 5

N-(3-fluoro-4-(2-oxo-2,3-dihydro-1H-pyrrolo[2,3-b]pyridin-4-yloxy)phenyl)-5-(4-fluorophenyl)-4-oxo-1,4-dihydropyridine-3-carboxamide (Product 5)

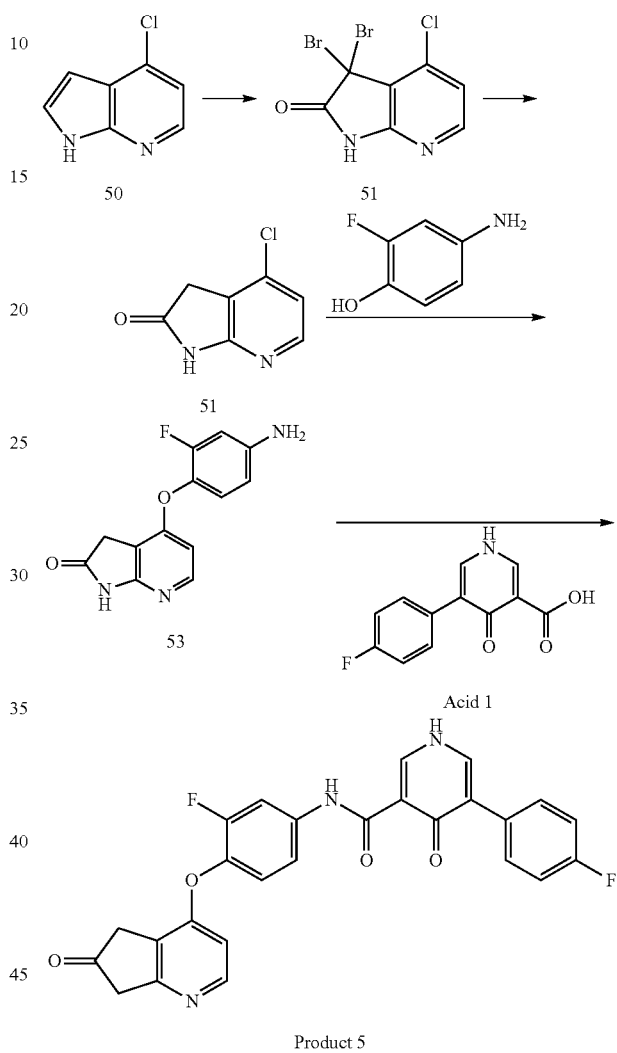

The desired compound 42 is synthesized by using the similar sequence and conditions as described for Example 3.

The desired product 4 is synthesized by using the similar sequence and conditions as described for Example 2. MS: 459 (M+H)⁺.

Step 1. Preparation of Compound 51

Compound 50 (3.0 g 20 mmol) was dissolved in tert-butyl alcohol (200 ml), to which pyridinium tribromide (21.5 g 67 mmol was added. The reaction mixture was stirred at room temperature overnight, followed by concentration in vacuum. The residue was purified by extraction and recrystallization to give compound 51 (3.60 g).

Step 2. Preparation of Compound 52

Compound 51 (3.6 g) was dissolved in alcohol (50 ml), to which acetic acid (2.0 ml) was added slowly. The reaction was heated to reflux till completion. Filtration of the reaction mixture was employed to remove the solid and the filtrate was concentrated in vacuum to give compound 52 (1.12 g).

Step 3. Preparation of Compound 53

Compound 52 (1.12 g, 66 mmol), fluoro-4-aminophenol (930 mg, 73 mmol) and cesium carbonate (4.30 mg, 132 mmol) was mixed in DMSO (15 ml) and heated to 135° C. overnight under N₂. The reaction mixture was diluted with ethyl acetate and water. The organic layer was separated and dried. Evaporation of the organic layer gave compound 53 (660 mg).

Step 4. Preparation of Product 5

The desired product 5 is synthesized by using the similar sequence and conditions as described for Example 2. MS: 475 (M+H)$^+$.

Example 6

N-(3-fluoro-4-(3-oxo-3,4-dihydro-2H-pyrido[3,2-b][1,4]oxazin-8-yloxy)phenyl)-1-(4-fluorophenyl)-2-oxo-1,2-dihydropyridine-3-carboxamide (Product 6)

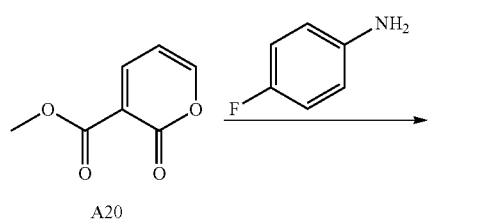

A20

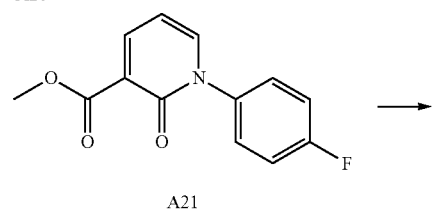

A21

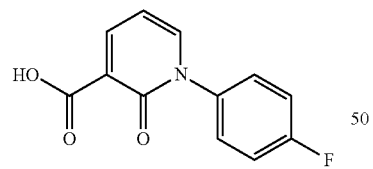

Acid 2

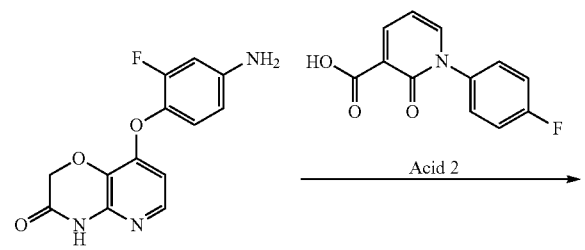

21

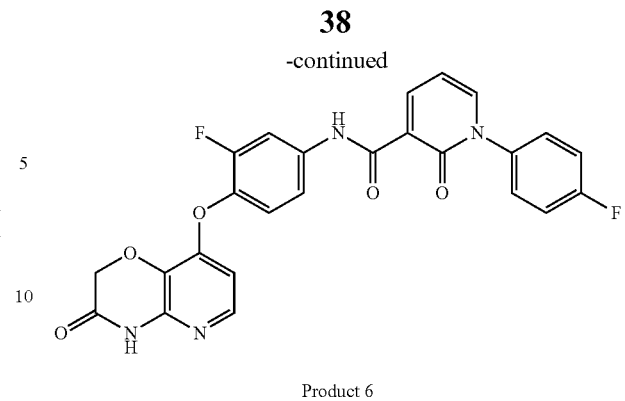

Product 6

Step 1. Preparation of A21

A20 (3.10 g) was dissolved in DMF (25 ml) and cooled to 0V, to which 4-fluoroaniline was added. The reaction was continued for 7 hrs at 0 V, followed by the addition of EDC.HCl (5.40 g) and DMAP (0.61 g) and stirred overnight. The reaction mixture was diluted by water and ethyl acetate. The organic layer was separated and washed by brine. After dried, the solvent was removed by evaporation to give A21 (2.80 g).

Step 2. Preparation of Acid2

A21 (2.61 g) was mixed in NaOH solution (1.60 g NaOH and 40 ml water) and methanol (8 ml). Then the reaction mixture was stirred and heated to reflux for 1hr. After cooled to room temperature the reaction mixture was adjusted to pH=1. The resulting solid was collected by filtration and washed by water, followed by drying to give Acid2 (2.25 g).

Step 3. Preparation of Product 6

The desired product 6 is synthesized by using the similar sequence and conditions as described for Example 2 with Acid2 instead of Acid1. MS: 491 (M+H)$^+$.

Example 7

N-(4-(2,3-dihydro-1H-pyrrolo[2,3-b]pyridin-4-yloxy)-3-fluorophenyl)-1-(4-fluorophenyl)-2-oxo-1,2-dihydropyridine-3-carboxamide (Product 7)

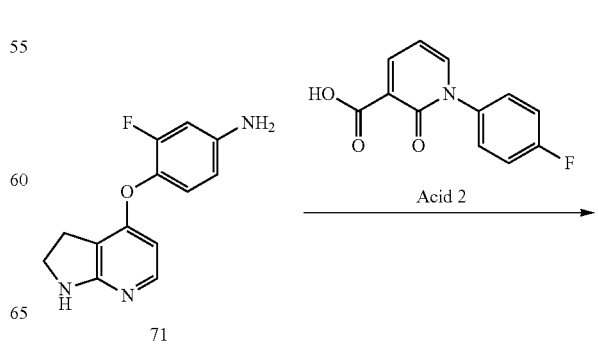

71

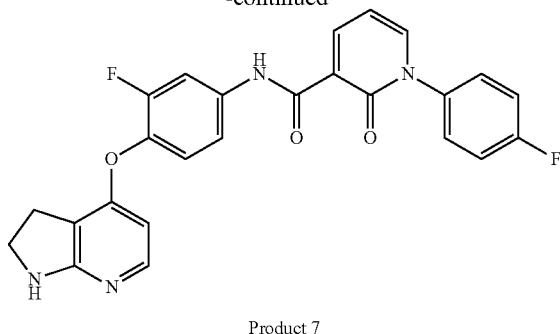

Product 7

The compound 71was obtained by compound 14 was off Boc's protection.

The desired product 7 is synthesized by using the similar sequence and conditions as described for Example 2 with Acid2 instead of Acid1. MS: 461 (M+H)⁺. HNMR (DMSO-$d_6$): 12.10 (s, 1H), 8.57-8.59 (dd, 1H, J=5.40 Hz 1.50 Hz), 8.13-8.15 (dd, 1H, J=5.10 Hz 1.80 Hz), 7.99-8.03 (dd, 1H, J=9.60 Hz 1.65 Hz), 7.60-7.64 (m, 4H), 7.41-7.49 (m, 3H), 7.31-7.36 (t, 1H, J=13.50 Hz), 6.72-6.75 (t, 1H, J=10.20 Hz), 6.10-6.11 (d, 1H, J=5.10 Hz), 3.62-3.66 (m, 2H), 2.89-2.93 (m, 2H).

Example 8

N-(4-(3,4-dihydro-2H-pyrido[3,2-b][1,4]oxazin-8-yloxy)-3-fluorophenyl)-1-(4-fluorophenyl)-2-oxo-1,2-dihydropyridine-3-carboxamide (Product 8)

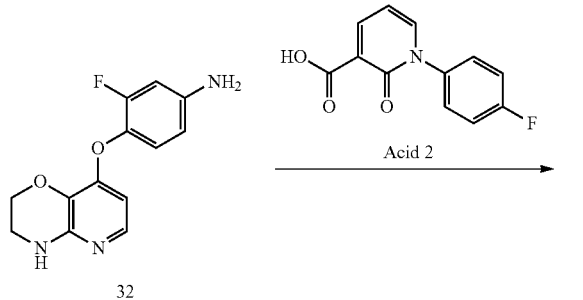

Product 8

The desired product 8 is synthesized by using the similar sequence and conditions as described for Example 2 with Acid2 instead of Acid1. MS: 477 (M+H)⁺. HNMR (DMSO-$d_6$): 12.03 (s, 1H), 8.56-8.59 (dd, 1H, J=5.40 Hz 1.65 Hz), 8.11-8.13 (dd, 1H, J=4.80 Hz 1.50 Hz), 7.93-7.97 (dd, 1H, J=9.90 Hz 1.80 Hz), 7.60-7.62 (m, 2H), 7.40-7.46 (m, 4H), 7.12-7.16 (t, 1H, J=13.80 Hz), 6.81 (s, 1H), 6.70-6.74 (t, 1H, J=10.50 Hz), 6.00 (ms, 1H), 4.11-4.16 (m, 2H), 3.41-3.42 (m, 2H).

Example 9

N-(4-(3,4-dihydro-2H-pyrido[3,2-b][1,4]oxazin-8-yloxy)phenyl)-1-(4-fluorophenyl)-2-oxo-1,2-dihydropyridine-3-carboxamide (Product 9)

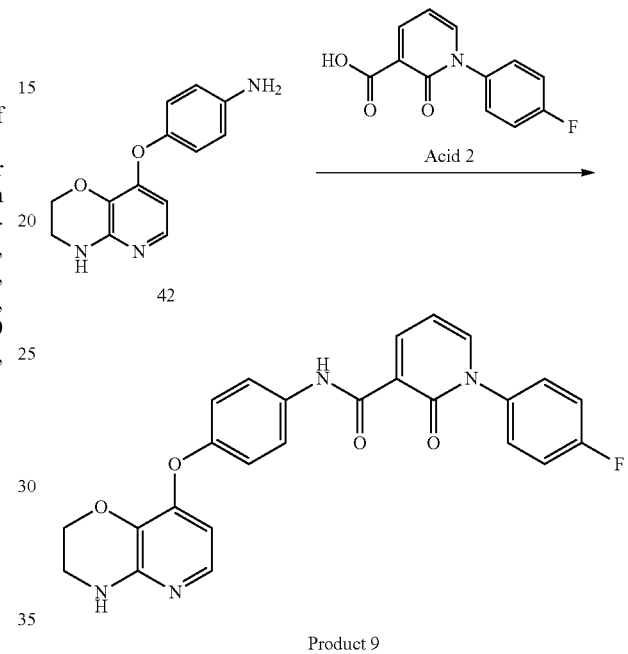

Product 9

The desired product 9 is synthesized by using the similar sequence and conditions as described for Example 2 with Acid2 instead of Acid1. MS: 459 (M+H)⁺. HNMR (DMSO-$d_6$): 11.90 (s, 1H), 8.56-8.58 (dd, 1H, J=5.40 Hz 1.50 Hz), 8.09-8.11 (dd, 1H, J=4.8 Hz 1.5 Hz), 7.67-7.71 (d, 2H, J=6.90 Hz), 7.59-7.62 (m, 2H), 7.47-7.48 (d, 1H, J=4.2 Hz), 7.40-7.44 (t, 2H, J=13.20 Hz), 6.99-7.01 (d, 2H, J=6.90 Hz), 6.80 (s, 1H), 6.69-6.73 (t, 1H, J=10.20 Hz), 6.07-6.08 (d, 1H, J=4.20 Hz), 4.08-4.10 (m, 2H), 3.40-3.41 (m, 2H).

Example 10

N-(3-fluoro-4-(2-oxo-2,3-dihydro-1H-pyrrolo[2,3-b]pyridin-4-yloxy)phenyl)-1-(4-fluorophenyl)-2-oxo-1,2-dihydropyridine-3-carboxamide (Product 10)

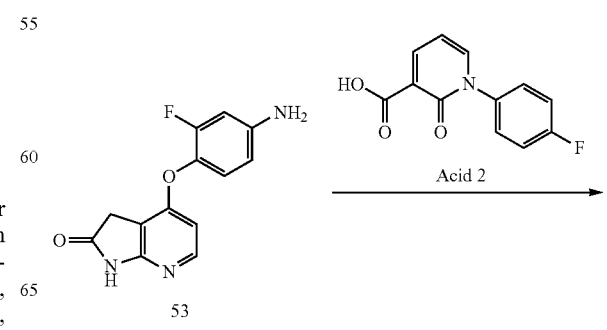

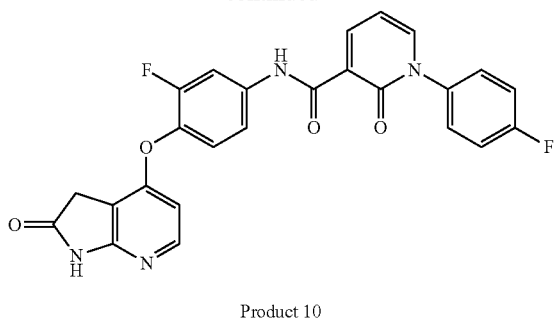

Product 10

The desired product 10 is synthesized by using the similar sequence and conditions as described for Example 2 with Acid2 instead of Acid1. MS: 475 (M+H)⁺.

Example 11

N-(3-fluoro-4-(3-oxo-3,4-dihydro-2H-pyrido[3,2-b][1,4]oxazin-8-yloxy)phenyl)-N-(4-fluorophenyl)cyclopropane-1,1-dicarboxamide (Product 11)

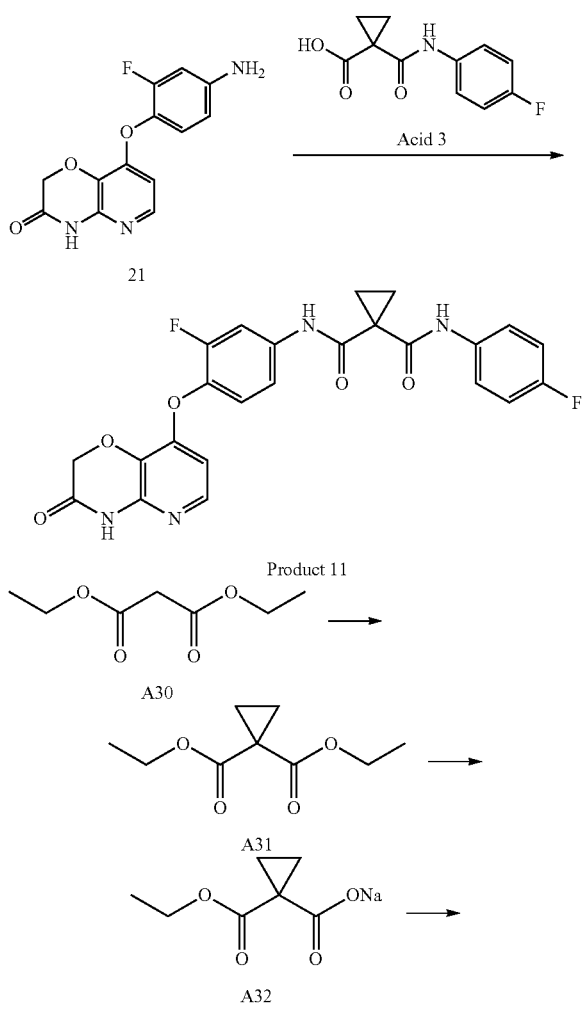

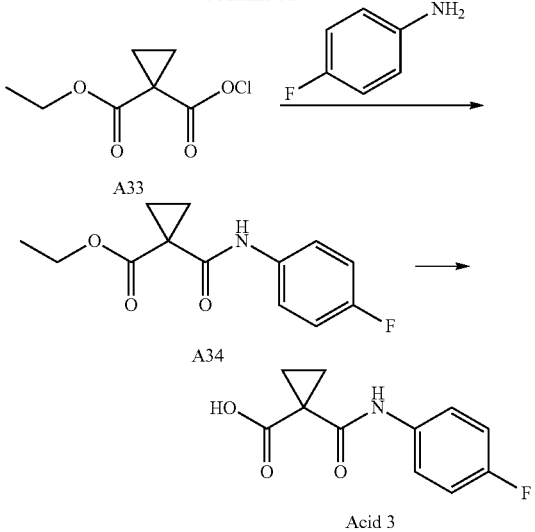

Acid 3

Step 1. Preparation of A31

Diethyl malonate (33.01 g), 1,2-dichloroethane (40.38 g), TBAB (2.09 g), benzene (100 ml), potassium carbonate (72.50 g), and Water (1.00 ml) were added into 500 ml flask and heated to 115° C. overnight. The reaction mixture was cooled to room temperature and filtrated. The filtrate was concentrated and followed by purification of flash column to give A31 (24.80 g).

Step 2. Preparation of A32

A31 (24.80 g) was mixed with ethanol (150 ml) and NaOH solution (5.08 g in 100 H₂O) at 0° C. The reaction mixture was stirred overnight and slowly warmed to room temperature. Then, ethanol was evaporated and washed by ether to give A32 (20.45 g).

Step 3. Preparation of A33

A32 (20.45 g) and thionyl chloride (150 ml) were mixed and reflux for 2 hrs. Then, thionyl chloride was evaporated after completion of the reaction monitored by TLC. The resulting solid was washed by DCM to give A33.

Step 4. Preparation of A34

A33 (From Step 3) in DCM (100 ml) was added slowly to the solution of p-fluoroaniline (16.05 g), TEA (40 ml) and DCM (200 ml) at 0° C. The reaction mixture was stirred overnight and warmed to room temperature slowly. Reaction was quenched by addition of water (150 ml). Then the organic phase was washed twice by dilute HCl, dried by anhydrous sodium sulfate. Evaporation of solvent the residue was purified by flash column to give A34 (20.23 g).

Step 5. Preparation of Acid3

A34 (19.40 g) was mixed with ethanol (100 ml) and 2N NaOH solution (200 ml). The reaction mixture was heated to 65° C. and stirred for 1 hr. The reaction mixture was cooled to below 10° C. and added slowly into a mixture of concentrated HCl (50 ml), ethyl acetate (200 ml) and water (300 ml). Organic layer was separated and washed twice by brine and dried with anhydrous sodium sulfate. Evaporated of organic solvent in vacuum gave to Acid3 (16.21 g).

Step 6. Preparation of Product 11

The desired product 11 is synthesized by using the similar sequence and conditions as described for Example 2 with Acid3 instead of Acid1. MS: 481 (M+H)⁺.

Example 12

N-(4-(2,3-dihydro-1H-pyrrolo[2,3-b]pyridin-4-yloxy)-3-fluorophenyl)-N-(4-fluorophenyl)cyclopropane-1,1-dicarboxamide (Product 12)

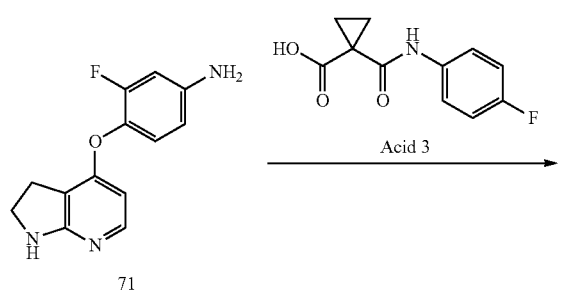

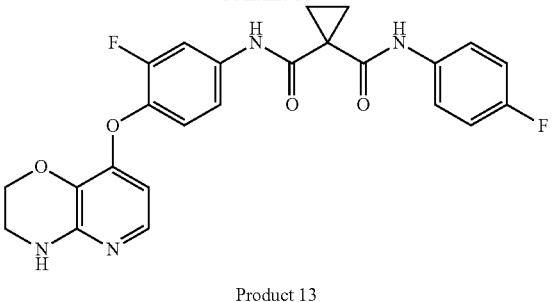

Product 13

The desired product 13 is synthesized by using the similar sequence and conditions as described for Example 2 with Acid3 instead of Acid1. MS: 467 (M+H)⁺.

Example 14

N-(4-(3,4-dihydro-2H-pyrido[3,2-b][1,4]oxazin-8-yloxy)phenyl)-N-(4-fluorophenyl)cyclopropane-1,1-dicarboxamide (Product 14)

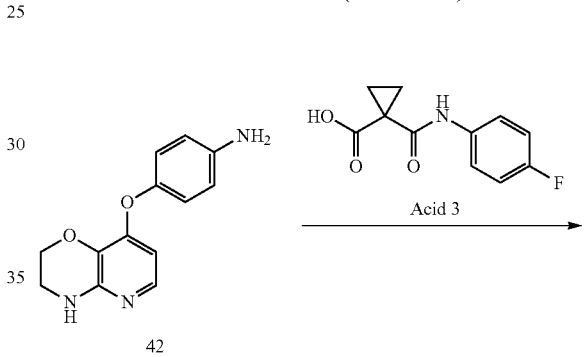

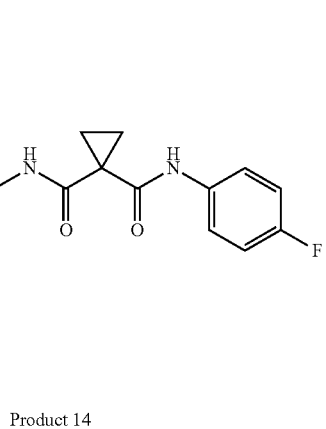

Product 14

Product 12

The desired product 12 is synthesized by using the similar sequence and conditions as described for Example 2 with Acid3 instead of Acid1. MS: 451 (M+H)⁺. HNMR (DMSO-$d_6$): 10.30 (s, 1H), 9.99 (s, 1H), 7.79-7.82 (d, 1H, J=10.20 Hz), 7.56-7.78 (m, 3H), 7.40-7.42 (d, 1H, J=6.30 Hz), 7.21-7.26 (t, 1H, J=13.50 Hz), 7.12-7.17 (t, 2H, J=13.20 Hz), 6.90-6.95 (t, 1H, J=13.80 Hz), 6.36-6.48 (m, 3H), 5.80-5.86 (dd, 1H, J=12.00 Hz 4.5 Hz), 5.39 (s, 1H), 3.41-3.52 (m, 2H), 2.84-2.92 (m, 2H)

Example 13

N-(4-(3,4-dihydro-2H-pyrido[3,2-b][1,4]oxazin-8-yloxy)-3-fluorophenyl)-N-(4-fluorophenyl)cyclopropane-1,1-dicarboxamide (Product 13)

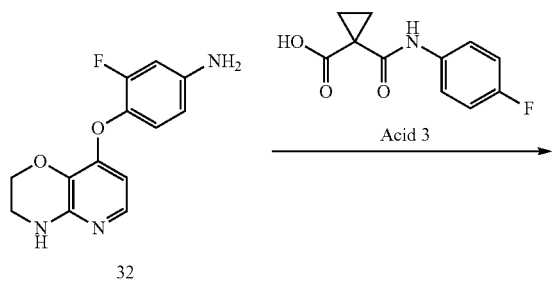

The desired product 14 is synthesized by using the similar sequence and conditions as described for Example 2 with Acid3 instead of Acid1. MS: 449 (M+H)⁺. HNMR (DMSO-$d_6$): 10.04-10.07 (d, 2H, J=9.30 Hz), 7.59-7.64 (m, 4H), 7.46-7.47 (d, 1H, J=4.20 Hz), 7.12-7.16 (t, 2H, J=13.50 Hz), 6.96-6.98 (d, 2H, J=6.90 Hz), 6.78 (s, 1H), 6.02-6.03 (d, 1H, J=4.20 Hz), 4.07-4.10 (m, 2H), 3.40-3.43 (m, 2H), 1.44 (s, 4H).

Example 15

N-(3-fluoro-4-(2-oxo-2,3-dihydro-1H-pyrrolo[2,3-b]pyridin-4-yloxy)phenyl)-N-(4-fluorophenyl)cyclopropane-1,1-dicarboxamide (Product 15)

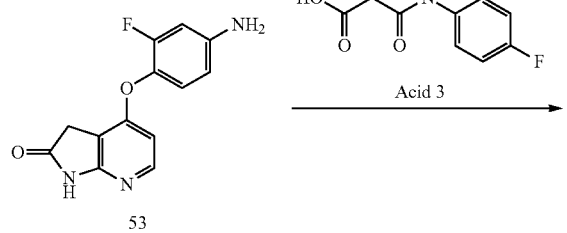

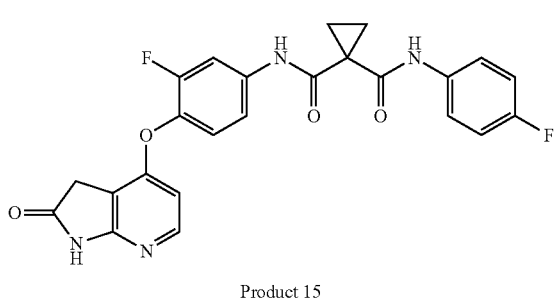

Product 15

The desired product 15 is synthesized by using the similar sequence and conditions as described for Example 2 with Acid3 instead of Acid1. MS: 465 (M+H)$^+$.

Example 16

8-(6-(2-(4-fluorophenylamino)-1-methyl-6-oxo-1,6-dihydropyrimidin-5-yl)pyridin-3-yloxy)-2H-pyrido[3,2-b][1,4]oxazin-3(4H)-one (Product 16)

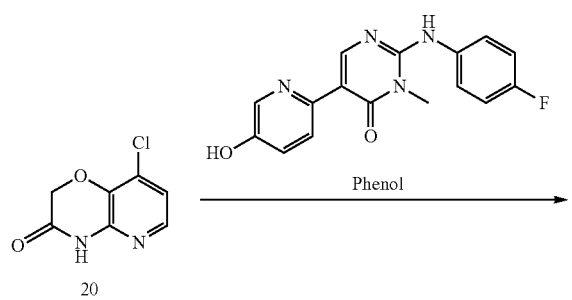

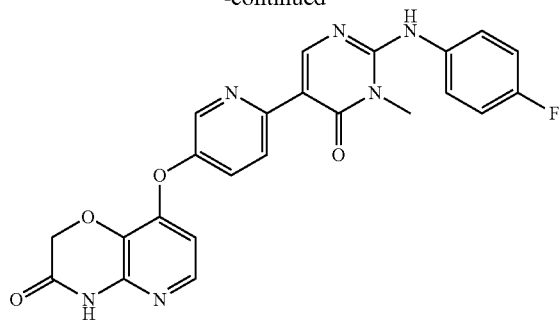

Product 16

The desired product 16 is synthesized by using the similar sequence and conditions as described for Example 2 with Phenol instead of Acid1. MS: 461 (M+H)$^+$.

Example 17

5-(5-(2,3-dihydro-1H-pyrrolo[2,3-b]pyridin-4-yloxy)pyridin-2-yl)-2-(4-fluorophenylamino)-3-methylpyrimidin-4(3H)-one (Product 17)

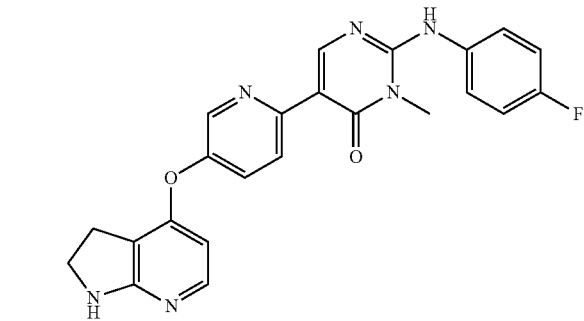

Product 17

The desired product 17 is synthesized by using the similar sequence and conditions as described for Example 2 with Phenol instead of Acid1. MS: 431 (M+H)$^+$.

Example 18

N-(3-fluoro-4-(3-oxo-3,4-dihydro-2H-pyrido[3,2-b][1,4]oxazin-8-yloxy)phenyl)-1,5-dimethyl-3-oxo-2-phenyl-2,3-dihydro-1H-pyrazole-4-carboxamide (Product 18)

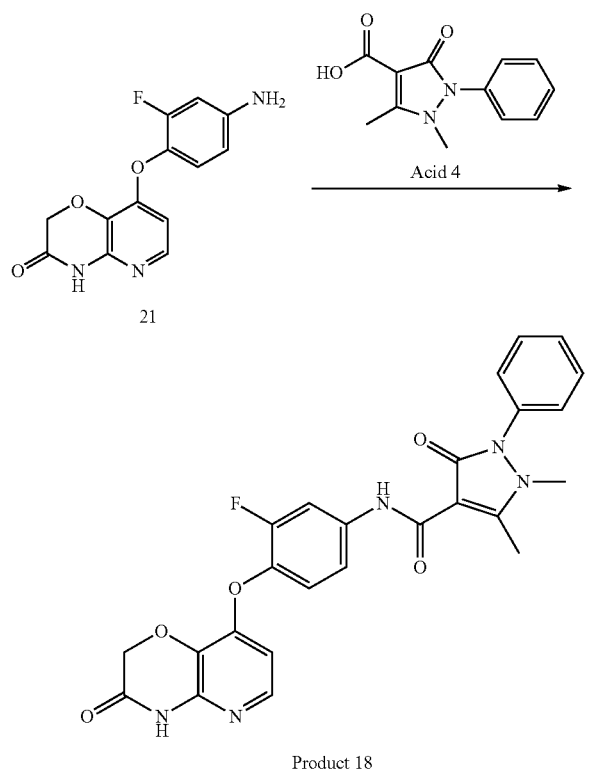

Product 18

The desired product 18 is synthesized by using the similar sequence and conditions as described for Example 2 with Acid4 instead of Acid1. MS: 490 (M+H)⁺.

Example 19

N-(4-(2,3-dihydro-1H-pyrrolo[2,3-b]pyridin-4-yloxy)-3-fluorophenyl)-1,5-dimethyl-3-oxo-2-phenyl-2,3-dihydro-1H-pyrazole-4-carboxamide (Product 19)

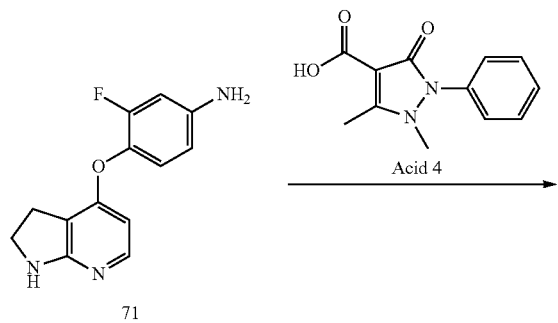

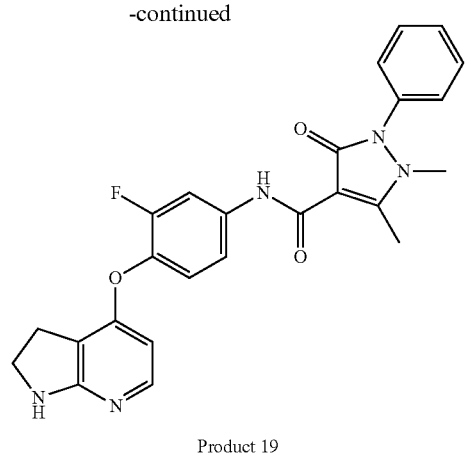

Product 19

The desired product 19 is synthesized by using the similar sequence and conditions as described for Example 2 with Acid4 instead of Acid1. MS: 460 (M+H)⁺. HNMR (DMSO-$d_6$): 10.91 (s, 1H), 7.88-7.95 (dd, 1H, J=10.50 Hz 1.50 Hz), 7.60-7.62 (m, 3H), 7.52-7.53 (m, 1H), 7.42-7.44 (m, 2H), 7.22-7.32 (m, 2H), 6.77 (s, 1H), 5.93-5.95 (d, 1H, J=4.50 Hz), 3.49-3.53 (m, 2H), 3.37 (s, 3H), 2.84-2.89 (m, 2H), 2.70 (s, 3H)

Example 20

N-(4-(3,4-dihydro-2H-pyrido[3,2-b][1,4]oxazin-8-yloxy)-3-fluorophenyl)-1,5-dimethyl-3-oxo-2-phenyl-2,3-dihydro-1H-pyrazole-4-carboxamide (Product 20)

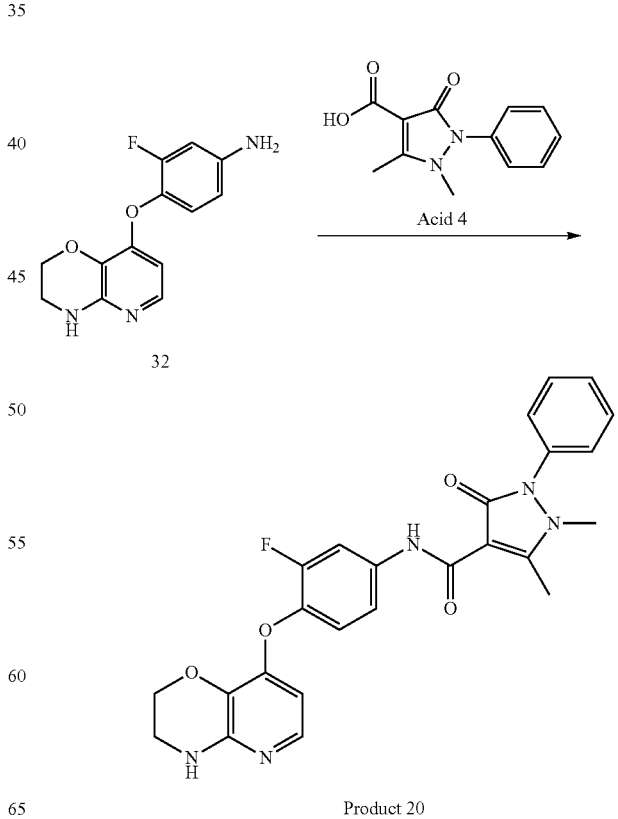

Product 20

The desired product 20 is synthesized by using the similar sequence and conditions as described for Example 2 with Acid4 instead of Acid1. MS: 476 (M+H)+. HNMR (DMSO-d$_6$): 10.87 (s, 1H), 7.86-7.90 (dd, 1H, J=9.60 Hz 1.50 Hz), 7.42-7.61 (m, 6H), 7.12-7.26 (m, 2H), 6.897 (s, 1H), 5.99-6.00 (d, 1H, J=4.2 Hz), 4.12-4.14 (m, 2H), 3.42-3.43 (m, 2H), 3.36 (s, 3H), 2.70 (s, 3H).

Example 21

N-(4-(3,4-dihydro-2H-pyrido[3,2-b][1,4]oxazin-8-yloxy)phenyl)-5-(4-fluorophenyl)-4-oxo-1,4-dihydropyridine-3-carboxamide (Product 21)

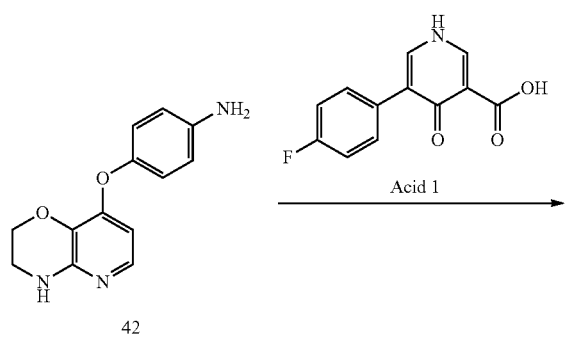

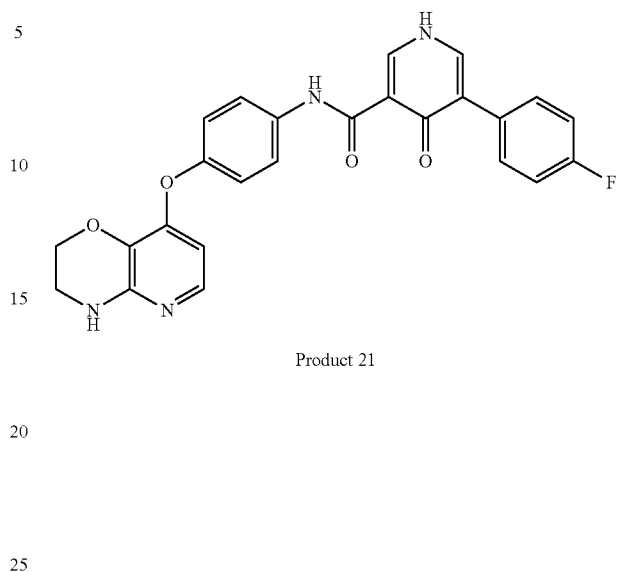

Product 21

The desired product 21 is synthesized by using the similar sequence and conditions as described for Example 2. MS: 459 (M+H)+.

| Ex No | Chemical Name | Structure | Physical Data (MS) (M + H)+ |
|---|---|---|---|
| 22 | 5-(4-Fluoro-phenyl)-4-oxo-1,4-dihydro-pyridine-3-carboxylic acid [4-(3,4-dihydro-2H-pyrido[3,2-b][1,4]thiazin-8-yloxy)-3-fluoro-phenyl]-amide | 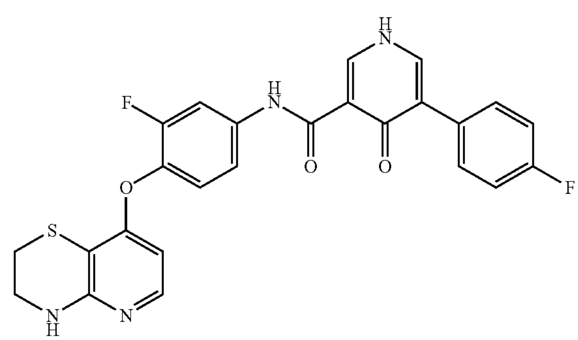 [SMILES: O=C(Nc1ccc(Oc2ccnc3c2SCCN3)c(F)c1)c1c[nH]cc(-c2ccc(F)cc2)c1=O] | 493 |
| 23 | 5-(4-Fluoro-phenyl)-4-oxo-1,4-dihydro-pyridine-3-carboxylic acid [4-(3,4-dihydro-2H-pyrido[3,2-b][1,4]thiazin-8-yloxy)-phenyl]-amide | 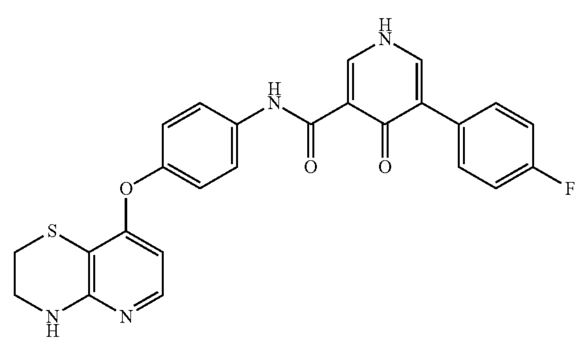 [SMILES: O=C(Nc1ccc(Oc2ccnc3c2SCCN3)cc1)c1c[nH]cc(-c2ccc(F)cc2)c1=O] | 475 |

-continued

| Ex No | Chemical Name | Structure | Physical Data (MS) (M + H)+ |
|---|---|---|---|
| 24 | 1-(4-Fluoro-phenyl)-2-oxo-1,2-dihydro-pyridine-3-carboxylic acid [4-(3,4-dihydro-2H-pyrido[3,2-b][1,4]thiazin-8-yloxy)-3-fluoro-phenyl]-amide | 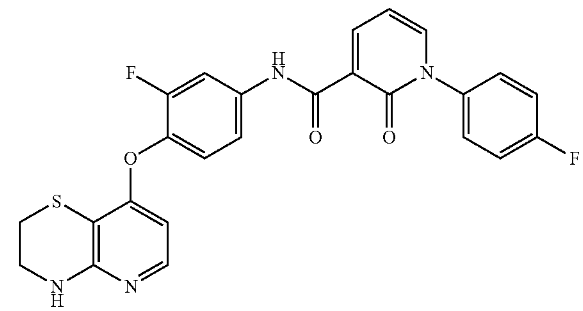 [SMILES: O=C(Nc1ccc(Oc2ccnc3c2SCCN3)c(F)c1)c1cccn(-c2ccc(F)cc2)c1=O] | 493 |
| 25 | 1-(4-Fluoro-phenyl)-2-oxo-1,2-dihydro-pyridine-3-carboxylic acid [4-(3,4-dihydro-2H-pyrido[3,2-b][1,4]thiazin-8-yloxy)-phenyl]-amide | 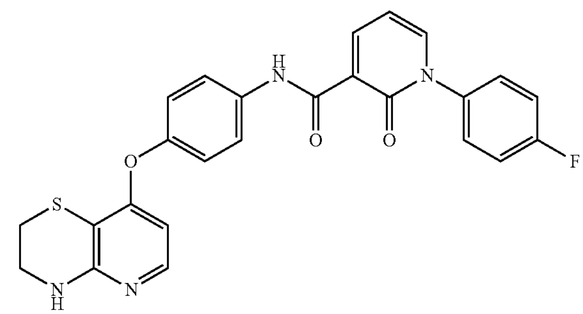 [SMILES: O=C(Nc1ccc(Oc2ccnc3c2SCCN3)cc1)c1cccn(-c2ccc(F)cc2)c1=O] | 475 |
| 26 | Cyclopropane-1,1-dicarboxylic acid [4-(3,4-dihydro-2H-pyrido [3,2-b][1,4]thiazin-8-yloxy)-phenyl]-amide (4-fluoro-phenyl)-amide | 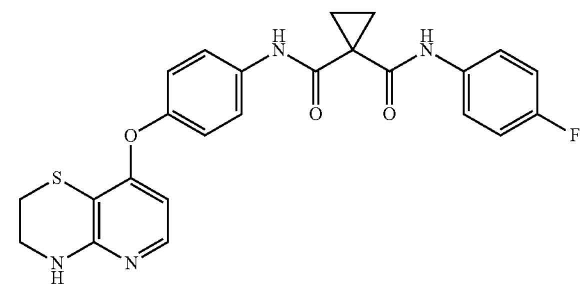 [SMILES: O=C(Nc1ccc(F)cc1)C1(C(=O)Nc2ccc(Oc3ccnc4c3SCCN4)cc2)CC1] | 465 |
| 27 | Cyclopropane-1,1-dicarboxylic acid [4-(3,4-dihydro-2H-pyrido [3,2-b][1,4]thiazin-8-yloxy)-3-fluoro-phenyl]-amide (4-fluoro-phenyl)-amide | 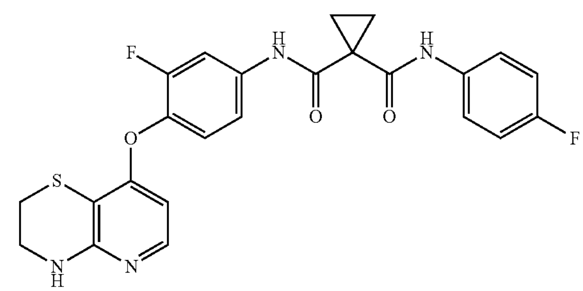 [SMILES: O=C(Nc1ccc(F)cc1)C1(C(=O)Nc2ccc(Oc3ccnc4c3SCCN4)c(F)c2)CC1] | 483 |
| 28 | 5-[5-(3,4-Dihydro-2H-pyrido[3,2-b][1,4]thiazin-8-yloxy)-pyridin-2-yl]-2-(4-fluoro-phenylamino)-3-methyl-3H-pyrimidin-4-one | 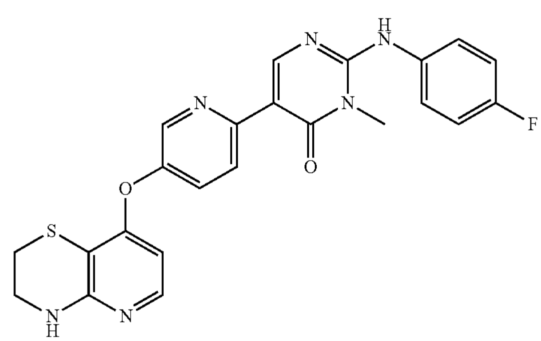 [SMILES: Cn1c(Nc2ccc(F)cc2)ncc(-c2ccc(Oc3ccnc4c3SCCN4)cn2)c1=O] | 463 |

-continued

| Ex No | Chemical Name | Structure | Physical Data (MS) (M + H)+ |
|---|---|---|---|
| 29 | 5-[5-(3,3-Dimethyl-3,4-dihydro-2H-pyrido[3,2-b][1,4]thiazin-8-yloxy)-pyridin-2-yl]-2-(4-fluoro-phenylamino)-3-methyl-3H-pyrimidin-4-one | 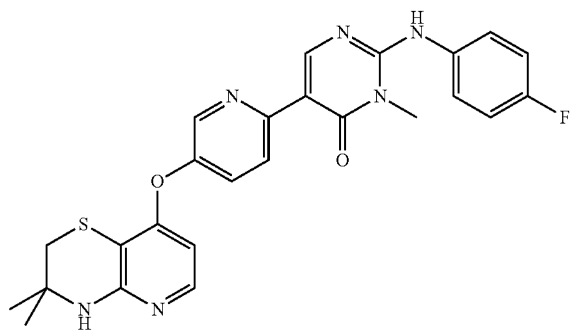 [SMILES: Cn1c(Nc2ccc(F)cc2)ncc(-c2ccc(Oc3ccnc4c3SCC(C)(C)N4)cn2)c1=O] | 491 |
| 30 | 5-(4-Fluoro-phenyl)-4-oxo-1,4-dihydro-pyridine-3-carboxylic acid [4-(3,3-dimethyl-3,4-dihydro-2H-pyrido[3,2-b][1,4]thiazin-8-yloxy)-3-fluoro-phenyl]-amide | 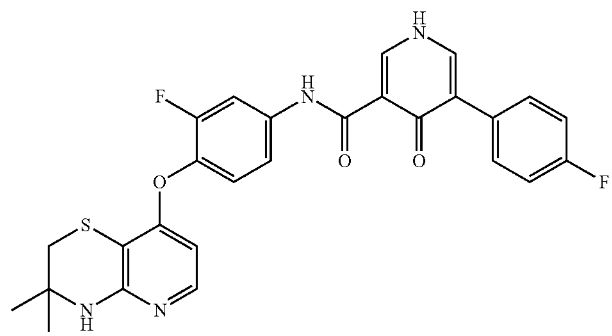 | 521 |
| 31 | 5-(4-Fluoro-phenyl)-4-oxo-1,4-dihydro-pyridine-3-carboxylic acid [4-(3,3-dimethyl-3,4-dihydro-2H-pyrido[3,2-b][1,4]thiazin-8-yloxy)-phenyl]-amide | 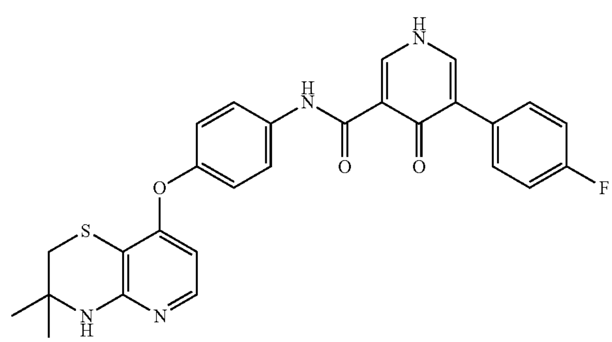 [SMILES: CC1(C)CSc2c(Oc3ccc(NC(=O)c4c[nH]cc(-c5ccc(F)cc5)c4=O)cc3)ccnc2N1] | 503 |
| 32 | 1-(4-Fluoro-phenyl)-2-oxo-1,2-dihydropyridine-3-carboxylic acid [4-(3,3-dimethyl-3,4-dihydro-2H-pyrido[3,2-b][1,4]thiazin-8-yloxy)-3-fluoro-phenyl]-amide | 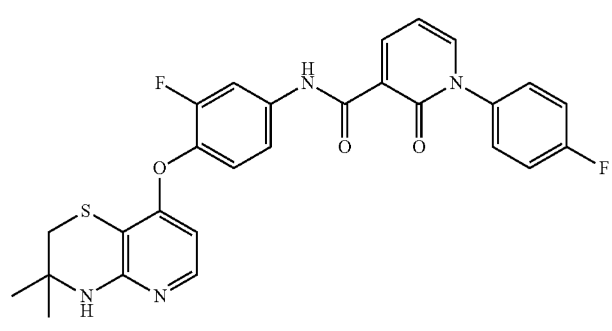 [SMILES: CC1(C)CSc2c(Oc3ccc(NC(=O)c4cccn(-c5ccc(F)cc5)c4=O)cc3F)ccnc2N1] | 521 |

-continued

| Ex No | Chemical Name | Structure | Physical Data (MS) (M + H)+ |
|---|---|---|---|
| 33 | 1-(4-Fluoro-phenyl)-2-oxo-1,2-dihydro-pyridine-3-carboxylic acid [4-(3,3-dimethyl-3,4-dihydro-2H-pyrido[3,2-b][1,4]thiazin-8-yloxy)-phenyl]-amide | 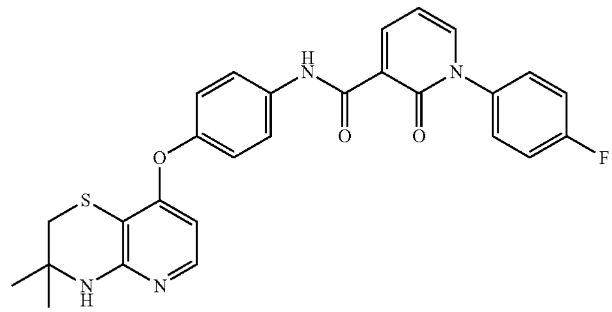 [SMILES: CC1(C)CSc2c(Oc3ccc(NC(=O)c4cccn(-c5ccc(F)cc5)c4=O)cc3)ccnc2N1] | 503 |
| 34 | Cyclopropane-1,1-dicarboxylic acid [4-(3,3-dimethyl-3,4-dihydro-2H-pyrido[3,2-b][1,4]thiazin-8-yloxy)-phenyl]-amide (4-fluoro-phenyl)-amide | 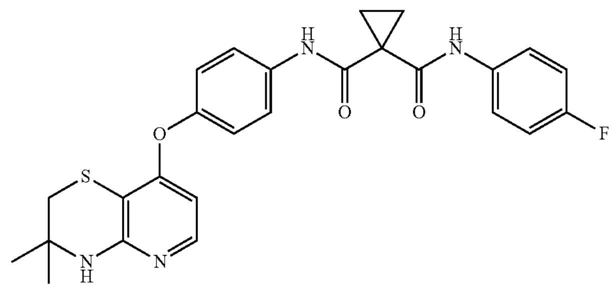 | 493 |
| 35 | Cyclopropane-1,1-dicarboxylic acid [4-(3,3-dimethyl-3,4-dihydro-2H-pyrido[3,2-b][1,4]thiazin-8-yloxy)-3-fluoro-phenyl]-amide(4-fluoro-phenyl)-amide | 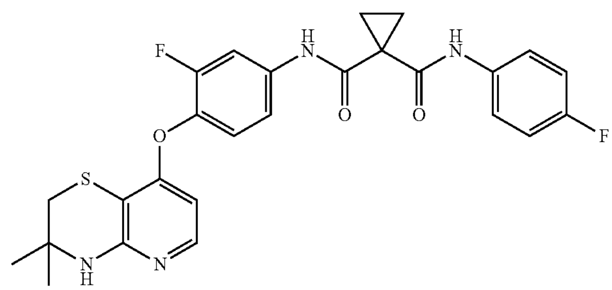 | 511 |
| 36 | 5-[5-(3,3-Dimethyl-3,4-dihydro-2H-pyrido[3,2-b][1,4]oxazin-8-yloxy)-pyridin-2-yl]-2-(4-fluoro-phenylamino)-3-methyl-3H-pyrimidin-4-one | 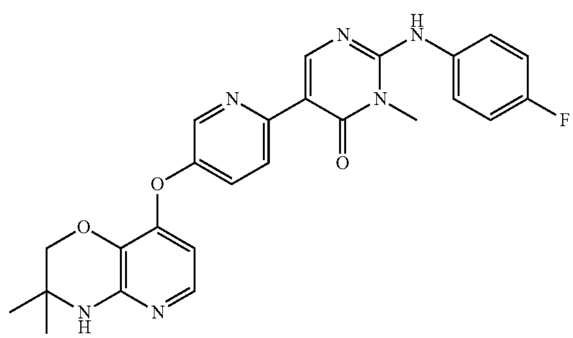 [SMILES: Cn1c(Nc2ccc(F)cc2)ncc(-c2ccc(Oc3ccnc4c3OCC(C)(C)N4)cn2)c1=O] | 475 |
| 37 | 5-(4-Fluoro-phenyl)-4-oxo-1,4-dihydro-pyridine-3-carboxylic acid [4-(3,3-dimethyl-3,4-dihydro-2H-pyrido[3,2-b][1,4]oxazin-8-yloxy)-3-fluoro-phenyl]-amide | 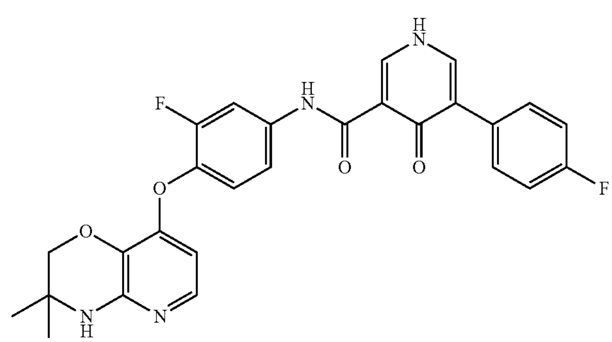 [SMILES: CC1(C)COc2c(Oc3ccc(NC(=O)c4c[nH]cc(-c5ccc(F)cc5)c4=O)cc3F)ccnc2N1] | 505 |

| Ex No | Chemical Name | Structure | Physical Data (MS) (M + H)+ |
|---|---|---|---|
| 38 | 5-(4-Fluoro-phenyl)-4-oxo-1,4-dihydro-pyridine-3-carboxylic acid [4-(3,3-dimethyl-3,4-dihydro-2H-pyrido[3,2-b][1,4]oxazin-8-yloxy)-phenyl]-amide | 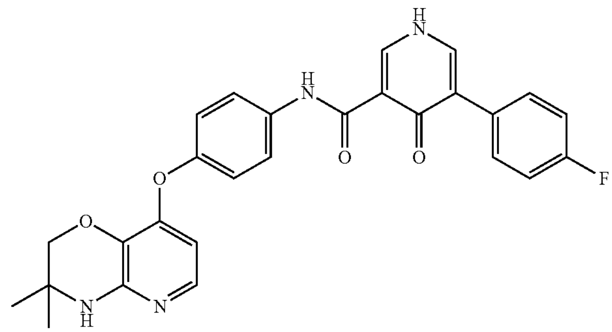 | 487 |
| 39 | 1-(4-Fluoro-phenyl)-2-oxo-1,2-dihydro-pyridine-3-carboxylic acid [4-(3,3-dimethyl-3,4-dihydro-2H-pyrido[3,2-b][1,4]oxazin-8-yloxy)-3-fluoro-phenyl]-amide | 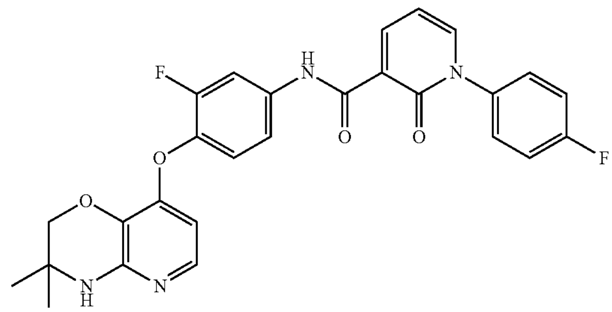 | 505 |
| 40 | 1-(4-Fluoro-phenyl)-2-oxo-1,2-dihydro-pyridine-3-carboxylic acid [4-(3,3-dimethyl-3,4-dihydro-2H-pyrido[3,2-b][1,4]oxazin-8-yloxy)-phenyl]-amide | 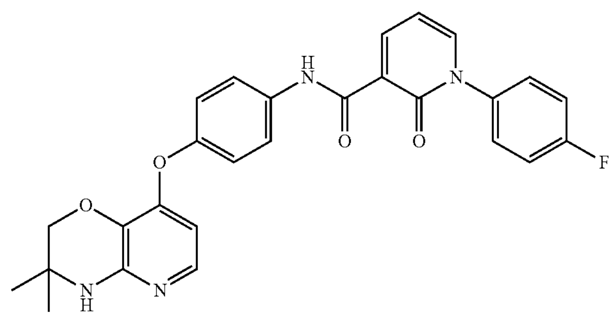 | 487 |
| 41 | Cyclopropane-1,1-dicarboxylic acid [4-(3,3-dimethyl-3,4-dihydro-2H-pyrido[3,2-b][1,4]oxazin-8-yloxy)-phenyl]-amide (4-fluoro-phenyl)-amide | 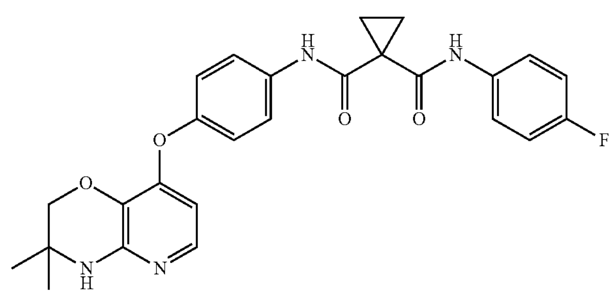 [SMILES: CC1(C)COc2c(Oc3ccc(NC(=O)C4(C(=O)Nc5ccc(F)cc5)CC4)cc3)ccnc2N1] | 477 |
| 42 | Cyclopropane-1,1-dicarboxylic acid [4-(3,3-dimethyl-3,4-dihydro-2H-pyrido[3,2-b][1,4]oxazin-8-yloxy)-3-fluoro-phenyl]-amide(4-fluoro-phenyl)-amide | 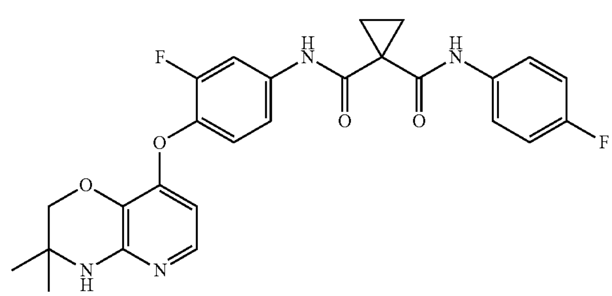 [SMILES: CC1(C)COc2c(Oc3ccc(NC(=O)C4(C(=O)Nc5ccc(F)cc5)CC4)cc3F)ccnc2N1] | 495 |

-continued

| Ex No | Chemical Name | Structure | Physical Data (MS) $(M + H)^+$ |
|---|---|---|---|
| 43 | 5-(4-Fluoro-phenyl)-4-oxo-1,4-dihydro-pyridine-3-carboxylic acid [4-(6,7,8,9-tetrahydro-5-thia-1,9-diaza-benzocyclohepten-4-yloxy)-phenyl]-amide | 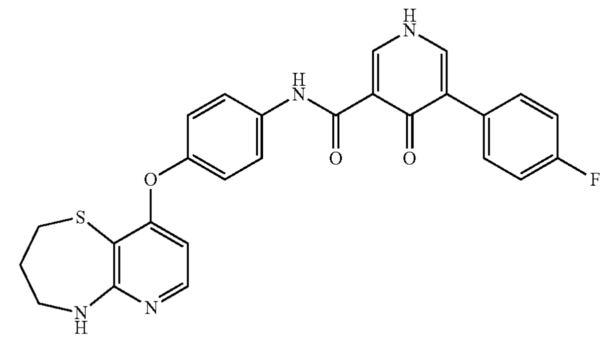 | 489 |
| 44 | 1-(4-Fluoro-phenyl)-2-oxo-1,2-dihydro-pyridine-3-carboxylic acid [3-fluoro-4-(6,7,8,9-tetrahydro-5-thia-1,9-diaza-benzocyclohepten-4-yloxy)-phenyl]-amide | 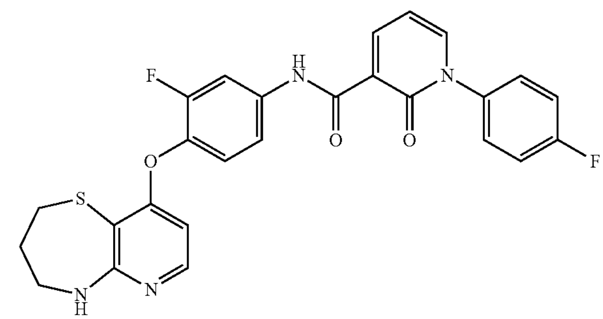 [SMILES: O=C(Nc1ccc(Oc2ccnc3c2SCCCN3)c(F)c1)c1cccn(-c2ccc(F)cc2)c1=O] | 507 |
| 45 | Cyclopropane-1,1-dicarboxylic acid (4-fluoro-phenyl)-amide[4-(6,7,8,9-tetrahydro-5-thia-1,9-diaza-benzocyclohepten-4-yloxy)-phenyl]-amide | 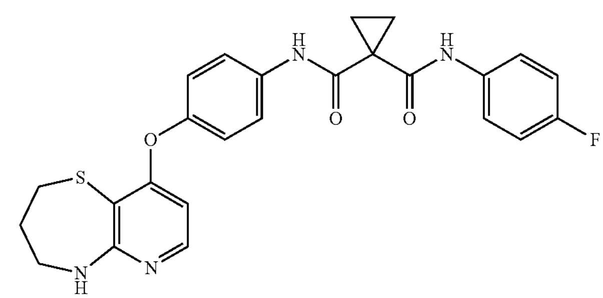 | 479 |
| 46 | Cyclopropane-1,1-dicarboxylic acid (4-fluoro-phenyl)-amide[3-fluoro-4-(6,7,8,9-tetrahydro-5-thia-1,9-diaza-benzocyclohepten-4-yloxy)-phenyl]-amide | 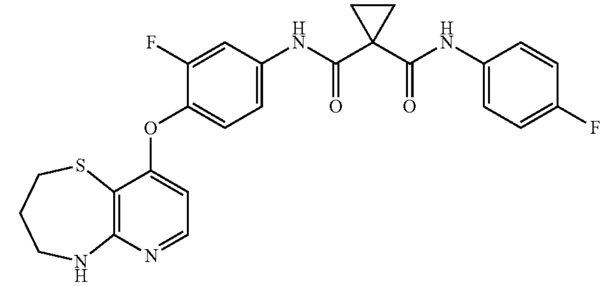 [SMILES: O=C(Nc1ccc(F)cc1)C1(C(=O)Nc2ccc(Oc3ccnc4c3SCCCN4)c(F)c2)CC1] | 497 |

-continued

| Ex No | Chemical Name | Structure | Physical Data (MS) (M + H)+ |
|---|---|---|---|
| 47 | 2-(4-Fluoro-phenylamino)-3-methyl-5-[5-(6,7,8,9-tetrahydro-5-thia-1,9-diaza-benzocyclohepten-4-yloxy)-pyridin-2-yl]-3H-pyrimidin-4-one | 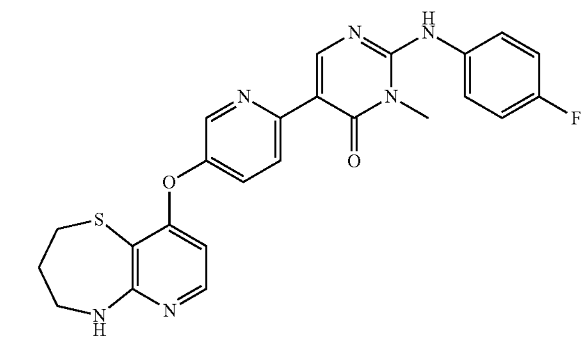 [SMILES: Cn1c(Nc2ccc(F)cc2)ncc(-c2ccc(Oc3ccnc4c3SCCCN4)cn2)c1=O] | 477 |
| 48 | 5-(4-Fluoro-phenyl)-4-oxo-1,4-dihydro-pyridine-3-carboxylic acid [3-fluoro-4-(6,7,8,9-tetrahydro-5-thia-1,9-diaza-benzocyclohepten-4-yloxy)-phenyl]-amide | 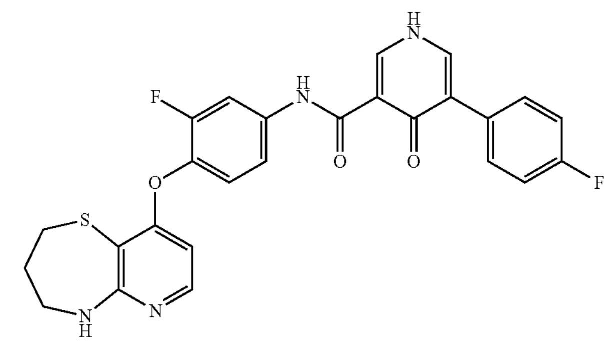 [SMILES: O=C(Nc1ccc(Oc2ccnc3c2OCCCN3)c(F)c1)c1c[nH]cc(-c2ccc(F)cc2)c1=O] | 507 |
| 49 | 1-(4-Fluoro-phenyl)-2-oxo-1,2-dihydro-pyridine-3-carboxylic acid [4-(6,7,8,9-tetrahydro-5-thia-1,9-diaza-benzocyclohepten-4-yloxy)-phenyl]-amide | 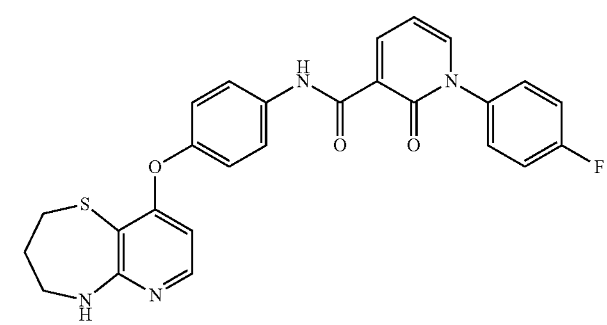 [SMILES: O=C(Nc1ccc(Oc2ccnc3c2OCCCN3)cc1)c1cccn(-c2ccc(F)cc2)c1=O] | 489 |
| 50 | 5-(4-Fluoro-phenyl)-4-oxo-1,4-dihydro-pyridine-3-carboxylic acid [3-fluoro-4-(6,7,8,9-tetrahydro-5-oxa-1,9-diaza-benzocyclohepten-4-yloxy)-phenyl]-amide | 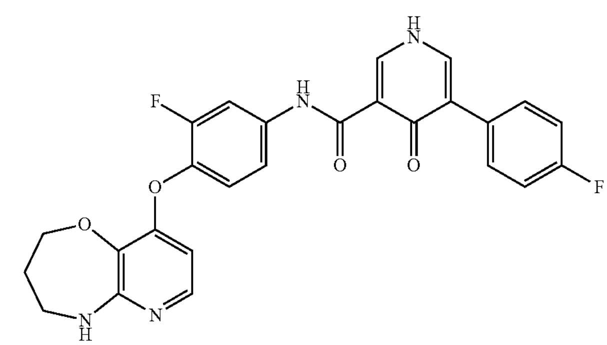 | 491 |

-continued

| Ex No | Chemical Name | Structure | Physical Data (MS) (M + H)+ |
|---|---|---|---|
| 51 | 1-(4-Fluoro-phenyl)-2-oxo-1,2-dihydro-pyridine-3-carboxylic acid [4-(6,7,8,9-tetrahydro-5-oxa-1,9-diaza-benzocyclohepten-4-yloxy)-phenyl]-amide | 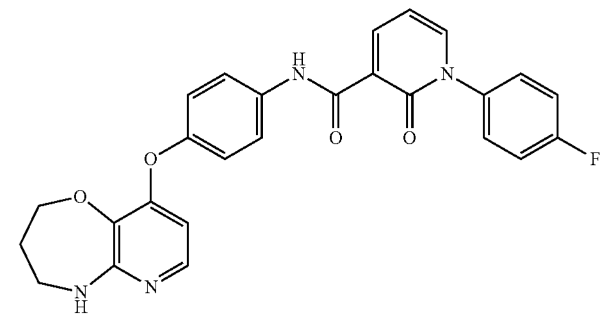 | 473 |
| 52 | 2-(4-Fluoro-phenylamino)-3-methyl-5-[5-(6,7,8,9-tetrahydro-5-oxa-1,9-diaza-benzocyclohepten-4-yloxy)-pyridin-2-yl]-3H-pyrimidin-4-one | 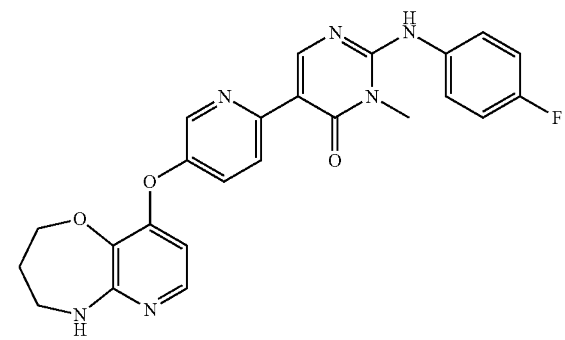 [SMILES: Cn1c(Nc2ccc(F)cc2)ncc(-c2ccc(Oc3ccnc4c3OCCCN4)cn2)c1=O] | 461 |
| 53 | Cyclopropane-1,1-dicarboxylic acid (4-fluoro-phenyl)-amide[3-fluoro-4-(6,7,8,9-tetrahydro-5-oxa-1,9-diaza-benzocyclohepten-4-yloxy)-phenyl]-amide | 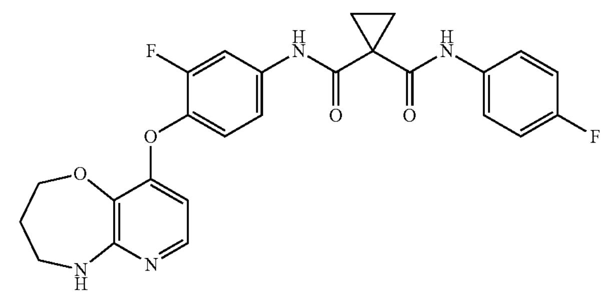 | 481 |
| 54 | Cyclopropane-1,1-dicarboxylic acid (4-fluoro-phenyl)-amide[4-(6,7,8,9-tetrahydro-5-oxa-1,9-diaza-benzocyclohepten-4-yloxy)-phenyl]-amide | 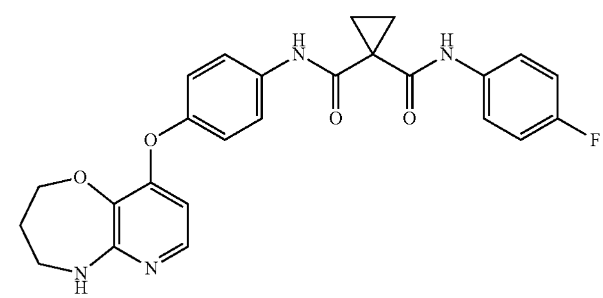 | 463 |
| 55 | 1-(4-Fluoro-phenyl)-2-oxo-1,2-dihydro-pyridine-3-carboxylic acid [3-fluoro-4-(6,7,8,9-tetrahydro-5-oxa-1,9-diaza-benzocyclohepten-4-yloxy)-phenyl]-amide | 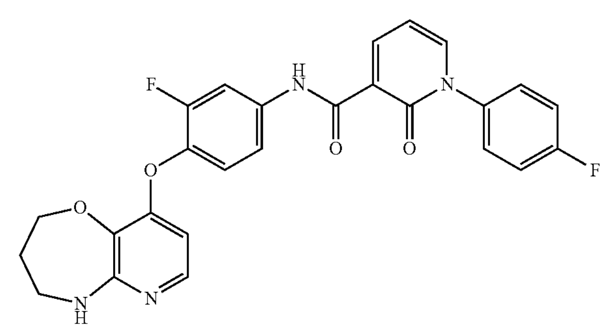 | 491 |

| Ex No | Chemical Name | Structure | Physical Data (MS) (M + H)+ |
|---|---|---|---|
| 56 | 5-(4-Fluoro-phenyl)-4-oxo-1,4-dihydro-pyridine-3-carboxylic acid [4-(6,7,8,9-tetrahydro-5-oxa-1,9-diaza-benzocyclohepten-4-yloxy)-phenyl]-amide | 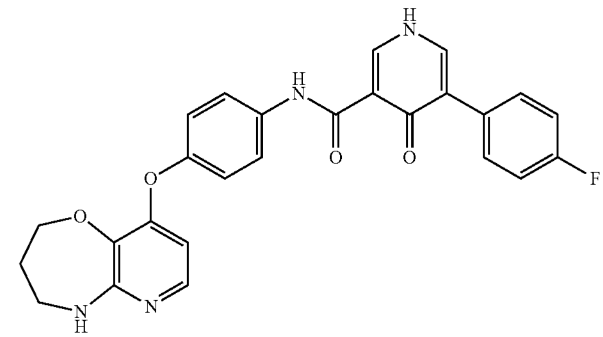 [SMILES: O=C(Nc1ccc(Oc2ccnc3c2OCCCN3)cc1)c1c[nH]cc(-c2ccc(F)cc2)c1=O] | 473 |
| 57 | N-(4-(3,4-dimethyl-2,3,4,5-tetrahydropyrido[3,2-b][1,4]oxazepin-9-yloxy)phenyl)-5-(4-fluorophenyl)-4-oxo-1,4-dihydropyridine-3-carboxamide | 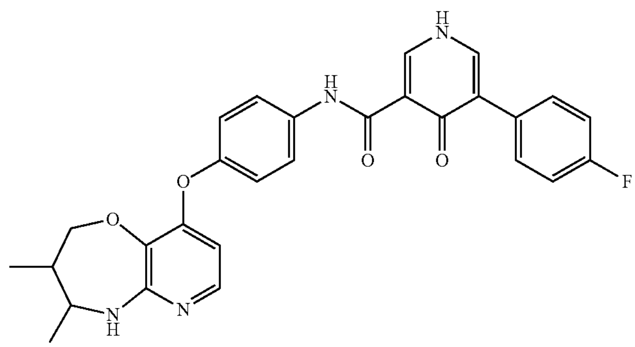 [SMILES: CC1COc2c(Oc3ccc(NC(=O)c4c[nH]cc(-c5ccc(F)cc5)c4=O)cc3)ccnc2NC1C] | 501 |
| 58 | 1-(4-Fluoro-phenyl)-2-oxo-1,2-dihydro-pyridine-3-carboxylic acid [4-(7,7-dimethyl-6,7,8,9-tetrahydro-5-thia-1,9-diaza-benzocyclohepten-4-yloxy)-phenyl]-amide | 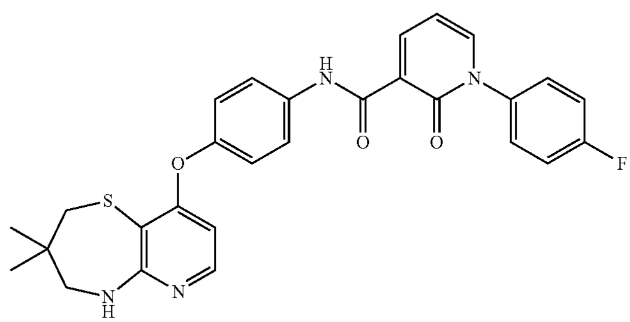 [SMILES: CC1(C)CNc2nccc(Oc3ccc(NC(=O)c4cccn(-c5ccc(F)cc5)c4=O)cc3)c2SC1] | 517 |
| 59 | 5-(4-Fluoro-phenyl)-4-oxo-1,4-dihydro-pyridine-3-carboxylic acid [4-(3,3-difluoro-2,3-dihydro-1H-pyrrolo[2,3-b]pyridin-4-yloxy)-3-fluoro-phenyl]-amide | 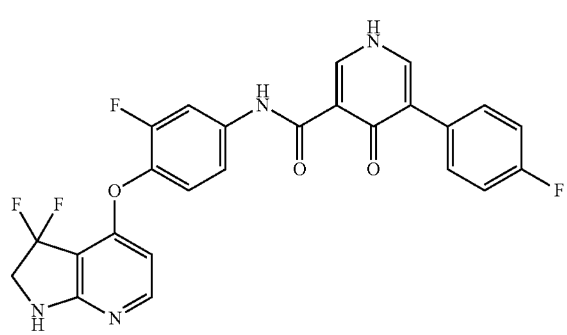 [SMILES: O=C(Nc1ccc(Oc2ccnc3c2C(F)(F)CN3)c(F)c1)c1c[nH]cc(-c2ccc(F)cc2)c1=O] | 497 |

-continued

| Ex No | Chemical Name | Structure | Physical Data (MS) (M + H)+ |
|---|---|---|---|
| 60 | N-(4-(2,2-difluoro-2,3-dihydro-1H-pyrrolo[2,3-b]pyridin-4-yloxy)-3-fluorophenyl)-5-(4-fluorophenyl)-4-oxo-1,4-dihydropyridine-3-carboxamide | 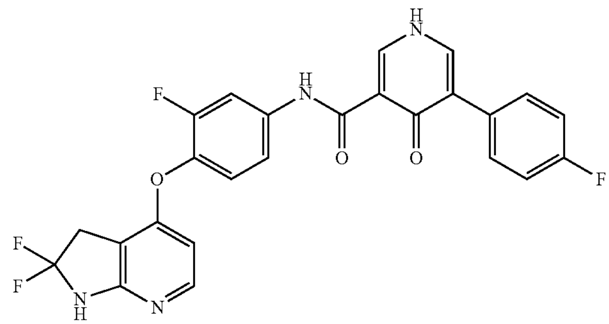 [SMILES: O=C(Nc1ccc(Oc2ccnc3c2CC(F)(F)N3)c(F)c1)c1c[nH]cc(-c2ccc(F)cc2)c1=O] | 497 |
| 61 | N-(3-fluoro-4-(3-oxo-2,3-dihydro-1H-pyrrolo[2,3-b]pyridin-4-yloxy)phenyl)-1-(4-fluorophenyl)-2-oxo-1,2-dihydropyridine-3-carboxamide | 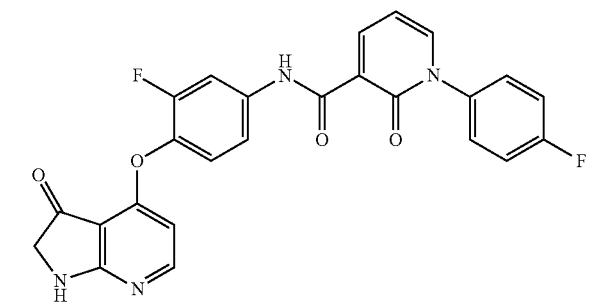 [SMILES: O=C1CNc2nccc(Oc3ccc(NC(=O)c4cccn(-c5ccc(F)cc5)c4=O)cc3F)c21] | 475 |
| 62 | N-(3-fluoro-5-methyl-4-(2-oxo-2,3-dihydro-1H-pyrrolo[2,3-b]pyridin-4-yloxy)phenyl)-N-(4-fluorophenyl)cyclopropane-1,1-dicarboxamide | 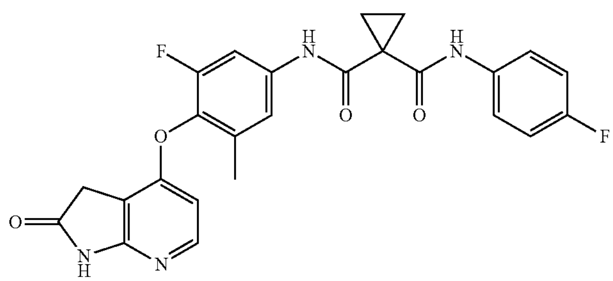 [SMILES: Cc1cc(NC(=O)C2(C(=O)Nc3ccc(F)cc3)CC2)cc(F)c1Oc1ccnc2c1CC(=O)N2] | 479 |
| 63 | Cyclopropane-1,1-dicarboxylic acid [2,3-difluoro-4-(2-oxo-2,3-dihydro-1H-pyrrolo[2,3-b]pyridin-4-yloxy)-phenyl]-amide (4-fluoro-phenyl)-amide | 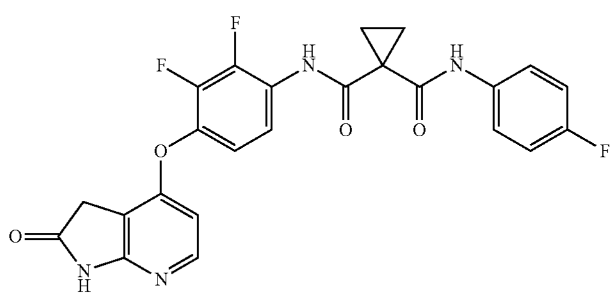 [SMILES: O=C1Cc2c(Oc3ccc(NC(=O)C4(C(=O)Nc5ccc(F)cc5)CC4)c(F)c3F)ccnc2N1] | 483 |
| 64 | 3-(4-Fluoro-phenyl)-2-oxo-imidazolidine-1-carboxylic acid [4-(2,3-di-hydro-1H-pyrrolo[2,3-b]pyridin-4-yloxy)-3-fluoro-phenyl]-amide | 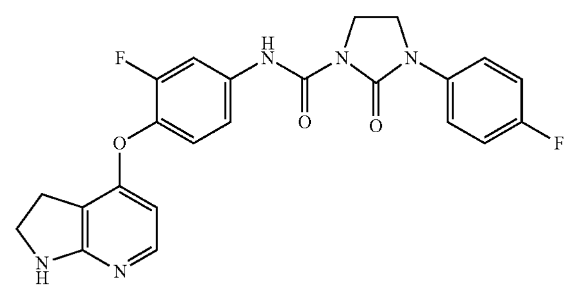 [SMILES: O=C(Nc1ccc(Oc2ccnc3c2CCN3)c(F)c1)N1CCN(c2ccc(F)cc2)C1=O] | 452 |

-continued

| Ex No | Chemical Name | Structure | Physical Data (MS) (M + H)+ |
|---|---|---|---|
| 65 | 3-(4-Fluoro-phenyl)-2-oxo-imidazolidine-1-carboxylic acid [4-(3,4-dihydro-2H-pyrido[3,2-b][1,4]oxazin-8-yloxy)-3-fluoro-phenyl]-amide | 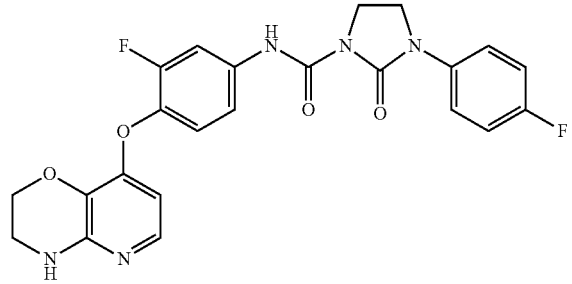 [SMILES: O=C(Nc1ccc(Oc2ccnc3c2OCCN3)c(F)c1)N1CCN(c2ccc(F)cc2)C1=O] | 468 |
| 66 | 3-(4-Fluoro-phenyl)-2-oxo-imidazolidine-1-carboxylic acid [4-(3,4-dihydro-2H-pyrido[3,2-b][1,4]thiazin-8-yloxy)-3-fluoro-phenyl]-amide | 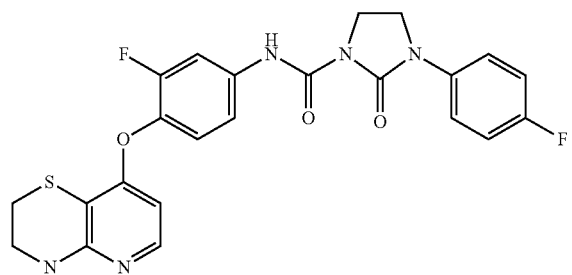 | 484 |
| 67 | 3-(4-Fluoro-phenyl)-2-oxo-imidazolidine-1-carboxylic acid [3-fluoro-4-(6,7,8,9-tetrahydro-5-oxa-1,9-diaza-benzocyclohepten-4-yloxy)-phenyl]-amide | 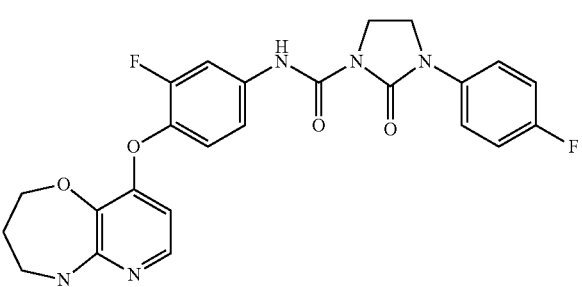 | 482 |
| 68 | N-(4-(3',4'-dihydrospiro[cyclopropane-1,2'-pyrido[3,2-b][1,4]oxazine]-8'-yloxy)-3-fluorophenyl)-5-(4-fluorophenyl)-4-oxo-1,4-dihydropyridine-3-carboxamide | 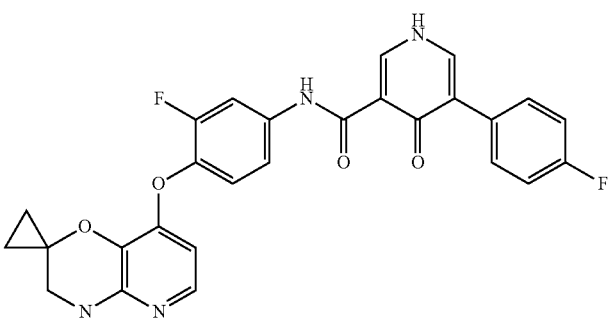 | 503 |
| 69 | N-(3-fluoro-4-(2-(hydroxymethyl)-3,4-dihydro-2H-pyrido[3,2-b][1,4]oxazin-8-yloxy)phenyl)-5-(4-fluorophenyl)-4-oxo-1,4-dihydropyridine-3-carboxamide | 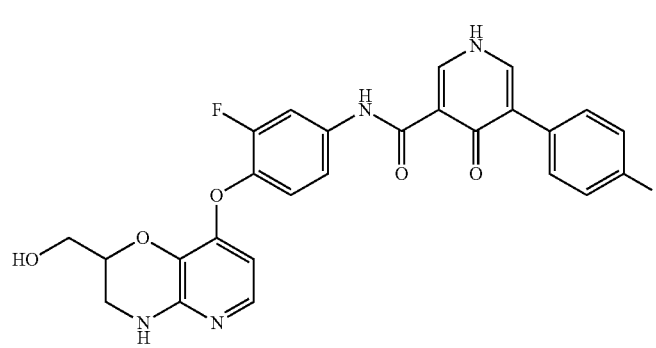 | 507 |

-continued

| Ex No | Chemical Name | Structure | Physical Data (MS) (M + H)+ |
|---|---|---|---|
| 70 | 8-(2-fluoro-4-(5-(4-fluorophenyl)-4-oxo-1,4-dihydropyridine-3-carboxamido)phenoxy)-3,4-dihydro-2H-pyrido[3,2-b][1,4]oxazine-2-carboxamide | 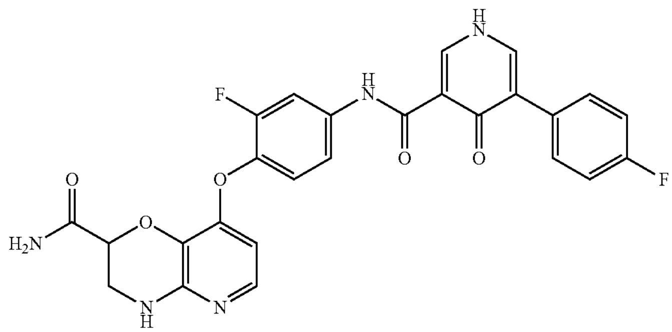 [SMILES: NC(=O)C1CNc2nccc(Oc3ccc(NC(=O)c4c[nH]cc(-c5ccc(F)cc5)c4=O)cc3F)c2O1] | 520 |
| 71 | N-(4-(2-(aziridin-1-ylmethyl)-3,4-dihydro-2H-pyrido[3,2-b][1,4]oxazin-8-yloxy)-3-fluorophenyl)-5-(4-fluorophenyl)-4-oxo-1,4-dihydropyridine-3-carboxamide | 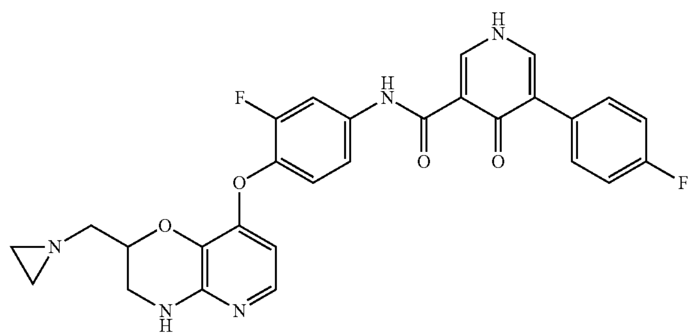 [SMILES: O=C(Nc1ccc(Oc2ccnc3c2OC(CN2CC2)CN3)c(F)c1)c1c[nH]cc(-c2ccc(F)cc2)c1=O] | 532 |
| 72 | N-(3-fluoro-4-(3-(2-hydroxyethyl)-2,3-dihydro-1H-pyrrolo[2,3-b]pyridin-4-yloxy)phenyl)-5-(4-fluorophenyl)-4-oxo-1,4-dihydropyridine-3-carboxamide | 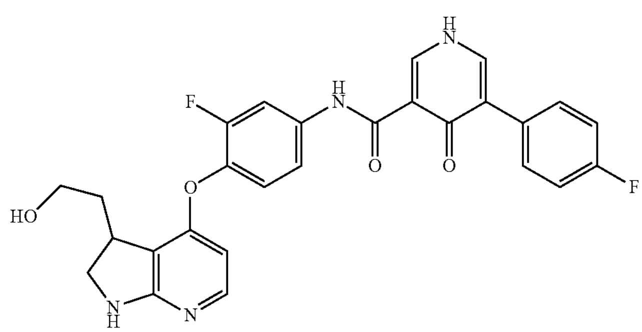 [SMILES: O=C(Nc1ccc(Oc2ccnc3c2C(CCO)CN3)c(F)c1)c1c[nH]cc(-c2ccc(F)cc2)c1=O] | 505 |
| 73 | N-(3-fluoro-4-(2'-oxo-1',2'-dihydrospiro[cyclopropane-1,3'-pyrrolo[2,3-b]pyridine]-4'-yloxy)phenyl)-5-(4-fluorophenyl)-4-oxo-1,4-dihydropyridine-3-carboxamide | 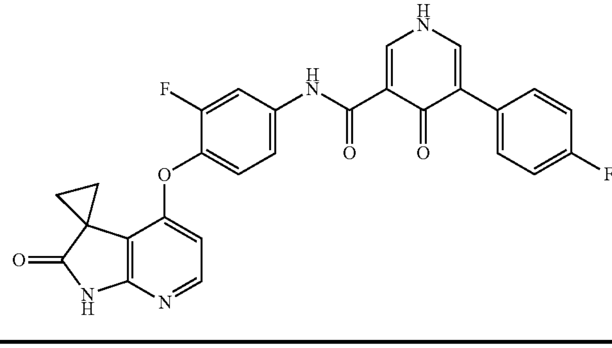 | 501 |

Pharmacological Testing

The following assays demonstrate that certain compounds of the present invention potently inhibit c-Met phosphorylation in vitro, potently inhibit c-Met in vivo, and have dose dependent anti-tumor activity in certain xenograft models.

Biological Assays

Met (h) is incubated with 8 mM MOPS pH7.0, 0.2 mM EDTA, 250 µM KKKSPGEYVNIEFG, 10 mM MgAcetate, [$\gamma$-$^{33}$P-ATP] (specific activity approx. 500 cpm/pmol, concentration as required) and 0.2 µM test compound. The reaction is initiated by the addition of the MgATP mix. After incubation for 40 minutes at room temperature, the reaction is stopped by the addition of 3% phosphoric acid solution. 10 µL of the reaction is then spotted onto a P30 filtermat and washed three times for 5 minutes in 75 mM phosphoric acid and once in methanol prior to drying and scintillation counting. This assay is performed by Millipore. The experiment is carried out in duplicate. The value for the control sample (DMSO) was set to 100%, and the values for the compound-treated samples were expressed as activity relative to the control sample.

TABLE 1

| Example | Activity (control) % |
| --- | --- |
| 1 @0.2 µM | 1 |
| 3 @0.2 µM | 6 |
| 7 @0.2 µM | 11 |
| 9 @0.2 µM | 6 |
| 12 @0.2 µM | 15 |
| 19 @0.2 µM | 51 |
| 20 @0.2 µM | 45 |
| 56 @0.2 µM | 2 |

Cellular Proliferation Analysis

Cell proliferation analysis was conducted by the MTS assay protocol. Briefly, U87-MG cells will be cultured in EMEM medium, EBC-1 cells and SNU-5 cells will be cultured in MEM medium, MKN45 cells, NCI-H1975 cells and NCI-H1993 cells will be cultured in RPMI1640 medium, A549 cells will be cultured in McCoy's 5a medium. All the cells will be cultured in the media supplemented with 10% FBS, in the temperature of 37° C., 5% $CO_2$ and 95% humidity. All culture media will be purchased from GIBCO (USA). The cells will be harvested respectively during the logarithmic growth period and counted with hemocytometer. The cell viability is over 98% by trypan blue exclusion. Adjust cell concentrations to 2.22× 10$^5$ or 1.11×10$^5$ or 5.56×10$^4$ cells/ml with respective medium. Add 90 W cell suspensions to 96-well plates (triplicates for each cell concentration), the final cell densities are 2×10$^4$ or 1×10$^4$ or 5×10$^3$ cells/well. The density of 5×10$^3$ cells/well will be used for our first test. The appropriate cell density will be determined and adjusted according to the results of our first test. The next day, dissolve the test article or positive drugs with DMSO or PBS as stock solution. Dispense 2 µl drug solution in 1 ml culture media. Add 200 µl drug media into 96-well plates (triplicate for each drug concentration) after discard the old media. The final concentration of drug will be 0, 0.03, 0.1, 0.3, 1, 3, 10, 30 or 100 µM. The plates will be cultured for another 7 days, then measured by means of MTS assay. Prepare MTS/PMS solution immediately prior to use, pipet 20 µl of the mixture into each well of the 96 well assay plate containing 100 µl culture media. (The final reaction volume is 120 µl). Incubate the plate for 1-4 hours at 37° C. in a humidified, 5% $CO_2$ atmosphere. Record the absorbance at 490 nm using Victor X5 microplate spectrophotometer.

TABLE 2

| | IC$_{50}$ (µM) | | | | | | |
| --- | --- | --- | --- | --- | --- | --- | --- |
| Example | U87-MG | EBC-1 | MKN45 | NCI-H1975 | A549 | NCI-H1993 | SNU5 |
| 1 | 3.4 | 0.06 | 0.4 | 13.0 | 15.4 | 0.4 | 0.9 |
| 3 | 6.3 | 0.4 | 6.2 | 14.6 | 20.1 | 1.5 | 3.1 |
| 7 | 5.1 | 9.4 | 6.7 | 17.8 | 23.3 | 4.6 | 7.8 |
| 9 | 5.5 | 0.6 | 1.3 | 8.3 | 15.7 | 7.9 | 2.9 |
| 12 | 3.8 | 11.1 | 11.5 | 23.2 | 20.6 | 9.2 | 9.3 |
| 56 | 4.7 | 0.1 | 1.2 | 14.3 | 18.1 | 0.7 | 1.7 |

Xenograft Tumor Models

Human non small cell lung cancer cells A549, human gastric cancer cells MKN45, and human lung squamous cell carcinoma cells EBC-1 are expanded in culture, harvested, and injected subcutaneously onto the right flank of BALB/c nude mice. Testing compound is prepared in an appropriate vehicle and is administered by oral gavage when tumors are established (6-10 days after implant). Tumor response is determined by tumor volume measurement performed twice a week during the course of treatment. Tumor volume inhibition (% growth inhibition) is calculated by comparing treated groups to vehicle control group. Body weight is taken as a general measurement of toxicity. The Compound of Example 1 demonstrates excellent anti-tumor activity in these models. For example, when dosed at 60 and 120 mg/kg (qd x24), Example 1 is able to cause 76.6% and 96.7% growth inhibition of A549 tumors, respectively. When dosed at 60 and 120 mg/kg (qd x22), Example 1 is able to cause 38.9% and 71.9% growth inhibition of MKN45 tumors, respectively. When dosed at 40 and 80 mg/kg (qd x17), Example 1 is able to cause 56.5% and 100% growth inhibition of EBC-1 tumors, respectively.

c-Met relevant tumors and xenograft models c-Met overexpression is a common feature for many human tumors, including lung, breast, colorectal, gastric, renal, pancreatic, head and neck[1,2]. c-Met activating mutations in the kinase domain are implicated as the cause for several tumors, such as hereditary papillary renal cell carcinoma, childhood hepatocellular carcinoma, and gastric cancer[3-6]. c-Met inhibitors from Pfizer demonstrated antitumor efficacy in many human xenograft tumors, including U87MG, GTL16, H441, Caki-1, and PC3[7].

1. Christinsen, J G., Burrows, J., and Salgia, R. Cancer Letters 225: 1-26, 2005.
2. Birchmeier, C, Birchmeier, W., Gherardi, E., and Vande Woude, G F. Nat Rev Mol Cell Biol 4: 915-925, 2003.
3. Di Renzo, M F., Olivero, M., Martone, T. Et al. Oncogene 19: 1547-1555, 2000.
4. Lee, J H., Han, S U, Cho, H. et al. Oncogene 19: 4947-4953, 2000.
5. Ma, P C, Kijima, T., Maulik, G. et al. Cancer Res 63: 6272-6281, 2003. 6. Park, W S., Dong, S M., Kim, S Y. et al. Cancer Res 59: 307-310, 1999.
6. Schmidt, L., Duh, F M., Chen, F., et al. Nat Genet 16: 68-73, 1997.
7. Zou, H Y., Li, Qiuhua., Lee, J H., et al. Cancer Res 67: 4408-4417, 2007.

The compounds of the present invention are preferably formulated as pharmaceutical compositions administered by a variety of routes. Most preferably, such compositions are for oral administration. Such pharmaceutical compositions and processes for preparing the same are well known in the art. See, e.g., REMINGTON: THE SCIENCE AND PRACTICE OF PHARMACY (A. Gennaro, et al, eds., 19th ed., Mack Publishing Co., 1995). The compounds of Formula I are generally effective over a wide dosage range.

For example, dosages per day normally fall within the range of about 1 mg to about 200 mg total daily dose, preferably 1 mg to 150 mg total daily dose, more preferably 1 mg to 50 mg total daily dose. In some instances dosage levels below the lower limit of the aforesaid range may be more than adequate, while in other cases still larger doses may be employed. The above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

What is claimed is:

1. A compound of Formula I or a pharmaceutically acceptable salt, solvate, chelate, non-covalent complex, or prodrug thereof:

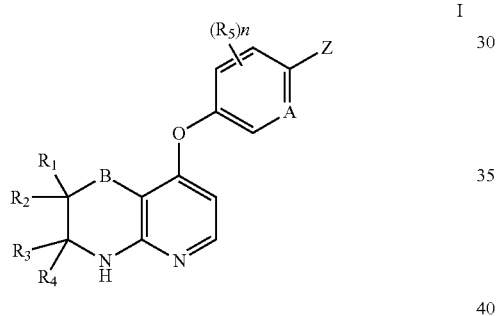

wherein,

B is absent, O, S, $OCH_2$, or $SCH_2$;

$R_1$, $R_2$, $R_3$ and $R_4$ are each independently hydrogen, halogen, substituted or unsubstituted $C_{1-6}$ alkyl, substituted or unsubstituted $C_{2-8}$alkenyl, substituted or unsubstituted $C_{2-8}$alkynyl, substituted or unsubstituted aryl, substituted or unsubstituted heteroaryl, substituted or unsubstituted heterocyclyl, $C_{1-8}$alkanoyl, ($C_{1-8}$alkoxy)carbonyl, $C_{1-8}$alkylsulphinyl, $C_{1-8}$alkylsulphonyl, arylsulphonyl, —CN, —NO$_2$, hydroxy, amino, carboxy, oxo, carbamoyl, $C_{1-8}$alkoxy, $C_{2-8}$alkenyloxy, $C_{2-8}$alkynyloxy, $C_{1-8}$alkylthio, N—($C_{1-8}$alkyl)carbamoyl, N,N-di($C_{1-8}$alkyl)carbamoyl, $C_{1-8}$alkanoyloxy, $C_{1-8}$alkanoylamino, $C_{3-8}$alkynoylamino, N—($C_{1-8}$alkyl)sulphamoyl, or N,N-di($C_{1-8}$alkyl)sulphamoyl; or $R_1$ and $R_2$ together, or $R_3$ and $R_4$ together, form =O;

A is N or CH;

n is 0, 1, 2, or 3;

each $R_5$ is independently halogen, substituted or unsubstituted $C_{1-6}$alkyl, —CN, —NO$_2$, —OR$_{50}$, —N(R$_{50}$)$_2$, —S(O)$_{0-2}$R$_{50}$, or —C(O)R$_{50}$;

each $R_{50}$ is independently hydrogen, or substituted or unsubstituted $C_{1-6}$alkyl;

Z is NHR$_6$ or of Formula II:

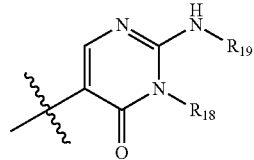

wherein $R_{18}$ and $R_{19}$ are each independently hydrogen, substituted or unsubstituted $C_{1-8}$alkyl, substituted or unsubstituted $C_{2-8}$alkenyl, substituted or unsubstituted $C_{2-8}$alkynyl, substituted or unsubstituted aryl, substituted or unsubstituted heteroaryl, substituted or unsubstituted heterocyclyl, $C_{1-8}$alkanoyl, ($C_{1-8}$alkoxy)carbonyl, $C_{1-8}$alkylsulphinyl, $C_{1-8}$alkylsulphonyl, or arylsulphonyl;

$R_6$ is of Formula III, IV, V, VI, or VII:

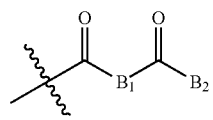

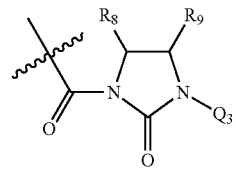

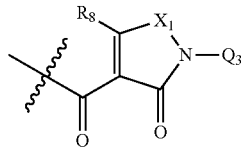

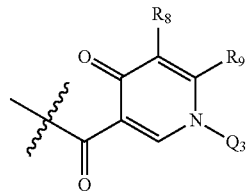

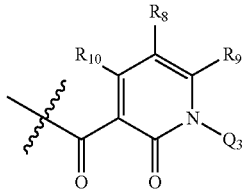

further when $R_6$ is VII, B is O, S, $OCH_2$, or $SCH_2$; wherein:

$B_1$ is

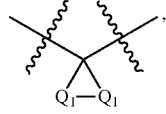

wherein each $Q_1$ is independently $C(R_7)_2$;

$B_2$ is $NHQ_2$, and $Q_2$ is substituted or unsubstituted aryl, substituted or unsubstituted heteroaryl, substituted or unsubstituted heterocyclyl, substituted or unsubstituted ($C_{1-8}$alkyl)aryl, substituted or unsubstituted ($C_{1-8}$alkyl)heteroaryl, or substituted or unsubstituted ($C_{1-8}$alkyl)heterocyclyl; or $B_1$ and $B_2$, together with the carbonyl group therebetween, form a 5- to 10-membered substituted or unsubstituted heteroaryl, or substituted or unsubstituted heterocyclyl;

$Q_3$ is hydrogen, substituted or unsubstituted aryl, substituted or unsubstituted alkyl, substituted or unsubstituted heteroaryl, substituted or unsubstituted heterocyclyl, substituted or unsubstituted ($C_{1-8}$alkyl)aryl, substituted or unsubstituted ($C_{1-8}$alkyl)heteroaryl, or substituted or unsubstituted ($C_{1-8}$alkyl)heterocyclyl;

$X_1$ is $NR_8$ or $CR_8R_9$;

$R_7$, $R_8$, $R_9$ and $R_{10}$ are each independently hydrogen, halogen, substituted or unsubstituted $C_{1-8}$alkyl, substituted or unsubstituted $C_{2-8}$alkenyl, substituted or unsubstituted $C_{2-8}$alkynyl, substituted or unsubstituted aryl, substituted or unsubstituted heteroaryl, substituted or unsubstituted heterocyclyl, $C_{1-8}$alkanoyl, ($C_{1-8}$alkoxy)carbonyl, $C_{1-8}$alkylsulphinyl, $C_{1-8}$alkylsulphonyl, arylsulphonyl, —CN, —$NO_2$, hydroxy, amino, carboxy, oxo, carbamoyl, $C_{1-8}$ alkoxy, $C_{2-8}$alkenyloxy, $C_{2-8}$alknyloxy, $C_{1-8}$alkylthio, N—($C_{1-8}$alkyl)carbamoyl, N,N-di($C_{1-8}$alkyl)carbamoyl, $C_{1-8}$alkanoyloxy, $C_{1-8}$alkanoylamino, $C_{3-8}$alkynoylamino, N—($C_{1-8}$alkyl)sulphamoyl, N,N-di($C_{1-8}$alkyl)sulphamoyl, substituted or unsubstituted $C_{1-8}$alkylaryl, substituted or unsubstituted $C_{1-8}$alkylheteroaryl, or substituted or unsubstituted $C_{1-8}$ alkylheterocyclyl.

2. The compound of claim 1, wherein $R_1$, $R_2$, $R_3$ and $R_4$ are each independently hydrogen, halogen, substituted or unsubstituted $C_{1-4}$alkyl, substituted or unsubstituted $C_{6-8}$aryl, —CN, —$NO_2$, hydroxy, amino, carboxy, oxo, carbamoyl, or $C_{1-5}$alkoxy; or $R_1$ and $R_2$ together, or $R_3$ and $R_4$ together, form =O; or a pharmaceutically acceptable salt, solvate, chelate, non-covalent complex, or prodrug thereof.

3. The compound of claim 1, wherein $R_1$, $R_2$, $R_3$ and $R_4$ are each independently hydrogen, F, or methyl; or $R_1$ and $R_2$ together, or $R_3$ and $R_4$ together, form =O; or a pharmaceutically acceptable salt, solvate, chelate, non-covalent complex, or prodrug thereof.

4. The compound of claim 1, wherein $R_1$, $R_2$, $R_3$ and $R_4$ are all hydrogen; or a pharmaceutically acceptable salt, solvate, chelate, non-covalent complex, or prodrug thereof.

5. The compound of claim 1, wherein $R_1$ and $R_2$ together, or $R_3$ and $R_4$ together, form =O; or a pharmaceutically acceptable salt, solvate, chelate, non-covalent complex, or prodrug thereof.

6. The compound of claim 1, wherein n is 0 or 1; or a pharmaceutically acceptable salt, solvate, chelate, non-covalent complex, or prodrug thereof.

7. The compound of claim 1, wherein $R_5$ is halogen, or substituted or unsubstituted $C_{1-4}$alkyl; or a pharmaceutically acceptable salt, solvate, chelate, non-covalent complex, or prodrug thereof.

8. The compound of claim 1, wherein $R_5$ is F or methyl; or a pharmaceutically acceptable salt, solvate, chelate, non-covalent complex, or prodrug thereof.

9. The compound of claim 1, wherein B is absent or O; or a pharmaceutically acceptable salt, solvate, chelate, non-covalent complex, or prodrug thereof.

10. The compound of claim 1, wherein A is CH; or a pharmaceutically acceptable salt, solvate, chelate, non-covalent complex, or prodrug thereof.

11. The compound of claim 1, wherein Z is of Formula II; $R_{18}$ and $R_{19}$ are each independently hydrogen, substituted or unsubstituted $C_{1-4}$alkyl, or substituted or unsubstituted $C_{6-8}$aryl; or a pharmaceutically acceptable salt, solvate, chelate, non-covalent complex, or prodrug thereof.

12. The compound of claim 1, wherein Z is of Formula II; $R_{18}$ and $R_{19}$ are each independently hydrogen, methyl, or phenyl substituted with halogen; or a pharmaceutically acceptable salt, solvate, chelate, non-covalent complex, or prodrug thereof.

13. The compound of claim 1, wherein Z is

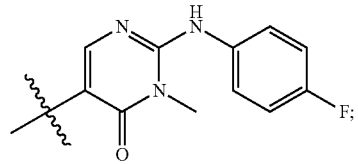 [SMILES: *c1cnc(Nc2ccc(F)cc2)n(C)c1=O]

or a pharmaceutically acceptable salt, solvate, chelate, non-covalent complex, or prodrug thereof.

14. The compound of claim 1, wherein Z is $NHR_6$; $R_6$ is of Formula IV, V, VI, or VII; and $Q_3$, $R_8$, $R_9$ and $R_{10}$ are each independently hydrogen, halogen, substituted or unsubstituted $C_{1-3}$alkyl, or substituted or unsubstituted $C_{6-8}$aryl; or a pharmaceutically acceptable salt, solvate, chelate, non-covalent complex, or prodrug thereof.

15. The compound of claim 1, wherein Z is $NHR_6$, $R_6$ is of Formula IV, V, VI, or VII; and $Q_3$, $R_8$, $R_9$ and $R_{10}$ are each independently hydrogen, methyl, phenyl, or phenyl substituted with halogen; or a pharmaceutically acceptable salt, solvate, chelate, non-covalent complex, or prodrug thereof.

16. The compound of claim 1, wherein $Q_3$ is hydrogen, phenyl or phenyl substituted with F at para-position; or a pharmaceutically acceptable salt, solvate, chelate, non-covalent complex, or prodrug thereof.

17. The compound of claim 1, wherein $R_8$ is phenyl or phenyl substituted with halogen, and $R_9$ is hydrogen; or a pharmaceutically acceptable salt, solvate, chelate, non-covalent complex, or prodrug thereof.

18. The compound of claim 1, wherein $X_1$ is $NR_8$ and $R_8$ is hydrogen or $C_{1-3}$alkyl; or a pharmaceutically acceptable salt, solvate, chelate, non-covalent complex, or prodrug thereof.

19. The compound of claim 1, wherein $X_1$ is $NR_8$ and $R_8$ is methyl; or a pharmaceutically acceptable salt, solvate, chelate, non-covalent complex, or prodrug thereof.

20. The compound of claim 1, wherein $R_8$, $R_9$ and $R_{10}$ are all hydrogen; or a pharmaceutically acceptable salt, solvate, chelate, non-covalent complex, or prodrug thereof.

21. The compound of claim 1, wherien Z is $NHR_6$ and $R_6$ is of Formula III; $R_7$ is hydrogen, halogen, or substituted or unsubstituted $C_{1-3}$alkyl; and $Q_2$ is substituted or unsubstituted $C_{6-8}$aryl, or substituted or unsubstituted $C_{6-8}$heteroaryl; or a pharmaceutically acceptable salt, solvate, chelate, non-covalent complex, or prodrug thereof.

22. The compound of claim 1, wherein $R_7$ is hydrogen; and $Q_2$ is phenyl substituted with halogen; or a pharmaceutically acceptable salt, solvate, chelate, non-covalent complex, or prodrug thereof.

23. The compound of claim 1, wherein Z is NHR$_6$ and R$_6$ is

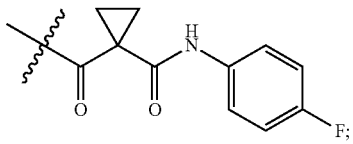 [SMILES: *C(=O)C1(C(=O)Nc2ccc(F)cc2)CC1]

or a pharmaceutically acceptable salt, solvate, chelate, non-covalent complex, Or prodrug thereof.

24. The compound of claim 1, wherein the compound is of Formula VIII:

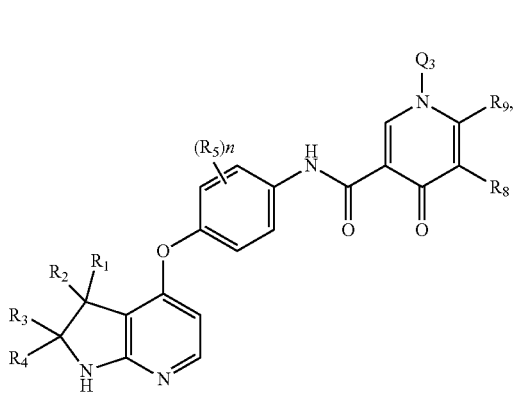

wherein
R$_1$, R$_2$, R$_3$ and R$_4$ are each independently hydrogen, halogen, or substituted or unsubstituted C$_{1-3}$alkyl; or
R$_1$ and R$_2$ together, or R$_3$ and R$_4$ together, form =O;
each R$_5$ is independently halogen, or substituted or unsubstituted C$_{1-3}$alkyl;
n is 0 or 1;
Q$_3$ is hydrogen, or substituted or unsubstituted C$_{6-8}$aryl; and
R$_8$ and R$_9$ are each independently hydrogen, methyl, or phenyl substituted with halogen; or
a pharmaceutically acceptable salt, solvate, chelate, non-covalent complex, or prodrug thereof.

25. The compound of claim 24, wherein R$_1$, R$_2$, R$_3$ and R$_4$ are each independently hydrogen, or halogen; or R$_1$ and R$_2$ together, or R$_3$ and R$_4$ together, form =O; and R$_8$ and R$_9$ are each independently hydrogen, phenyl, or phenyl substituted with halogen; or a pharmaceutically acceptable salt, solvate, chelate, non-covalent complex, or prodrug thereof.

26. The compound of claim 24, wherein R$_1$, R$_2$, R$_3$ and R$_4$ are each independently hydrogen or halogen; or a pharmaceutically acceptable salt, solvate, chelate, non-covalent complex, or prodrug thereof.

27. The compound of claim 24, wherein R$_1$ and R$_2$ together, or R$_3$ and R$_4$ together form =O; or a pharmaceutically acceptable salt, solvate, chelate, non-covalent complex, or prodrug thereof.

28. The compound of claim 24, wherein R$_5$ is halogen; or a pharmaceutically acceptable salt, solvate, chelate, non-covalent complex, or prodrug thereof.

29. The compound of claim 24, wherein R$_5$ is F and Q$_3$ is hydrogen; or a pharmaceutically acceptable salt, solvate, chelate, non-covalent complex, or prodrug thereof.

30. The compound of claim 24, wherein R$_9$ is hydrogen; R$_8$ is hydrogen or phenyl substituted with halogen; or a pharmaceutically acceptable salt, solvate, chelate, non-covalent complex, or prodrug thereof.

31. The compound of claim 24, wherein R$_9$ is hydrogen, R$_8$ is phenyl substituted with F at the para-position; or a pharmaceutically acceptable salt, solvate, chelate, non-covalent complex, or prodrug thereof.

32. A compound chosen from:
N-(4-(2,3-dihydro-1H-pyrrolo[2,3-b]pyridin-4-yloxy)-3-fluorophenyl)-5-(4-fluorophenyl)-4-oxo-1,4-dihydropyridine-3-carboxamide;
N-(3-fluoro-4-(3-oxo-3,4-dihydro-2H-pyrido[3,2-b][1,4]oxazin-8-yloxy)phenyl)-5-(4-fluorophenyl)-4-oxo-1,4-dihydropyridine-3-carboxamide;
N-(4-(3,4-dihydro-2H-pyrido[3,2-b][1,4]oxazin-8-yloxy)-3-fluorophenyl)-5-4-fluorophenyl)-4-oxo-1,4-dihydropyridine-3-carboxamide;
N-(4-(3,4-dihydro-2H-pyrido[3,2-b][1,4]oxazin-8-yloxy)phenyl)-5-(4-fluorophenyl)-4-oxo-1,4-dihydropyridine-3-carboxamide;
N-(3-fluoro-4-(2-oxo-2,3-dihydro-1H-pyrrolo[2,3-b]pyridin-4-yloxy)phenyl)-5-(4-fluorophenyl)-4-oxo-1,4-dihydropyridine-3-carboxamide;
N-(3-fluoro-4-(3-oxo-3,4-dihydro-2H-pyrido[3,2-b][1,4]oxazin-8-yloxy)phenyl)-1-(4-fluorophenyl)-2-oxo-1,2-dihydropyridine-3-carboxamide;
N-(4-(3,4-dihydro-2H-pyrido[3,2-b][1,4]oxazin-8-yloxy)-3-fluorophenyl)-1-(4-fluorophenyl)-2-oxo-1,2-dihydropyridine-3-carboxamide;
N-(4-(3,4-dihydro-2H-pyrido[3,2-b][1,4]oxazin-8-yloxy)phenyl)-1-(4-fluorophenyl)-2-oxo-1,2-dihydropyridine-3-carboxamide;
N-(3-fluoro-4-(3-oxo-3,4-dihydro-2H-pyrido[3,2-b][1,4]oxazin-8-yloxy)phenyl)-N-(4-fluorophenyl)cyclopropane-1,1-dicarboxamide;
N-(4-(2,3-dihydro-1H-pyrrolo[2,3-b]pyridin-4-yloxy)-3-fluorophenyl)-N-(4-fluorophenyl)cyclopropane-1,1-dicarboxamide;
N-(4-(3,4-dihydro-2H-pyrido[3,2-b][1,4]oxazin-8-yloxy)-3-fluorophenyl)-N-(4-fluorophenyl)cyclopropane-1,1-dicarboxamide;
N-(4-(3,4-dihydro-2H-pyrido[3,2-b][1,4]oxazin-8-yloxy)phenyl)-N-(4-fluorophenyl)cyclopropane-1,1-dicarboxamide;
N-(3-fluoro-4-(2-oxo-2,3-dihydro-1H-pyrrolo[2,3-b]pyridin-4-yloxy)phenyl)-N-(4-fluorophenyl)cyclopropane-1,1-dicarboxamide;
8-(6-(2-(4-fluorophenylamino)-1-methyl-6-oxo-1,6-dihydropyrimidin-5-yl)pyridin-3-yloxy)-2H-pyrido[3,2-b][1,4]oxazin-3 (4H)-one;
5-(5-(2,3-dihydro-1H-pyrrolo[2,3-b]pyridin-4-yloxy)pyridin-2-yl)-2-(4-fluorophenylamino)-3-methylpyrimidin-4(3H)-one;
N-(3-fluoro-4-(3-oxo-3,4-dihydro-2H-pyrido[3,2-b][1,4]oxazin-8-yloxy)phenyl)-1,5-dimethyl-3-oxo-2-phenyl-2,3-dihydro-1H-pyrazole-4-carboxamide;
N-(4-(2,3-dihydro-1H-pyrrolo[2,3-b]pyridin-4-yloxy)-3-fluorophenyl)-1,5-dimethyl-3-oxo-2-phenyl-2,3-dihydro-1H-pyrazole-4-carboxamide;
N-(4-(3,4-dihydro-2H-pyrido[3,2-b][1,4]oxazin-8-yloxy)-3-fluorophenyl)-1,5-dimethyl-3-oxo-2-phenyl-2,3-dihydro-1H-pyrazole-4-carboxamide;
N-(4-(3,4-dihydro-2H-pyrido[3,2-b][1,4]oxazin-8-yloxy)phenyl)-5-(4-fluorophenyl)-4-oxo-1,4-dihydropyridine-3-carboxamide;

5-(4-Fluoro-phenyl)-4-oxo-1,4-dihydro-pyridine-3-carboxylic acid [4-(3,4-dihydro-2H-pyrido[3,2-b][1,4]thiazin-8-yloxy)-3-fluoro-phenyl]-amide;

5-(4-Fluoro-phenyl)-4-oxo-1,4-dihydro-pyridine-3-carboxylic acid [4-(3,4-dihydro-2H-pyrido[3,2-b][1,4]thiazin-8-yloxy)-phenyl]-amide;

1-(4-Fluoro-phenyl)-2-oxo-1,2-dihydro-pyridine-3-carboxylic acid [4-(3,4-dihydro-2H-pyrido[3,2-h][1,4]thiazin-8-yloxy)-3-fluoro-phenyl]-amide;

1-(4-Fluoro-phenyl)-2-oxo-1,2-dihydro-pyridine-3-carboxylic acid [4-(3,4-dihydro-2H-pyrido[3,2-b][1,4]thiazin-8-yloxy)-phenyl]-amide;

Cyclopropane-1,1-dicarboxylic acid [4-(3,4-dihydro-2H-pyrido[3,2-b][1,4]thiazin-8-yloxy)-phenyl]-amide (4-fluoro-phenyl)-amide;

Cyclopropane-1,1-dicarboxylic acid [4-(3,4-dihydro-2H-pyrido[3,2-b][1,4]thiazin-8-yloxy)-3-fluoro-phenyl]-amide (4-fluoro-phenyl)-amide;

5-[5-(3,4-Dihydro-2H-pyrido[3,2-b][1,4]thiazin-8-yloxy)-pyridin-2-yl]-2-(4-fluoro-phenylamino)-3-methyl-3H-pyrimidin-4-one;

5-[5-(3,3-Dimethyl-3,4-dihydro-2H-pyrido[3,2-b][1,4]thiazin-8-yloxy)-pyridin-2-yl]-2-(4-fluoro-phenylamino)-3-methyl-3H-pyrimidin-4-one;

5-(4-Fluoro-phenyl)-4-oxo-1,4-dihydro-pyridine-3-carboxylic acid [4-(3,3-dimethyl-3,4-dihydro-2H-pyrido[3,2-b][1,4]thiazin-8-yloxy)-3-fluoro-phenyl]-amide;

5-(4-Fluoro-phenyl)-4-oxo-1,4-dihydro-pyridine-3-carboxylic acid [4-(3,3-dimethyl-3,4-dihydro-2H-pyrido[3,2-b][1,4]thiazin-8-yloxy)-phenyl]-amide 1-(4-Fluoro-phenyl)-2-oxo-1,2-dihydro-pyridine-3-carboxylic acid [4-(3,3-dimethyl-3,4-dihydro-2H-pyrido[3,2-b][1,4]thiazin-8-yloxy)-3-fluoro-phenyl]-amide;

1-(4-Fluoro-phenyl)-2-oxo-1,2-dihydro-pyridine-3-carboxylic acid [4-(3,3-dimethyl-3,4-dihydro-2H-pyrido[3,2-b][1,4]thiazin-8-yloxy)-phenyl]-amide Cyclopropane-1,1-dicarboxylic acid [4-(3,3-dimethyl-3,4-dihydro-2H-pyrido[3,2-b][1,4]thiazin-8-yloxy)-phenyl]-amide (4-fluoro-phenyl)-amide;

Cyclopropane-1,1-dicarboxylic acid [4-(3,3-dimethyl-3,4-dihydro-2H-pyrido[3,2-b][1,4]thiazin-8-yloxy)-3-fluoro-phenyl]-amide(4-fluoro-phenyl)-amide;

5-[5-(3,3-Dimethyl-3,4-dihydro-2H-pyrido[3,2-b][1,4]oxazin-8-yloxy)-pyridin-2-yl]-2-(4-fluoro-phenylamino)-3-methyl-3H-pyrimidin-4-one;

5-(4-Fluoro-phenyl)-4-oxo-1,4-dihydro-pyridine-3-carboxylic acid [4-(3,3-dimethyl-3,4-dihydro-2H-pyrido[3,2-b][1,4]oxazin-8-yloxy)-3-fluoro-phenyl]-amide;

5-(4-Fluoro-phenyl)-4-oxo-1,4-dihydro-pyridine-3-carboxylic acid [4-(3,3-dimethyl-3,4-dihydro-2H-pyrido[3,2-b][1,4]oxazin-8-yloxy)-phenyl]-amide;

1-(4-Fluoro-phenyl)-2-oxo-1,2-dihydro-pyridine-3-carboxylic acid [4-(3,3-dimethyl-3,4-dihydro-2H-pyrido[3,2-b][1,4]oxazin-8-yloxy)-3-fluoro-phenyl]-amide;

1-(4-Fluoro-phenyl)-2-oxo-1,2-dihydro-pyridine-3-carboxylic acid [4-(3,3-dimethyl-3,4-dihydro-2H-pyrido[3,2-b][1,4]oxazin-8-yloxy)-phenyl]-amide;

Cyclopropane-1,1-dicarboxylic acid [4-(3,3-dimethyl-3,4-dihydro-2H-pyrido[3,2-b][1,4]oxazin-8-yloxy)-phenyl]-amide (4-fluoro-phenyl)-amide;

Cyclopropane-1,1-dicarboxylic acid [4-(3,3-dimethyl-3,4-dihydro-2H-pyrido[3,2-b][1,4]oxazin-8-yloxy)-3-fluoro-phenyl]-amide(4-fluoro-phenyl)-amide;

5-(4-Fluoro-phenyl)-4-oxo-1,4-dihydro-pyridine-3-carboxylic acid [4-(6,7,8,9-tetrahydro-5-thia-1,9-diaza-benzocyclohepten-4-yloxy)-phenyl]-amide;

1-(4-Fluoro-phenyl)-2-oxo-1,2-dihydro-pyridine-3-carboxylic acid [3-fluoro-4-(6,7,8,9-tetrahydro-5-thia-1,9-diaza-benzocyclohepten-4-yloxy)-phenyl]-amide;

Cyclopropane-1,1-dicarboxylic acid (4-fluoro-phenyl)-amide[4-(6,7,8,9-tetrahydro-5-thia-1,9-diaza-benzocyclohepten-4-yloxy)-phenyl]-amide;

Cyclopropane-1,1-dicarboxylic acid (4-fluoro-phenyl)-amide[3-fluoro-4-(6,7,8,9-tetrahydro-5-thia-1,9-diaza-benzocyclohepten-4-yloxy)-phenyl]-amide;

2-(4-Fluoro-phenylamino)-3-methyl-5-[5-(6,7,8,9-tetrahydro-5-thia-1,9-diaza-benzocyclohepten-4-yloxy)-pyridin-2-yl]-3H-pyrimidin-4-one;

5-(4-Fluoro-phenyl)-4-oxo-1,4-dihydro-pyridine-3-carboxylic acid [3-fluoro-4-(6,7,8,9-tetrahydro-5-thia-1,9-diaza-benzocyclohepten-4-yloxy)-phenyl]-amide;

1-(4-Fluoro-phenyl)-2-oxo-1,2-dihydro-pyridine-3-carboxylic acid [4-(6,7,8,9-tetrahydro-5-thia-1,9-diaza-benzocyclohepten-4-yloxy)-phenyl]-amide;

5-(4-Fluoro-phenyl)-4-oxo-1,4-dihydro-pyridine-3-carboxylic acid [3-fluoro-4-(6,7,8,9-tetrahydro-5-oxa-1,9-diaza-benzocyclohepten-4-yloxy)-phenyl]-amide;

1-(4-Fluoro-phenyl)-2-oxo-1,2-dihydro-pyridine-3-carboxylic acid [4-(6,7,8,9-tetrahydro-5-oxa-1,9-diaza-benzocyclohepten-4-yloxy)-phenyl]-amide;

2-(4-Fluoro-phenylamino)-3-methyl-5-[5-(6,7,8,9-tetrahydro-5-oxa-1,9-diaza-benzocyclohepten-4-yloxy)-pyridin-2-yl]-3H-pyrimidin-4-one;

Cyclopropane-1,1-dicarboxylic acid (4-fluoro-phenyl)-amide[3-fluoro-4-(6,7,8,9-tetrahydro-5-oxa-1,9-diaza-benzocyclohepten-4-yloxy)-phenyl]-amide;

Cyclopropane-1,1-dicarboxylic acid (4-fluoro-phenyl)-amide[4-(6,7,8,9-tetrahydro-5-oxa-1,9-diaza-benzocyclohepten-4-yloxy)-phenyl]-amide;

1-(4-Fluoro-phenyl)-2-oxo-1,2-dihydro-pyridine-3-carboxylic acid [3-fluoro-4-(6,7,8,9-tetrahydro-5-oxa-1,9-diaza-benzocyclohepten-4-yloxy)-phenyl]-amide;

5-(4-Fluoro-phenyl)-4-oxo-1,4-dihydro-pyridine-3-carboxylic acid [4-(6,7,8,9-tetrahydro-5-oxa-1,9-diaza-benzocyclohepten-4-yloxy)-phenyl]-amide;

N-(4-(3,4-dimethyl-2,3,4,5-tetrahydropyrido[3,2-b][1,4]oxazepin-9-yloxy)phenyl)-5-(4-fluorophenyl)-4-oxo-1,4-dihydropyridine-3-carboxamide;

1-(4-Fluoro-phenyl)-2-oxo-1,2-dihydro-pyridine-3-carboxylic acid [4-(7,7-dimethyl-6,7,8,9-tetrahydro-5-thia-1,9-diaza-benzocyclohepten-4-yloxy)-phenyl]-amide;

5-(4-Fluoro-phenyl)-4-oxo-1,4-dihydro-pyridine-3-carboxylic acid [4-(3,3-difluoro-2,3-dihydro-1H-pyrrolo[2,3-b]pyridin-4-yloxy)-3-fluoro-phenyl]-amide;

N-(4-(2,2-difluoro-2,3-dihydro-1H-pyrrolo[2,3-b]pyridin-4-yloxy)-3-fluorophenyl)-5-(4-fluorophenyl)-4-oxo-1,4-dihydropyridine-3-carboxamide;

N-(3-fluoro-5-methyl-4-(2-oxo-2,3-dihydro-1H-pyrrolo[2,3-b]pyridin-4-yloxy)phenyl)-N-(4-fluorophenyl)cyclopropane-1,1-dicarboxamide;

Cyclopropane-1,1-dicarboxylic acid [2,3-difluoro-4-(2-oxo-2,3-dihydro-1H-pyrrolo[2,3-b]pyridin-4-yloxy)-phenyl]-amide(4-fluoro-phenyl)-amide;

3-(4-Fluoro-phenyl)-2-oxo-imidazolidine-1-carboxylic acid [4-(2,3-di-hydro-1H-pyrrolo [2,3-b]pyridin-4-yloxy)-3-fluoro-phenyl]-amide;

3-(4-Fluoro-phenyl)-2-oxo-imidazolidine-1-carboxylic acid [4-(3,4-di-hydro-2H-pyrido [3,2-b][1,4]oxazin-8-yloxy)-3-fluoro-phenyl]-amide;

3-(4-Fluoro-phenyl)-2-oxo-imidazolidine-1-carboxylic acid [4-(3,4-di-hydro-2H-pyrido [3,2-b][1,4]thiazin-8-yloxy)-3-fluoro-phenyl]-amide;

3-(4-Fluoro-phenyl)-2-oxo-imidazolidine-1-carboxylic acid [3-fluoro-4-(6,7,8,9-tetrahydro-5-oxa-1,9-diaza-benzocyclohepten-4-yloxy)-phenyl]-amide;

N-(4-(3',4'-dihydrospiro[cyclopropane-1,2'-pyrido[3,2-b][1,4]oxazine]-8'-yloxy)-3-fluorophenyl)-5-(4-fluorophenyl)-4-oxo-1,4-dihydropyridine-3-carboxamide;

N-(3-fluoro-4-(2-(hydroxymethyl)-3,4-dihydro-2H-pyrido[3,2-b][1,4]oxazin-8-yloxy)phenyl)-5-(4-fluorophenyl)-4-oxo-1,4-dihydropyridine-3-carboxamide;

8-(2-fluoro-4-(5-(4-fluorophenyl)-4-oxo-1,4-dihydropyridine-3-carboxamido)phenoxy)-3,4-dihydro-2H-pyrido[3,2-b][1,4]oxazine-2-carboxamide;

N-(4-(2-(aziridin-1-ylmethyl)-3,4-dihydro-2H-pyrido[3,2-b][1,4]oxazin-8-yloxy)-3-fluorophenyl)-5-(4-fluorophenyl)-4-oxo-1,4-dihydropyridine-3-carboxamide;

N-(3-fluoro-4-(3-(2-hydroxyethyl)-2,3-dihydro-1H-pyrrolo[2,3-b]pyridin-4-yloxy)phenyl)-5-(4-fluorophenyl)-4-oxo-1,4-dihydropyridine-3-carboxamide; or N-(3-fluoro-4-(2'-oxo-1',2'-dihydrospiro[cyclopropane-1,3'-pyrrolo[2,3-b]pyridine]-4'-yloxy)phenyl)-5-(4-fluorophenyl)-4-oxo-1,4-dihydropyridine-3-carboxamide;

or a pharmaceutically acceptable salt, solvate, chelate, non-covalent complex, or prodrug thereof.

33. A pharmaceutical composition comprising a compound of claim 1 or a pharmaceutically acceptable salt, solvate, chelate, non-covalent complex, or prodrug thereof and a pharmaceutically acceptable excipient.

34. The pharmaceutical composition according to claim 33, wherein, the weight ratio of said compound or a pharmaceutically acceptable salt, solvate, chelate, non-covalent complex, or prodrug thereof to said excipient ranges from about 0.0001 to about 10.

35. A method for treating a condition mediated by c-MET activity in a patient in need thereof, comprising administering to the patient a therapeutically effective amount of a compound of claim 1 or a pharmaceutically acceptable salt, solvate, chelate, non-covalent complex, or prodrug thereof.

36. The method of claim 35, wherein the condition mediated by c-MET activity is cancer.

37. The method of claim 36, wherein the cancer is a lung cancer, breast cancer, colorectal cancer, renal cancer, pancreatic cancer, head cancer, neck cancer, hereditary papillary renal cell carcinoma, childhood hepatocellular carcinoma, gastric cancer, solid tumor, a sarcoma, fibrosarcoma, osteoma, melanoma, retinoblastoma, a rhabdomyosarcoma, glioblastoma, neuroblastoma, teratocarcinoma, an hematopoietic malignancy, or malignant ascites.

38. The compound of claim 1, wherein Z is $NHR_6$, $R_6$ is

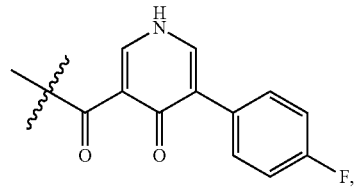

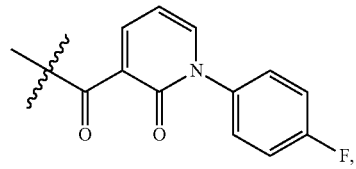

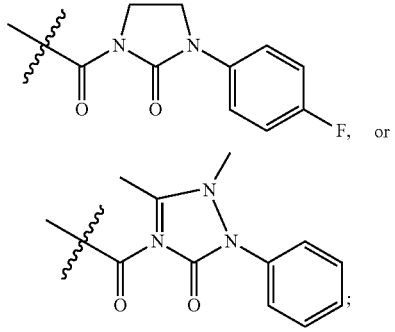

or a pharmaceutically acceptable salt, solvate, chelate, non-covalent complex, or prodrug thereof.

* * * * *

UNITED STATES PATENT AND TRADEMARK OFFICE
CERTIFICATE OF CORRECTION

PATENT NO. : 9,617,257 B2
APPLICATION NO. : 14/411515
DATED : April 11, 2017
INVENTOR(S) : Hu et al.

Page 1 of 1

It is certified that error appears in the above-identified patent and that said Letters Patent is hereby corrected as shown below:

On the Title Page

Item (71), Line 1, "Beta" should read -- Betta --.

In the Claims

Claim 32, Column 80, Line 52, "[1,4]oxazin-3 (4H)-one;" should read -- [1,4]oxazin-3(4H)-one; --.

Signed and Sealed this
Twenty-sixth Day of December, 2017

Joseph Matal
*Performing the Functions and Duties of the*
*Under Secretary of Commerce for Intellectual Property and*
*Director of the United States Patent and Trademark Office*